US012565467B2

(12) United States Patent
Bazan et al.

(10) Patent No.: US 12,565,467 B2
(45) Date of Patent: *Mar. 3, 2026

(54) COMPOUNDS, COMPOSITIONS, AND METHODS FOR THE TREATMENT OF INFLAMMATORY, DEGENERATIVE, AND NEURODEGENERATIVE DISEASES

(71) Applicants: Board of Supervisors of Louisiana State University and Agricultural and Mechanical College, Baton Rouge, LA (US); University of Southern California, Los Angeles, CA (US)

(72) Inventors: Nicolas G. Bazan, New Orleans, LA (US); Nicos A. Petasis, Los Angeles, LA (US)

(73) Assignees: BOARD OF SUPERVISORS OF LOUISIANA STATE UNIVERSITY AND AGRICULTURAL AND MECHANICAL COLLEGE, Baton Rouge, LA (US); UNIVERSITY OF SOUTHERN CALIFORNIA, Los Angeles, CA (US)

( * ) Notice: Subject to any disclaimer, the term of this patent is extended or adjusted under 35 U.S.C. 154(b) by 39 days.

This patent is subject to a terminal disclaimer.

(21) Appl. No.: 18/537,355

(22) Filed: Dec. 12, 2023

(65) Prior Publication Data

US 2024/0409487 A1 Dec. 12, 2024

Related U.S. Application Data

(60) Continuation of application No. 16/859,791, filed on Apr. 27, 2020, now Pat. No. 11,858,888, which is a (Continued)

(51) Int. Cl.
*C07C 57/03* (2006.01)
*A61K 31/202* (2006.01)
(Continued)

(52) U.S. Cl.
CPC ............ *C07C 57/03* (2013.01); *A61K 31/202* (2013.01); *A61K 31/232* (2013.01); *A61P 25/28* (2018.01);
(Continued)

(58) Field of Classification Search
CPC .. A61K 31/202; A61K 31/167; A61K 9/0048; A61K 31/232; A61P 25/28;
(Continued)

(56) References Cited

U.S. PATENT DOCUMENTS 10,633,324 B2 * 4/2020 Bazan ........................ C07F 9/10
11,858,888 B2 * 1/2024 Bazan ..................... C07C 57/03
(Continued)

FOREIGN PATENT DOCUMENTS

WO 2006/055965 5/2006
WO 2013/044176 3/2013
(Continued)

OTHER PUBLICATIONS

Petasis, et al. Stereocontrolled total synthesis of Neuroprotectin D1/Protectin D1 and its aspirin-triggered stereoisomer. Tetrahedron Lett. 53, 1695-1698 (2012).
(Continued)

*Primary Examiner* — Deborah D Carr
(74) *Attorney, Agent, or Firm* — Baker, Donelson, Bearman, Caldwell, & Berkowitz, PC

(57) ABSTRACT

This disclosure provides compounds, pharmaceutical compositions, and methods of use for the prevention and treatment of inflammatory diseases or degenerative diseases including neurodegenerative diseases. Embodiments of the present disclosure provide compounds related to very long chain polyunsaturated fatty acids, pharmaceutical compositions containing the provided compounds, and methods of
(Continued)

treating a subject with a condition or disease using provided compounds or pharmaceutical compositions.

6 Claims, 13 Drawing Sheets

Related U.S. Application Data division of application No. 15/549,676, filed as application No. PCT/US2016/017112 on Feb. 9, 2016, now Pat. No. 10,633,324.

(60) Provisional application No. 62/120,229, filed on Feb. 24, 2015, provisional application No. 62/113,893, filed on Feb. 9, 2015.

(51) Int. Cl.

| | |
|---|---|
| ***A61K 31/232*** | (2006.01) |
| ***A61P 25/28*** | (2006.01) |
| ***A61P 29/00*** | (2006.01) |
| ***C07C 59/42*** | (2006.01) |
| ***C07C 69/587*** | (2006.01) |
| ***C07C 69/732*** | (2006.01) |
| ***C07F 9/10*** | (2006.01) |

(52) U.S. Cl.
CPC .............. *A61P 29/00* (2018.01); *C07C 59/42* (2013.01); *C07C 69/587* (2013.01); *C07C 69/732* (2013.01); *C07F 9/10* (2013.01); *C07F 9/106* (2013.01)

(58) Field of Classification Search
CPC .......... A61P 27/02; A61P 29/00; C07C 57/03; C07C 59/42
See application file for complete search history.

(56) References Cited

U.S. PATENT DOCUMENTS

| | | | | |
|---|---|---|---|---|
| 2009/0203787 | A1 | 8/2009 | Anderson et al. | |
| 2009/0218394 | A1 | 9/2009 | Drummond et al. | |
| 2009/0318394 | A1 | 12/2009 | Nauroth et al. | |
| 2011/0178047 | A1 | 7/2011 | Arterburn et al. | |
| 2013/0150446 | A1 | 6/2013 | Serhan et al. | |
| 2013/0190399 | A1 | 7/2013 | Raman et al. | |
| 2022/0226271 | A1* | 7/2022 | Bhatt | A61K 31/203 |

FOREIGN PATENT DOCUMENTS

| | | | | |
|---|---|---|---|---|
| WO | 2013170006 | | 11/2013 | |
| WO | WO-2018175288 | A1 * | 9/2018 | A61K 31/202 |

OTHER PUBLICATIONS

Pharmaceutical Dosage Forms and Drug Delivery Systems (1999) H.C. Ansel et al., eds., 7th ed., Lippincott, Williams, & Wilkins.
Poulos et al., Occurrence of unusual molecular species of sphingomyelin containing 28-34-carbon polyenoic fatty acids in ram spermatozoa. Biochemical Journal. 1987; 248(3):961-4.
Remington's Pharmaceutical Sciences, Mack Publishing Company, Easton, Pennsylvania, 17th edition.
Rice, D. S. et al. Disabled-1 acts downstream of Reelin in a signaling pathway that controls laminar organization in the mammalian brain. Development 125, 3119-3729 (1998).
Rice, et al. Adiponectin receptor 1 conserves docosahexaenoic acid and promotes photoreceptor cell survival. Nature Communications. 6, 6228, DOI: 10.1038/ncomms7228, Accepted Jan. 7, 2015, Published 2015, 15 pages.
Rodriguez de Turco, R B. et al. Rapid and selective uptake, metabolism, and cellular distribution of docosahexaenoic acid among rod and cone photoreceptor cells in the frog retina. J, Neurosci. 11, 3667-3678 (1991).
Saudek et al. (1989) N. Engl. J. Med. 321:574.
Sefton (1987) CRC Crit. Ref. Biomed. Eng. 14:201.
Serhan and Petasis. Resolvins and protectins in inflammation resolution. Chem. Rev. 111, 5922-5943 (2011).
Simmons, D. M. et al. A complete protocol for in situ hybridization of messenger RNAs in brain and other tissues with radiolabeled single-stranded RNA probes. J. Histotech. 12, 169-181. (1989).
Sparrow, J. R., et al. The retinal pigment epithelium in health and disease. Curr. Mol Med. 10, 802-823 (2010).
Stark et al., Synaptic and Extrasynaptic NMDA Receptors Differentially Modulate Neuronal Cyclooxygenase-2 Function, Lipid Peroxidation, and Neuroprotection. The Journal of Neuroscience. 2011; 31(39):13710-21.
Strauss, O. The retinal pigment epithelium in visual function. Physiol Rev. 85, 845-881 (2005).
Thundyil, J. et al. Adiponectin receptor signalling in the brain. Br. J. Pharmacal 165, 313-327 (2012).
Wattier, S., Kelly, M. Nehls, M. Construction of gene targeting vectors from lambda KOS genomic libraries. Biotechniques 26, 1150-1156 (1999).
Wu, C. et al. BioGPS: an extensible and customizable portal for querying and organizing gene annotation resources. Genome Biol. 10, R130 (2009).
Yamamoto, H. et al. Mutations in the gene encoding 11 cis retinol dehydrogenase cause delayed dark adaptation and fundus albipunctatus. Nat. Genet. 22, 188-191 (1999).
Yamauchi, T. et al. Adiponectin receptor as a key player in healthy longevity and obesity-related diseases. Cell Metab. 17, 185-196 (2013).
Yamauchi, T. et al. Cloning of adiponectin receptors that mediate antidiabetic metabolic effects. Nature 423, 762-769 (2003).
Zambrowicz, B. P. et al. Disruption and sequence identification of 2,000 genes in mouse embryonic stern cells. Nature. 392, 608-611 (1998).
Zambrowicz, B. P. et al. W nk1 kinase deficiency lowers blood pressure in mice: a gene-trap screen to identify potential targets for therapeutic intervention. Proc. Natl. Acad. Sci. USA 100, 14109-14114 (2003).
Zhou and Sheng, NMDA receptors in nervous system diseases. Neuropharmacology. 2013; 74:69-75.
Zhou, Y. et al. Cellular and 3D optical coherence tomography assessment during the initiation and progression of retinal degeneration in the Ccl2/Cx3cr1-delicient mouse. Exp. Eye Res. 93, 636-648 (2011).
"Pharmaceutical dosage form tablets", eds. Liberman et al. (New York, Marcel Dekker, Inc., 1989.
"Pharmaceutical dosage forms and drug delivery systems", 6th Edition, Ansel et al., Media, PA: Williams and Wilkins, 1995.
A. Gennaro (2000) "Remington: The Science and Practice of Pharmacy," 20th edition, Lippincott, Williams, & Wilkins.
Agbaga, M. P. et al. Mutant ELOVL4 that causes autosomal dominant stargardt-3 macular dystrophy is rnisrouted to rod outer segment disks. Invest OphthalmoL Vis. Sci. 55, 3669-3680 (2014).
Agbaga, M. P. et al. Role of Stargardt-3 macular dystrophy protein (ELOVL4) in the biosynthesis of very long chain fatty acids. Proc. Natl Acad. Sci. USA 105, 12843-12848 (2008).
Ansel Introduction to Pharmaceutical Dosage Forms, Forth Edition, 1985.
Aveldano, M. I. A novel group of very long chain polyenoic fatty acids in dipolyunsaturated phosphatidylcholines from vertebrate retina. J. Bioi. Chern. 262, 1172-1179 (1987).
Aveldano, M. I. et al. Molecular species of phosphatidylcholine, -ethanolamine, -serine, and -inositol in microsomal and photoreceptor me.about.pbranes of bovine retina. J. Lipid Res. 24, 620-627 (1983).
Aveldano, M. I. Phospholipid species containing long and very long polyenoic fatty acids remain with rhodopsin after hexane extraction of photoreceptor membranes. Biochemistry 27, 1229-1239 (1988).
Barabas, P. et al. Role of ELOVL4 and very long-chain polyunsaturated fatty acids in mouse models of Stargardt type 3 retinal degeneration. Pro c. Nat/ Acad. Sci. USA No. 5181-5186 (2013).

(56) References Cited

OTHER PUBLICATIONS

Bazan et al., Novel aspirin-triggered neuroprotection D1 attenuates cerebral ischemic injury after experimental stroke. Exp Neurol. 2012; 236(1): 122-30.
Bazan, N. G. et al. Docosahexaenoic acid (22:6, n-3) is metabolized to lipoxygenase reaction products in the retina. Biochem. Biophys. Res. Commun. 125, 741-747 (1984).
Bazan, N. G., et al. Docosahexaenoic acid signalolipidomics in nutrition: significance in aging, neuroinflammation, macu1u degeneration, Alzheimer's, and other neurodegenerative diseases. Annu. Rev. Nutr. 31, 321-351 (2011).
Belayev et al., Translational Stroke Research (2011).
Bennett et al., Effect of Reduced Retinal VLC-PUFA on Rod and Cone Photoreceptors Retinal VLC-PUFA in Rod and Cone Photoreceptors. Investigative Ophthalmology & Visual Science. 2014; 55(5):3150-7.
Brush et al., Retinal Sphingolipids and Their Very-Long-Chain Fatty Acid-Containing Species. Investigative Ophthalmology & Visual Science. 2010; 51(9):4422-31.
Buchwald et al. (1980) Surgery 88:507.
Calandria, J, M. et al. Ataxin-1 poly(Q)-induced proteotoxic stress and apoptosis are attenuated in neural cells by docosahexaenoic acid-derived neuroprotectin DI. J. Bioi. Chern. 287, 23726-23739 (2012).
Calandria, J. M. et al. Selective survival rescue in 15-lipoxygenase-1-deficient retinal pigment epithelial cells by the novel docosahexaenoic acid-derived mediator, neuroprotectin DI. J. Bioi. Chern. 284, 17877-17882 (2009).
Dunn, K. C., et al. ARPE-19, a human retinal pigment epithelial cell line with differentiated properties. Exp. Eye Res. 62, 155-169 (1996).
Fliesler, S. J. et al. Chemistry and metabolism of lipids in the vertebrate retina. Prog. Lipid Res. 22, 79-131 (1983).
Gonzalez-Fernandez, F. et al. 11-cis retinol dehydrogenase mutations as a major cause of the congenital night—blindness disorder known as fundus albipunctatus. MoL Vis. 5, 41 (1999).
Gordon, W. C. et al. Retinal pigment epithelial cells play a central role in the conservation of docosahexaenoic acid by photoreceptor cells after shedding and phagocytosis. Curr. Eye Res. 11, 73-83 (1992).
Gordon. W. C. et al. Docosahexaenoic acid utilization during rod photoreceptor cell renewal. J, Neurosci. 10, 2190-2202 (1990).
Handbook of Pharmaceutical Excipients (2000) A.H. Kibbe et al., eds., 3rd ed. Amer. Pharmaceutical Assoc.
Harkewicz et al., Essential Role of ELOVL4 protein in Very Long Chain Fatty Acid Synthesis and Retinal Function. J Biol Chem. 2012; 287(14):11469-80.
Holland, W. L. et al. Receptor-mediated activation of ceramidase activity initiates the pleiotropic actions of adiponectin. Nat. Med. 17, 55-63 (2011).
International Search Report for PCT/US2016/017112 dated Apr. 21, 2016.
IUPAC-IUB Commission on Biochemical Nomenclature. (1972) Biochem. 11:942-944.
Iwabu, M. et al. Adiponectin and AdipoRI regulate PGC-1alpha and mitochondria by Ca(2+) and AMPK/SIRTI. Nature 464, 1313-1319 (2010).
Kaarniranta, K. et al. Adiponectin receptor 1 gene (ADIPOR1) variant is associated with advanced age-related mar:ular degeneration in Finnish population. Neurosci. Lett. 513, 233-237 (2012).
Kanan, Y., et al. Neuroprotectin D1 is synthesized in the cone photoreceptor cell line 661 Wand elicits protection against light-induced stress. Cell. Mol. Neurobiol. 35, 197-204 (2015).
Karan, G. et al. Loss of ER retention and sequestration of the wild-type ELOVL4 by Stargardt disease dominant negative mutants. MoL Vis. 11, 657-664 (2005).
Kihara A. Very long-chain fatty acids: elongation, physiology and related disorders. Journal of Biochemistry. 2012; 152 (5):387-95.
Knott, E. J. et al. Spatial correlation of mouse photoreceptor-RPE thickness between SD-OCT and histology. Exp. Eye Res. 92, 155-160 (2011).
Langer (1990). Science 249: 1527-1533.
Lin, T. et al. Expression of adiponectin and its receptors in type 1 diabetes mellitus in human and mouse retinas. Mol. Vis. 19, 1769-1778 (2013).
Liu et al. Role of long-chain and very-long-chain polyunsaturated fatty acids in macular degenerations and dystrophies. Clinical Lipidology. 2011; 6(5): 593-613.
Liu, A., et al. Long-chain and very long-chain polyunsaturated fatty acids in ocular aging and age-related macular degeneration. J. Lipid Res. 51, 3217-3229 (2010).
Logan et al., Deciphering mutant ELOVL4 activity in autosomal-dominant Stargardt macular dystrophy. Proc Natl Acad Sci USA. 2013; 11(14):5446-51.
Ma, K. et al. Increased .beta.-oxidation but no insulin resistance or glucose intolerance in mice lacking adiponectin. J. Bioi. Chern. 277, 34658-34661 (2002).
Mao, X. et al. APPL1 binds to adiponectin receptors and mediates adiponectin signalling and function. Nat. Cell Biol. 8, 516-523 (2006).
Mattson and Bazan, Apoptosis and necrosis. In Basic Neurochemistry, 7th edition, G. Siegel, R.W. Albers, S.T. Brady, D.L. Price, eds, 2005.
McMahon, A. et al. Stargardt disease-3 mutation in the mouse Elovl4 gene causes retinal deficiency of C32-C36 acyl phosphatidylcholines. FEBS Lett. 581, 5459-5463 (2007).
Mukherjee, P. K. et al. Neuroprotectin D1: a docosahexaenoic acid-derived docosatriene protects human retinal pigment. epithelial cells from oxidative stress. Proc. Nat. Acad. Sci. USA 101, 8491-8496 (2004).
Mukherjee, P. K. et al. Nueurotrophins enhance retinal pigment epithelial cell survival through neuroprotectin D1 signaling. Proc. Natl. Acad. Sci. USA 104, 13152-13157 (2007).
Nguyen, L. N. et al. Mfsd2a is a transporter for the essential omega-3 fatty acid docosahexaenoic acid. Nature 509, 503-506 (2014).
O'Gorman, S. et al. Protarnine-Cre recombinase transgenes efficiently recombine target sequences in the male germ line of mice, but not in embryonic stem cells. Proc. Natl. Acad. Sci. USA 94, 14602-14607 (1997).
Okuda, A. et al. Hetero-oligomeric interactions of an ELOVL4 mutant protein: implications in the molecular rnechairisrn of Stargardt-3 macular dystrophy. Mol. Vis. 16, 2438-2445 (2010).
Olson et al., Rom2-dependent Phosphorylation of Elo2 Controls the Abundance of Very Long-chain Fatty Acids. Journal of Biological Chemistry. 2015; 290(7):4238-47.

* cited by examiner

A

DHA

C

C32:6

B

NPD1

D

C34:6

E

ELV1-Na

G

ELV2-Na

F

ELV1-Me

H

ELV2-Me

COMPOUNDS, COMPOSITIONS, AND METHODS FOR THE TREATMENT OF INFLAMMATORY, DEGENERATIVE, AND NEURODEGENERATIVE DISEASES

CROSS REFERENCE TO RELATED APPLICATIONS

This application is a continuation of U.S. patent application Ser. No. 16/859,791 filed on Apr. 27, 2020, which is a divisional of U.S. patent application Ser. No. 15/549,676 filed on Aug. 9, 2017, which is a U.S. National Stage Application of PCT Patent Application No. PCT/US2016/017112 filed on Feb. 9, 2016, which claims the benefit of U.S. Provisional Application No. 62/113,893, filed Feb. 9, 2015, and of U.S. Provisional Application No. 62/120,229, filed Feb. 24, 2015, the entire contents of each of which are incorporated by reference in their entireties.

STATEMENT REGARDING FEDERALLY SPONSORED RESEARCH OR DEVELOPMENT

This invention was made with government support under R01 EY005121 and P30 GM103340 awarded by the National Institutes of Health. The government has certain rights in the invention.

FIELD OF THE DISCLOSURE

This disclosure relates to previously unknown compounds, compositions, and methods of use for the prevention and treatment of inflammatory, degenerative, and neurodegenerative diseases, including related conditions or disorders. More specifically, this disclosure relates to compounds related to very-long-chain polyunsaturated fatty acids and their hydroxylated derivatives, and their use as therapeutic agents. In particular, this disclosure relates to the treatment of stroke and other brain conditions involving neurodegeneration, as well as retinal degenerative diseases and related conditions causing loss of sight or blindness.

BACKGROUND OF THE DISCLOSURE

Inflammatory, degenerative, and neurodegenerative diseases include a large number of diseases that affect a very large number of people worldwide. In most cases, these diseases and related conditions and disorders are difficult to treat, and remain as an unmet medical need.

Inflammatory diseases in the scope of this disclosure include acute and chronic disorders were homeostasis is disrupted by abnormal or dysregulated inflammatory response. These conditions are initiated and mediated by a number of inflammatory factors, including oxidative stress, chemokines, cytokines, breakage of blood/tissue barriers, autoimmune diseases, genetic factors being gene susceptibility, polymorphisms or inherited conditions, or other conditions that engage leukocytes, monocytes/macrophages or parenchymal cells that induce excessive amounts of pro-cell injury, pro-inflammatory/disruptors of cellular and/or organ homeostasis. These diseases occur in a wide range of tissues and organs and are currently treated, by anti-inflammatory agents such as corticosteroids, non-steroidal anti-inflammatory drugs, TNF modulators, COX-2 inhibitors, etc.

Degenerative diseases comprise conditions that involve progressive loss of vital cells and tissues that result in progressive impairment of function, such as loss of cartilage in knees, hip joints or other joints such as in osteoarthritis. Other degenerative diseases engages cellular and intercellular homeostasis perturbations and includes heart disease, atherosclerosis, cancer, diabetes, intestinal bowel disease, osteoporosis, prostatitis, rheumatoid arthritis, etc.

Neurodegenerative diseases include some of the major diseases of the brain, retina, spinal cord and peripheral nerves, whereby a failure upon neuroinflammatory induction leads to a progressive demise of cellular organization including neuronal onset cell death leading to impaired function. These are due to immune or inflammatory disorders and/or inherited conditions or age-related pathologies. They include ischemic stroke, Alzheimer's disease, Parkinson's disease, amyotrophic lateral sclerosis, multiple sclerosis, autism, neuropathic pain, traumatic brain injury, schizophrenia, depression, and retinal degenerative diseases such as age-related macular degeneration, glaucoma, inherited eye diseases such as retinitis pigmentosa, Stargardt disease, Stargardt-like macular dystrophy, etc.

Retinal degenerative diseases are the leading causes of blindness. Retinal degeneration is the deterioration of the retina caused by the progressive and eventual death of the photoreceptor and retinal pigment epithelial cells of the retina. Retinitis pigmentosa affects between 50,000 and 100,000 people in the United States alone, and macular degeneration is the leading cause of vision loss for those aged 55 and older in the United States, affecting more than 10 million people. There are no effective treatments for these and other retinal degenerative diseases.

Despite progress made in understanding the pathophysiology of inflammatory, degenerative, and neurodegenerative diseases, their detailed molecular mechanisms remain to be fully elucidated. Available treatments today are not able to effectively treat these major diseases or to slow-down their onset and progressive impairment of vital functions. For example, in the case of retinal degenerative diseases, the detailed processes involved in the progressive loss of photoreceptor cells remain unknown, and available treatments today are not able to effectively treat these major diseases and prevent loss of sight.

Therefore, there is a major therapeutic void for the prevention, treatment, and overall management of inflammatory, neuroinflammatory, degenerative and neurodegenerative diseases.

BRIEF SUMMARY OF THE DISCLOSURE

This disclosure provides compounds, compositions, and methods of use for the treatment of inflammatory, degenerative, and neurodegenerative diseases.

The provided compounds are related to omega-3 very long chain polyunsaturated fatty acids (n3 VLC-PUFA or VLC-PUFA) with carbon chains containing from 23 to 42 carbons. In some embodiments the provided compounds are chemically modified pharmaceutically acceptable derivatives of VLC-PUFA containing carbon chains from 24 to 36 carbons and include 6 or 5 alternating cis-carbon-carbon double bonds starting at positions ω-3 (omega-3), ω-6, ω-9, ω-12, ω-15 and ω-18. In other embodiments the disclosure provides compounds that are hydroxylated derivatives of VLC-PUFA that contain one to two hydroxyl groups.

While VLC-PUFA containing an even number of carbons ranging from 24 to 42 carbons have been detected in the form of free acids or as components of cellular lipids in mammalian tissues, VLC-PUFA containing an odd number of carbons are not known to exist in nature.

The provided compounds are chemically modified pharmaceutically acceptable derivatives to enhance their chemical and biological stability, and to enable their use in therapeutic applications involving various forms of drug delivery.

The provided compositions are intended for pharmaceutical use and contain various forms of the provided compounds and their pharmaceutically acceptable derivatives, such as the free carboxylic acids or their pharmaceutically acceptable salts, or as their corresponding esters, phospholipid derivatives, or other prodrug derivatives. The compositions also include additional components and formulations to facilitate solubility, bioavailability, and stability.

The provided methods of treatment involve the use of the compounds or compositions of the disclosure, which contain a therapeutically effective amount of a provided compound in one of several chemically modified forms, including the free carboxylic acids or their pharmaceutically acceptable salts, or as their corresponding esters, their phospholipid derivatives, or other prodrug derivatives.

The provided compounds, compositions, and methods of use are able to restore homeostasis and induce survival signaling in certain cells undergoing oxidative stress or other homeostatic disruptions. Administration of a pharmaceutical composition containing a provided compound restores the homeostatic cellular balance and promotes the survival of certain cells that are essential for maintaining normal function. The provided compounds, compositions, and methods of use can be utilized for the preventive and therapeutic treatment of inflammatory, degenerative, and neurodegenerative diseases. This provided methods of use target critical steps of the initiation and early progression of these conditions by mimicking the specific biology of intrinsic cellular/organs responses to attain potency, selectivity, devoid of side effects and sustained bioactivity.

In particular, this disclosure provides compounds, compositions, and methods of use for the prevention and treatment of retinal degenerative diseases. The provided compounds and compositions induce the survival of photoreceptors and retinal pigment epithelial cells and protect the retina and the brain. The provided methods involve the use of compounds that induce survival signaling in both the retinal pigment epithelial cells and photoreceptors as well as in brain cells. Moreover this disclosure provides compounds, compositions, and methods of use for the prevention and treatment of stroke and other neurodegenerative diseases, such as epilepsy, traumatic brain damage, and spinal cord injury.

BRIEF DESCRIPTION OF THE DRAWINGS

Further aspects of the present disclosure will be readily appreciated upon review of the detailed description of its various embodiments, described below, when taken in conjunction with the accompanying drawings.

After 2 hours of MCA occlusion, the rats were re-anesthetized temperature probes were reinserted and the intraluminal suture was removed. The neck incision was closed with silk sutures, and the animals were allowed free access to food and water. These results show that the use elovanoids after the ischemic event result in remarkable neuroprotection, suggesting a potential therapeutic benefit for the treatment of ischemic stroke and other neurodegenerative diseases or disorders. The sodium salt ELV2-Na showed a greater potency, presumably because it delivers the active form of ELV2 and has a more immediate effect. The methyl ester ELV2-Me is expected to first be hydrolyzed via the actions of esterases, and it may have a more delayed effect, which may be beneficial for a sustainable long-term treatment. Overall, these data demonstrate the neuroprotective effects of the elovanoids, either as pharmaceutically acceptable salts (e.g. ELV2-Na), or in the form of a prodrug, such as an ester derivative (e.g. ELV2-Me), or as a pharmaceutical composition containing a combination of the two forms that can have both an immediate and a sustainable long-term therapeutic effect.

Figure 13:
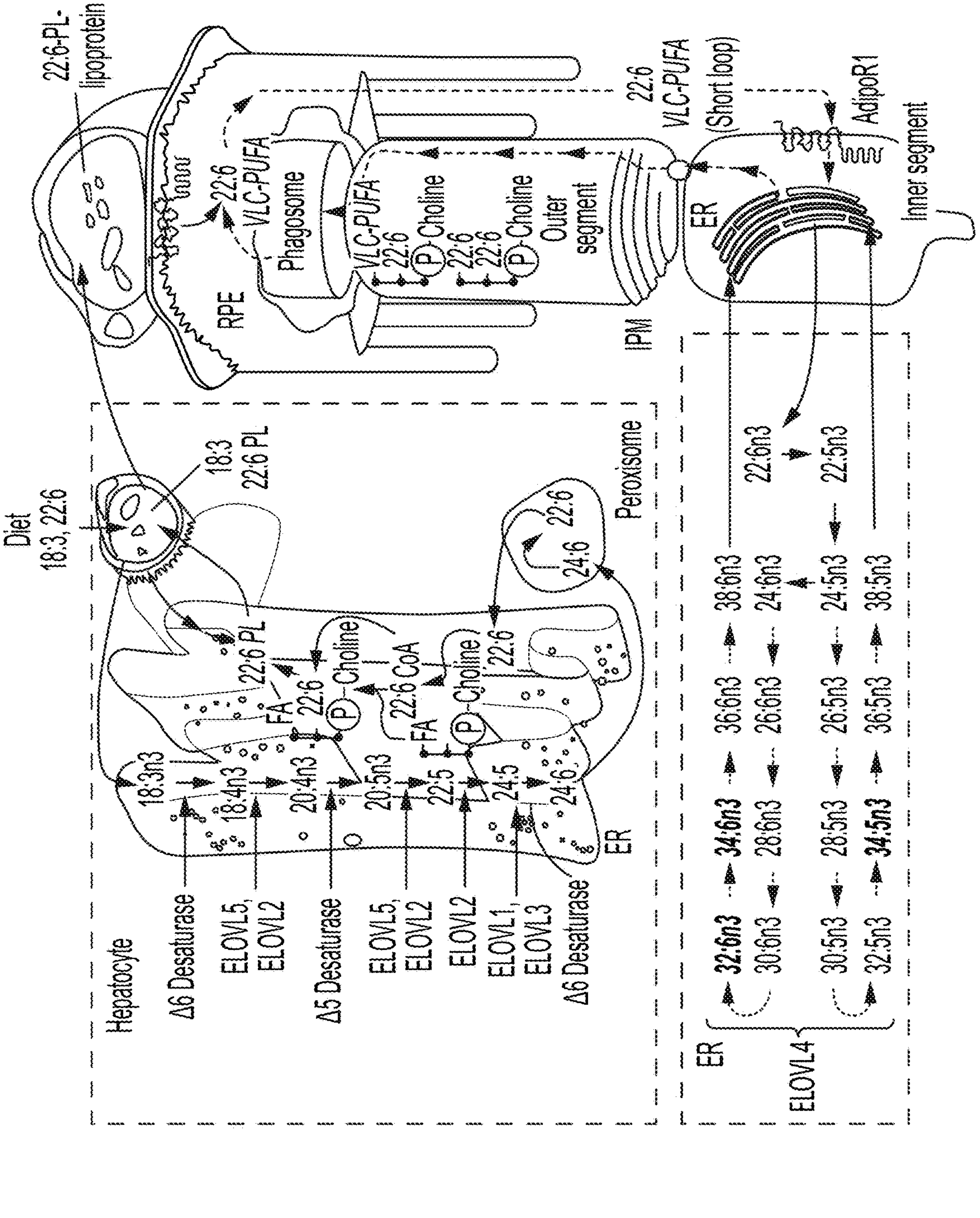

FIG. 13. Role of omega-3 very long chain-polyunsaturated fatty acids (n3-VLC-PUFAs) results in the survival of photoreceptor cells, the protection of the retina, and the prevention of sight loss (Nat. Commun. 2015; 6:1-14). Daily photoreceptor outer segment shed their tips that in turn are taken-up and digested in the phago-lysosomal system of the retinal pigment epithelial cell. Omega-3 fatty acids from outer segment membrane phospholipids are shuttled back to the inner segment of the photoreceptor to be incorporated again into phospholipids for membrane biogenesis of the outer segment. So there is recycling of this essential fatty acid and conservation during a process called photoreceptor outer segment renewal. We postulate that the VLC-PUFAs in the RPE cells directly or upon enzymatic conversion into hydroxylated derivatives, foster integrity of the cell and as result of the photoreceptors. This diagram depicts the desaturation and elongation steps in the generation of VLC-PUFAs as these molecules traffic through the endoplasmic reticulum and the peroxisome of the hepatocyte, the endoplasmic reticulum of the photoreceptor inner segment and into the photoreceptor outer segment. The elongation steps catalyzed by ELOVL4 are highlighted in red. RPE retrieval of DHA (C22:6) and of the VLC-PUFAs from shed photoreceptor apical disk membranes is followed by recycling of DHA and of the VLC-PUFAs back to the photoreceptor inner segment.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, toxicology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Definitions

As used herein, the nomenclature alkyl, alkoxy, carbonyl, etc. is used as is generally understood by those of skill in the chemical art. As used in this specification, alkyl groups can include straight-chained, branched and cyclic alkyl radicals containing up to about 20 carbons, or 1 to 16 carbons, and are straight or branched. Exemplary alkyl groups herein include, but are not limited to, methyl, ethyl, propyl, isopropyl, isobutyl, n-butyl, sec-butyl, tert-butyl, isopentyl, neopentyl, tert-pentyl and isohexyl. As used herein, lower alkyl refer to carbon chains having from about 1 or about 2 carbons up to about 6 carbons. Suitable alkyl groups may be saturated or unsaturated. Further, an alkyl may also be substituted one or more times on one or more carbons with substituents selected from a group consisting of C1-C15 alkyl, allyl, allenyl, alkenyl, C3-C7 heterocycle, aryl, halo, hydroxy, amino, cyano, oxo, thio, alkoxy, formyl, carboxy, carboxamido, phosphoryl, phosphonate, phosphonamido, sulfonyl, alkylsulfonate, arylsulfonate, and sulfonamide. Additionally, an alkyl group may contain up to 10 heteroatoms, in certain embodiments, 1, 2, 3, 4, 5, 6, 7, 8 or 9 heteroatom substituents. Suitable heteroatoms include nitrogen, oxygen, sulfur and phosphorous.

As used herein, “cycloalkyl” refers to a mono- or multicyclic ring system, in certain embodiments of 3 to 10 carbon atoms, in other embodiments of 3 to 6 carbon atoms. The ring systems of the cycloalkyl group may be composed of one ring or two or more rings which may be joined together in a fused, bridged or spiro-connected fashion.

As used herein, “aryl” refers to aromatic monocyclic or multicyclic groups containing from 3 to 16 carbon atoms. As used in this specification, aryl groups are aryl radicals, which may contain up to 10 heteroatoms, in certain embodiments, 1, 2, 3 or 4 heteroatoms. An aryl group may also be optionally substituted one or more times, in certain embodiments, 1 to 3 or 4 times with an aryl group or a lower alkyl group and it may be also fused to other aryl or cycloalkyl rings. Suitable aryl groups include, for example, phenyl, naphthyl, tolyl, imidazolyl, pyridyl, pyrroyl, thienyl, pyrimidyl, thiazolyl and furyl groups.

As used in this specification, a ring is defined as having up to 20 atoms that may include one or more nitrogen, oxygen, sulfur or phosphorous atoms, provided that the ring can have one or more substituents selected from the group consisting of hydrogen, alkyl, allyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, phosphonate, phosphonamido, and sulfonyl, and further provided that the ring may also contain one or more fused rings, including carbocyclic, heterocyclic, aryl or heteroaryl rings.

As used herein, alkenyl and alkynyl carbon chains, if not specified, contain from 2 to 20 carbons, or 2 to 16 carbons, and are straight or branched. Alkenyl carbon chains of from 2 to 20 carbons, in certain embodiments, contain 1 to 8 double bonds, and the alkenyl carbon chains of 2 to 16 carbons, in certain embodiments, contain 1 to 5 double bonds. Alkynyl carbon chains of from 2 to 20 carbons, in certain embodiments, contain 1 to 8 triple bonds, and the alkynyl carbon chains of 2 to 16 carbons, in certain embodiments, contain 1 to 5 triple bonds.

As used herein, “heteroaryl” refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrrolidinyl, pyrimidinyl, tetrazolyl, thienyl, pyridyl, pyrrolyl, N-methylpyrrolyl, quinolinyl and isoquinolinyl.

As used herein, “heterocyclyl” refers to a monocyclic or multicyclic non-aromatic ring system, in one embodiment of 3 to 10 members, in another embodiment of 4 to 7 members, in a further embodiment of 5 to 6 members, where one or more, in certain embodiments, 1 to 3, of the atoms in the ring system is a heteroatom, that is, an element other than carbon, including but not limited to, nitrogen, oxygen or sulfur. In embodiments where the heteroatom(s) is(are) nitrogen, the nitrogen is optionally substituted with alkyl, alkenyl, alkynyl, aryl, heteroaryl, aralkyl, heteroaralkyl, cycloalkyl, heterocyclyl, cycloalkylalkyl, heterocyclylalkyl, acyl, guanidino, or the nitrogen may be quaternized to form an ammonium group where the substituents are selected as above.

As used herein, “aralkyl” refers to an alkyl group in which one of the hydrogen atoms of the alkyl is replaced by an aryl group.

As used herein, “halo”, “halogen” or “halide” refers to F, Cl, Br or I.

As used herein, “haloalkyl” refers to an alkyl group in which one or more of the hydrogen atoms are replaced by halogen. Such groups include, but are not limited to, chloromethyl and trifluoromethyl.

As used herein, “aryloxy” refers to RO—, in which R is aryl, including lower aryl, such as phenyl.

As used herein, “acyl” refers to a —COR group, including for example alkylcarbonyl, cycloalkylcarbonyl, arylcarbonyl, or heteroarylcarbonyls, all of which may be optionally substituted.

As used herein, “ω-3”, “ω-6”, etc. refers to the customary nomenclature of polyunsaturated fatty acids or their derivatives, wherein the position of a double bond (C═C) is at the carbon atom counted from the end of the carbon chain (methyl end) of the fatty acid or fatty acid derivative. For example, “ω-3” means the third carbon atom from the end of the carbon chain of the fatty acid or fatty acid derivative. Similarly, “ω-3”, “ω-6”, etc. also refers to the position of a substituent such as a hydroxyl group (OH) located at a carbon atom of the fatty acid or fatty acid derivative, wherein the number (e.g. 3, 6, etc.) is counted from the end of the carbon chain of the fatty acid or fatty acid derivative.

As used herein, the abbreviations for any protective groups and other compounds, are, unless indicated otherwise, in accord with their common usage, recognized abbreviations, or the IUPAC-IUB Commission on Biochemical Nomenclature (see, (1972) *Biochem.* 11:942-944).

As used herein, wherein in chemical structures of the compounds of the disclosure are shown having a terminal carboxyl group “—COOR” the “R” is intended to designate a group covalently bonded to the carboxyl such as an alkyl group. In the alternative, the carboxyl group is further intended to have a negative charge as “—$COO^+$” and R is a cation including a metal cation, an ammonium cation and the like.

As used herein “subject” is an animal, typically a mammal, including human, such as a patient.

As used herein, “pharmaceutically acceptable derivatives” of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C═C(OR) where R is hydrogen, alkyl, alkenyl, alkynyl, aryl, heteroaryl, aralkyl, heteroaralkyl, cycloalkyl ar heterocyclyl. Pharmaceutically acceptable enol esters include, but are not limited to, derivatives of formula C═C(OC(O)R) where R is hydrogen, alkyl, alkenyl, alkynyl, aryl, heteroaryl, aralkyl, heteroaralkyl, cycloalkyl ar heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, amelioration of the symptoms of a particular disorder by administration of a particular compound or pharmaceutical composition refers to any lessening, whether permanent or temporary, lasting or transient that can be attributed to or associated with administration of the composition.

The term "therapeutically effective amount" as used herein refers to that amount of an embodiment of the composition or pharmaceutical composition being administered that will relieve to some extent one or more of the symptoms of the disease or condition being treated, and/or that amount that will prevent, to some extent, one or more of the symptoms of the condition or disease that the subject being treated has or is at risk of developing. As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient, diluent, carrier and/or adjuvant" as used in the specification and claims includes one and more such excipients, diluents, carriers, and adjuvants.

As used herein, a "pharmaceutical composition" or a "pharmaceutical formulation" is meant to encompass a composition or pharmaceutical composition suitable for administration to a subject, such as a mammal, especially a human and that refers to the combination of an active agent(s), or ingredient with a pharmaceutically acceptable carrier or excipient, making the composition suitable for diagnostic, therapeutic, or preventive use in vitro, in vivo, or ex vivo. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, intravenous, buccal, rectal, parenteral, intraperitoneal, intradermal, intracheal, intramuscular, subcutaneous, inhalational and the like.

The term "administration" refers to introducing a composition of the present disclosure into a subject. One preferred route of administration of the composition is topical administration. However, any route of administration, such as oral, intravenous, subcutaneous, peritoneal, intra-arterial, inhalation, vaginal, rectal, nasal, introduction into the cerebrospinal fluid, or instillation into body compartments can be used.

As used herein, "treatment" and "treating" refer to the management and care of a subject for the purpose of combating a condition, disease or disorder, in any manner in which one or more of the symptoms of a disease or disorder are ameliorated or otherwise beneficially altered. The term is intended to include the full spectrum of treatments for a given condition from which the patient is suffering, such as administration of the active compound for the purpose of: alleviating or relieving symptoms or complications; delaying the progression of the condition, disease or disorder; curing or eliminating the condition, disease or disorder; and/or preventing the condition, disease or disorder, wherein "preventing" or "prevention" is to be understood to refer to the management and care of a patient for the purpose of hindering the development of the condition, disease or disorder, and includes the administration of the active compounds to prevent or reduce the risk of the onset of symptoms or complications. The patient to be treated is preferably a mammal, in particular a human being. Treatment also encompasses any pharmaceutical use of the compositions herein, such as use for treating a disease as provided herein.

Discussion

Inflammatory, degenerative, and neurodegenerative diseases include a large number of diseases that affect a very large number of people worldwide. In most cases, these diseases and related conditions and disorders are difficult to treat, and remain as an unmet medical need.

Inflammatory diseases in the scope of this disclosure include acute and chronic disorders where homeostasis is disrupted by an abnormal or dysregulated inflammatory response. These conditions are initiated and mediated by a number of inflammatory factors, including oxidative stress, chemokines, cytokines, breakage of blood/tissue barriers, autoimmune diseases or other conditions that engage leukocytes, monocytes/macrophages or parenchymal cells that induce excessive amounts of pro-cell injury, pro-inflammatory/disruptors of homeostasis mediators. These diseases occur in a wide range of tissues and organs and are currently treated, by anti-inflammatory agents such as corticosteroids, non-steroidal anti-inflammatory drugs, TNF modulators, COX-2 inhibitors, etc.

Degenerative diseases include conditions that involve progressive loss of vital cells and tissues that result in progressive impairment of function, such as loss of cartilage in knees, hip joints or other joints such as in osteoarthritis. Other degenerative diseases engages cellular and intercellular homeostasis perturbations and includes heart disease, atherosclerosis, cancer, diabetes, intestinal bowel disease, osteoporosis, prostatitis, rheumatoid arthritis, etc.

Neurodegenerative diseases include some of the major diseases of the brain, retina, spinal cord and peripheral nerves, whereby a progressive demise of cellular organization leads to impaired function. These are due to immune or inflammatory disorders and/or to inherited conditions or aging. They include multiple sclerosis, Alzheimer's disease, Parkinson's disease, amyotrophic lateral sclerosis, retina degenerative diseases such as age-related macular degeneration, inherited eye diseases such as retinitis pigmentosa, glaucoma, etc.

Retinal degenerative diseases are the leading causes of blindness that affects very large numbers of people. Retinal degeneration is the deterioration of the retina caused by the progressive and eventual death of the photoreceptor cells of the retina. Examples of common retinal degenerative diseases include retinitis pigmentosa, age-related macular degeneration, and Stargardt disease. Retinitis pigmentosa affects between 50,000 and 100,000 people in the United States alone, and macular degeneration is the leading cause of vision loss for those aged 55 and older in the United States, affecting more than 10 million people. There are no effective treatments for these and other retinal degenerative diseases.

Despite progress made in understanding the pathophysiology of inflammatory and degenerative diseases, the detailed molecular mechanisms involved in the initiation and progression of these conditions remain poorly understood. For retinal degenerative diseases, the detailed molecular mechanisms involved in the progressive loss of photoreceptor cells remain unknown, and available treatments today are not able to effectively treat these major diseases and prevent loss of sight. What is needed is a method for the prevention and treatment of retinal degenerative diseases that ensures the survival of the retina photoreceptor cells.

Available treatments today are not able to effectively treat these major diseases or to slow-down their progressive impairment of vital functions. What is needed is a method that ensures the survival of critical cells undergoing oxidative stress or other homeostatic disruptions. Therefore, there is a major therapeutic void for the management of inflammatory, neuroinflammatory, degenerative and neurodegenerative diseases.

This disclosure provides compounds, compositions and methods for the effective prevention and treatment of inflammatory and degenerative diseases, including neurodegenerative diseases and retinal degenerative diseases. The disclosure is based on new findings regarding the key protective role of certain omega-3 very long chain-polyunsaturated fatty acids (n3 VLC-PUFA) and related hydroxylated derivatives.

In particular, described herein are methods and compounds for the protection of the retina by inducing the survival of photoreceptors. The methods describe herein involve the use of compounds that induce survival signaling in both the retinal pigment epithelial cells and photoreceptors.

Recent investigations have shown that certain polyunsaturated fatty acids (PUFA) are enzymatically converted to bioactive derivatives that play important roles in inflammation and related conditions. Notable among these are the omega-3 (n3) fatty acids containing 22 carbons including eicosapentaenoic acid (EPA or C20:5n3) (20 carbons, 5 double bonds, omega-3), docosapentaenoic acid (DPA or C22:5n3), and especially docosahexaenoic acid (DHA or C22:6n3) (22 carbons, 6 double bonds, omega-3). These PUFA are converted via lipoxygenase-type enzymes to biologically active hydroxylated PUFA derivatives. Most important among these are specific types of hydroxylated derivatives that are generated in certain inflammation-related cells via the action of a lipoxygenase (LO) enzyme (e.g. 15-LO, 12-LO), and result in the formation of mono-, di- or tri-hydroxylated PUFA derivatives with potent actions including anti-inflammatory, pro-resolving, neuroprotective or tissue-protective actions, among others. For example, neuroprotectin D1 (NPD1), a dihydroxy derivative from DHA formed in cells via the enzymatic action of 15-lipoxygenase (15-LO) was shown to have a defined R/S and Z/E stereochemical structure (10R,17S-dihydroxy-docosa-4Z,7Z,11E,13E,15Z,19Z-hexaenoic acid) and a unique biological profile that includes stereoselective potent anti-inflammatory, homeostasis-restoring, pro-resolving, bioactivity. NPD1 has been shown to modulate neuroinflammatory signaling and proteostasis, and to promote nerve regeneration, neuroprotection, and cell survival.

Other important types of omega-3 fatty acids are the omega-3 very-long-chain polyunsaturated fatty acids (n3 VLC-PUFA or VLC-PUFA), which are produced in cells containing elongase enzymes that elongate PUFA with lower number of carbons to VLC-PUFA containing between 24 to 36 carbons. Representative types of VLC-PUFA include C32:6n3 (32 carbons, 6 double bonds, omega-3), C34:6n3, C32:5n3, and C34:5n3, which are biogenically derived through the action of elongase enzymes, particularly ELOVL4 (ELOngation of Very Long chain fatty acids 4). These fatty acids are also acylated in complex lipids including sphingolipids and phospholipids particularly in certain molecular species of phosphatidyl choline. These VLC-PUFA are thought to display functions in membrane organization, and their significance to health is increasingly recognized. The biosynthesis and biological functions of VLC-PUFA have been the subject of a number of recent investigations that have suggested potential roles in certain diseases.

An increasing number of studies have demonstrated the importance of VLC-PUFA in the retina, an integral part of the central nervous system. For example, the autosomal dominant Stargardt-like macular dystrophy (STGD3), a Juvenile-onset retinal degenerative disease is caused by mutations in exon 6 of the ELOVL4 gene that leads to a truncated ELOVL4 protein (a key elongase enzyme) without an endoplasmic reticulum (ER) retention/retrieval signal, resulting in severe decrease in the biosynthesis of VLC-PUFA. Low retinal levels of VLC-PUFA and abnormally low n3/n6 ratios also occur in age-related macular degeneration (AMD) donor eyes as compared to age-matched control eye donors. Recessive ELOVL4 mutations display clinical features of ichthyosis, seizures, mental retardation, and spastic quadriplegia that resembles Sjogren-Larsson syndrome (SLS) with severe neurologic phenotype implying the significance of VLC-PUFA synthesis for the central nervous system and cutaneous development.

VLC-PUFA were found to be incorporated in phospholipids of the photoreceptor outer membrane, and were shown to play important roles in the longevity of photoreceptors, and in their synaptic function and neuronal connectivity. Therefore, bioactive derivatives based on VLC-PUFA, which are able to prevent the apoptosis of photoreceptor cells may provide therapeutic benefits for various types of retinal degenerative diseases, including Stargardt-like macular dystrophy (STGD3), and X-linked juvenile retinoschisis (XLRS) an inherited early onset retinal degenerative disease caused by mutations in the RS1 gene, which is the leading cause of juvenile macular degeneration in males. This condition denotes a significant photoreceptor synaptic impairment for which there is no available treatment Although VLC-PUFA are attracting increasing attention, their detailed biological role and functional significance remains poorly understood, and their potential use in medicine has not been fully appreciated. In particular, the detailed role and potential beneficial use of VLC-PUFA and their synthetic derivatives as potential therapeutics remains to be established. Moreover, the potential use of VLC-PUFA in inflammatory, degenerative diseases, and neurodegenerative diseases of the retina and the brain, such as stroke, Alzheimer's disease, autism spectrum disorders, schizophrenia, Parkinson's disease, remains to be developed.

The structures, properties, and potential effects of VLC-PUFA in cells and tissues, such as the retina, where they are known to play dominant roles were evaluated. Experiments were done using human retinal pigment epithelial (RPE) cells, which are neuroectoderm-derived post-mitotic cells of the retina, an integral part of the central nervous system. These cells are richly endowed with a multitude of mechanisms to protect themselves from injury and to protect other cells, particularly the survival of photoreceptors. They are the most active phagocyte of the human body, critical for the health of photoreceptors and vision, and have the ability to secrete neurotrophins and other beneficial substances. In pathological conditions they recapitulate aspects of Alzheimer's disease by processing amyloid precursor protein and contributing to the formation of Drusen, analogously to the senile amyloid plaques. Thus, these are among the reasons that some of the experimental data included in this disclosure were obtained with RPE cells. Therefore, the data provided herein are representative of the expected activities of the provided compounds in other cells and tissues where VLC-PUFA are known to be generated or be present. Based on the data detailed herein, we postulate that VLC-PUFA are expressed in certain forms of these cells, and in a paracrine fashion they induce the expression of protective phonotypes of these cells. These cells appear between the RPE and the photoreceptors, a zone of immune privilege regulated by immunosuppressive RPE signals and other factors.

There is a growing evidence that a reduced presence of VLC-PUFA in certain cells and tissues is associated with degenerative, neurodegenerative, and retinal degenerative diseases, which are linked to excessive and persistent inflammatory environment.

The naturally occurring VLC-PUFA are biosynthesized via the actions of elongase enzymes, such as ELOVL4, which add two carbons at a time starting from DHA (which has 22 carbon atoms), as summarized in FIG. 13. Thus, biogenetically derived VLC-PUFA contain only an even number of carbons ranging from 24 of up to 42 carbons. Such naturally occurring VLC-PUFA have been detected in the form of free acids or as components of cellular lipids in mammalian tissues. Due to the requirement of elongase enzymes in their biosynthesis, VLC-PUFA containing an odd number of carbons are not known to exist in nature.

This disclosure was conceived on the hypothesis that therapeutic interventions for these VLC-PUFA related diseases can be developed by providing pharmacologically effective amounts of compounds that mimic the structures and biological activities of locally generated VLC-PUFA. While there are several VLC-PUFA fatty acids that have been identified in cells and tissues, their biological roles have been presumed to be due to these naturally generated fatty acids and the corresponding phospholipids.

Figure 2:
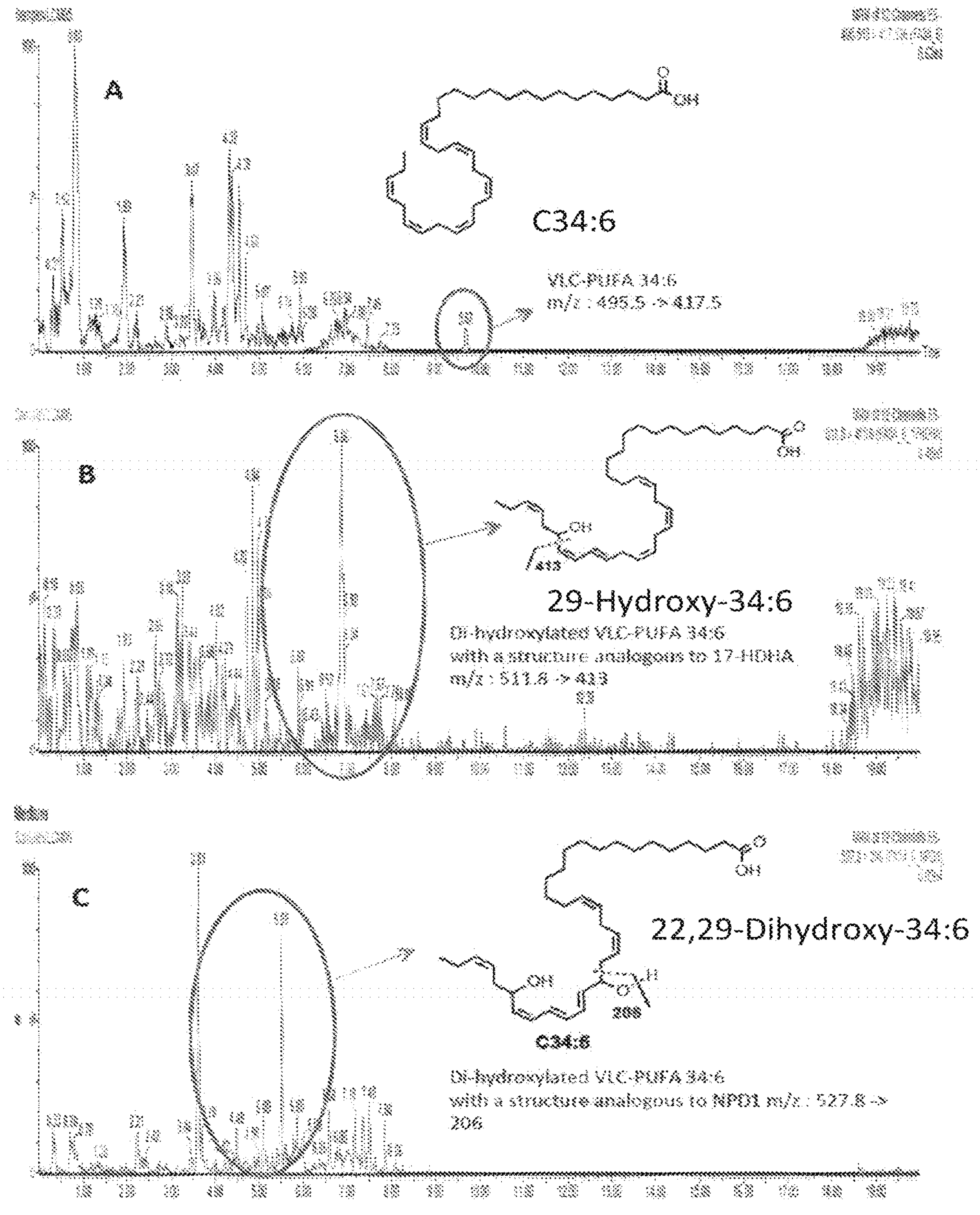
FIG. 2. Evidence of cell-derived hydroxylated derivatives (29-hydroxy-34:6 and 22,29-dihydroxy-34:6) derived from the omega-3 VLC-PUFA 34:6n3 (C34:6) from human retinal pigment epithelial cells in culture. Human retinal pigment epithelial cells (spontaneously transformed ARPE-19 cells) or primary human retinal pigment epithelial cells (HRPE) were incubated with 34:6n3 (100 nM) during 12-16 hours and then the culture media collected lipid extracted and run in LC-MS/MS. The results suggest that C34:6 with an m/z of 495.5 (FIG. 2A) yielded a hydroxylated product analogous to the mono-hydroxylated DHA derivative 17-HDHA having a parent-H m/z of 511.8 and a fragment m/z of 413, which is consistent with the mono-hydroxylated compound 29-hydroxy-34:6 (FIG. 2B). The data show that compound C34:6 was also converted to an elongation product analogous to the di-hydroxylated DHA derivative NPD1,(10R, 17S-dihydroxy-docosa-4Z,7Z,11E,13E,15Z,19Z-hexaenoic acid) having a parent-H m/z of 527.8, and a fragment m/z of 206 consistent with the NPD1-like di-hydroxylated compound 22,29-dihydroxy-34:6 (FIG. 2C).

In this disclosure we describe for the first time compounds having carbon chains analogous to VLC-PUFA that in addition to having 6 or 5 C═C bonds, they also contain one or two hydroxyl groups. Based on the hypothesis that compounds of this type may be responsible for the protective and neuroprotective actions of VLC-PUFA, we sought to identify their existence in human retinal pigment epithelial cells in culture in the presence of a VLC-PUFA added in its fatty acid form. As shown in FIG. 2, we had obtained evidence of the formation of mono-hydroxy and di-hydroxy VLC-PUFA derivatives with molecular structures that are analogous to DHA-derived 17-hydroxy-DHA and the di-hydroxy compound NPD1 (10R, 17S-dihydroxy-docosa-4Z, 7Z,11E,13E,15Z,19Z-hexaenoic acid). Given the very small (nanogram) quantities of these hydroxylated derivatives of VLC-PUFA, it was not possible to identify their complete structure and stereochemistry (R or S hydroxy groups, Z or E double bonds). Moreover, the detected compounds were not identified from tissues naturally occurring in nature, but from the result of an artificial experiment combining a human cell and a VLC-PUFA. Therefore, the natural occurrence of the provided mono- and di-hydroxylated is not known at this time.

The provided compounds are not obtained from natural sources but they are prepared by adapting methods known in the art, starting with commercially available materials. The provided preparation methods were designed to be suitable to the unique hydrophobic properties of VLC-PUFA, which differ significantly from compounds having a total number of carbons of 22 carbons or less.

The provided compounds are chemically modified pharmaceutically acceptable derivatives to enhance their chemical and biological stability, and to enable their use in therapeutic applications involving various forms of drug delivery.

Rather than provide VLC-PUFA in the form occurring in nature, this disclosure provides compounds that have stereochemically pure structures and are chemically synthesized and modified to have additional structural features and properties that enable them to exert pharmacological activity. The disclosure also provides pharmacologically effective compositions of the provided compounds that enhance their ability to be delivered to a subject in a manner that can reach the targeted cells and tissues.

It is currently known that:(a) Mutations in the elongase enzyme ELVOL4 leads to retinal degenerative diseases; (b) ELOVL4 is a key enzyme involved in the conversion of DHA (C22:6) into VLC-PUFA; (c) Genetic ablation of the protein that is necessary to capture DHA into retinal cells containing ELOVL4 products result in a drastically decreased levels of the VLC-PUFAs with consequent retinal degeneration; and (d) Oxidative stress (OS) is associated with the early stages of degenerative, neurodegenerative, and retinal degenerative diseases.

While not wishing to be bound by any one theory, it was considered that VLC-PUFA or their endogenously produced derivatives may play a direct role in neuronal protection and survival, which can provide the basis for a new concept for the treatment of inflammatory, degenerative and neurodegenerative diseases.

The present disclosure is supported by the following new and unexpected data herein disclosed:

(a) VLC-PUFA C32:6 and C34:6 are protective against OS in RPE cells (FIGS. 4, 5, 6, 7, 8, 9, 10).

(b) Protection against OS by VLC-PUFA is not inhibited by inhibitors of the 15 LOX-1 enzyme (FIG. 5A). Since 15 LOX-1 is associated with the conversion of DHA into NPD1, the observed actions of VLC-PUFA suggest that there are different enzymes associated with their protective role.

(c) Cell-derived hydroxylated derivatives (29-hydroxy-34:6 and 22,29-dihydroxy-34:6) could be detected in cultures of VLC-PUFA C34:6 from human retinal pigment epithelial cells in culture (FIG. 2).

Figure 3:
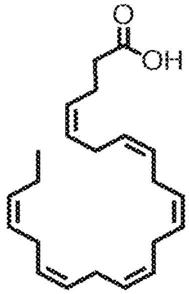
FIG. 3. Structures of compounds: (A) DHA, (B) NPD1, (C) C32:6, (D) C34:6, (E) chemically synthesized ELV1-Na, (F) chemically synthesized ELV1-Me, (G) chemically synthesized ELV2-Na, (F) chemically synthesized ELV2-Me.
Figure 3:
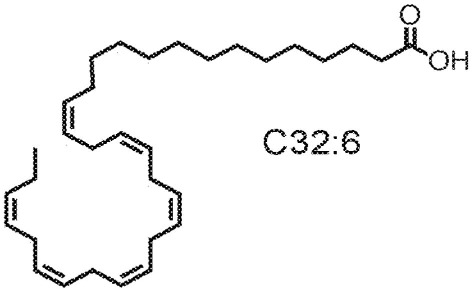
Figure 3:
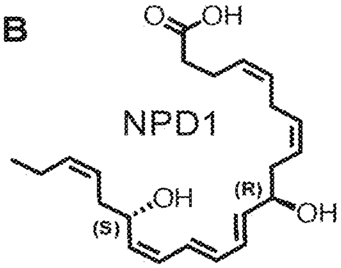
Figure 3:
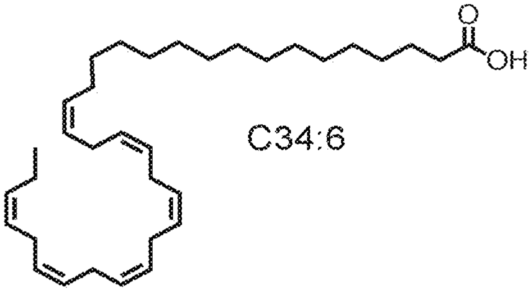
Figure 3:
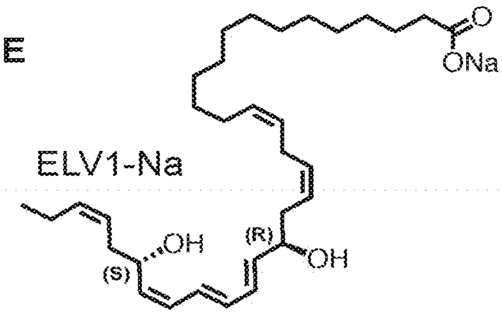
Figure 3:
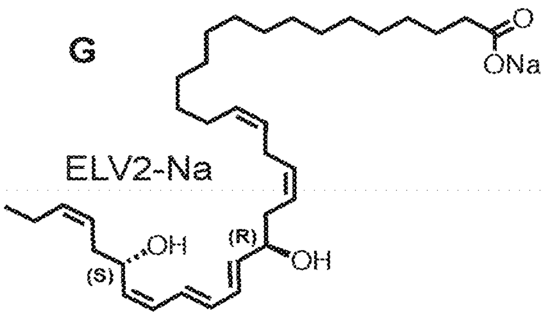
Figure 3:
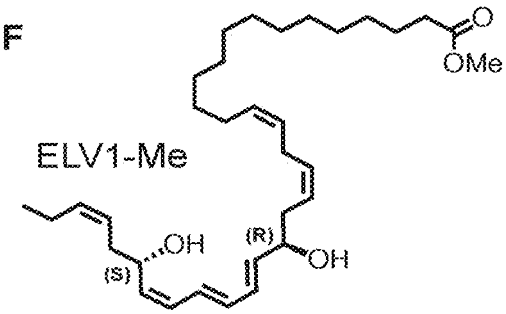
Figure 3:
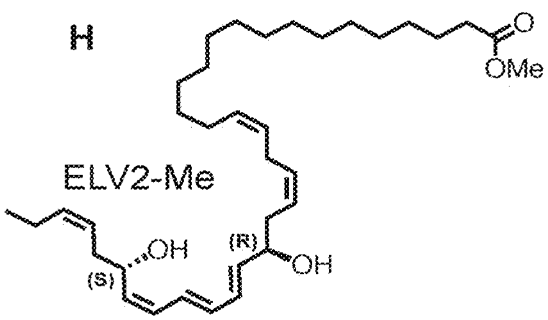

(d) Chemical synthesis afforded stereochemically pure di-hydroxylated derivatives of VLC-PUFA C32:6 and C34:6, named herein as elovanoids ELV1 and ELV2 respectively, prepared as sodium salts or methyl esters (FIG. 3).

Figure 4:
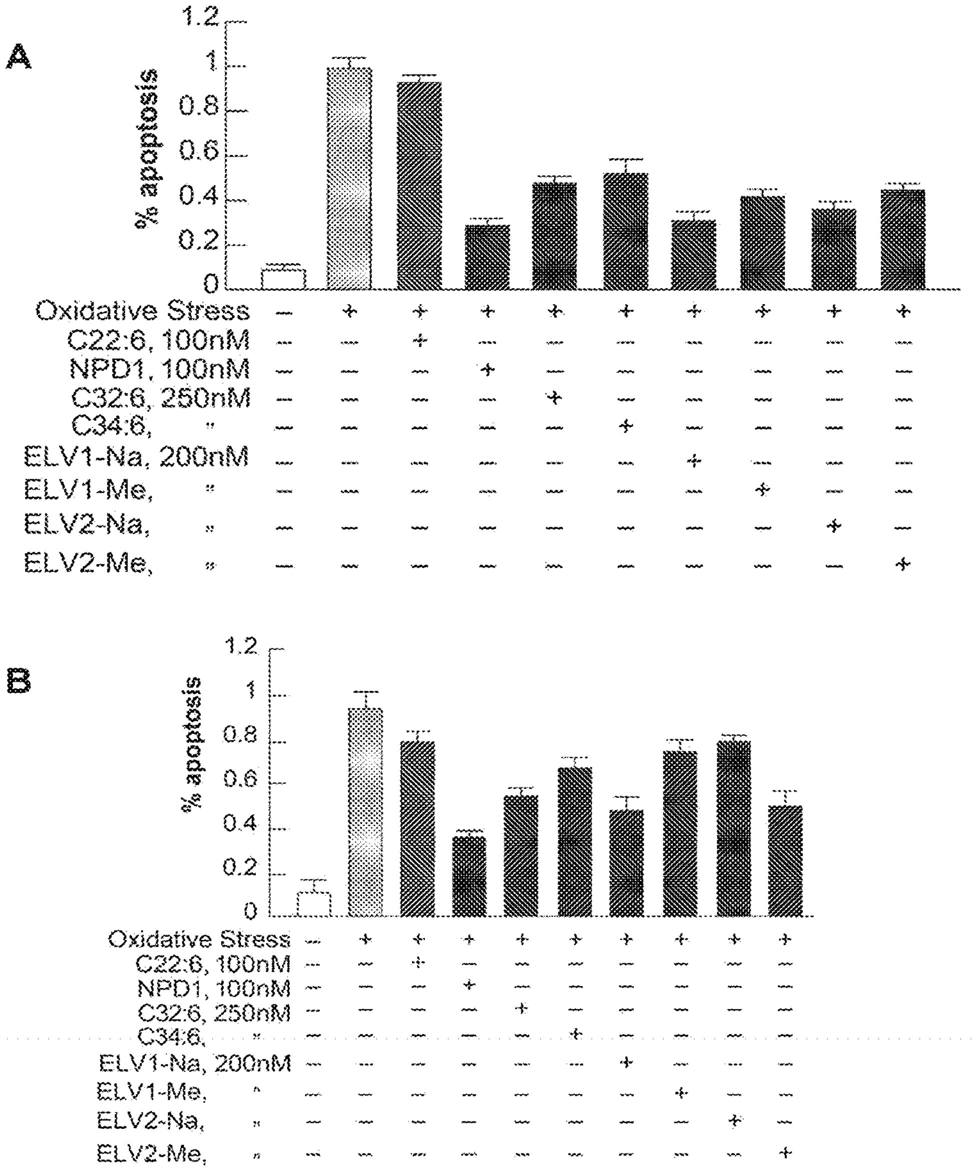
FIG. 4. (A) Cytoprotective effects of NPD1 like compounds on OS induced apoptosis. The results shown in this figure compare the cytoprotective capacities of long chain polyunsaturated fatty acids (VLC-PUFA), elovanoids ELV1 and ELV2, and neuroprotectin D1 (NPD1) in human retinal pigment epithelial (RPE) cells deficient in 15-LOX-D1 by measuring the protection of cell deaths induced by oxidative stress (OS) by these compounds. The results indicate that NPD1 provided the maximum protection (60%), followed by elovanoids at intermediate level (55%), and VLC-PUFA (50%), the least compared to OS (90%). (B) Elovanoid precursors protect human retinal pigment epithelial cells deficient in 15-LOX-1, unlike DHA, from oxidative stress conditions. This experiment clearly shows that VLC-PUFA, elovanoid precursors 32:6 and 34:6, and NPD1 protect against cell death in 15-LOX-D1 cells under oxidative stress conditions. On the other hand, DHA was unable to do so, as the 15-LOX-D1 cells lack the enzyme required for conversion of DHA to the neuroprotective agent.

(e) The synthetic elovanoids ELV1 and ELV2 as sodium salts or methyl esters exhibited more potent activity against OS than the related VLC-PUFA (FIG. 4).

(f) The potent activities of elovanoids ELV1 and ELV2 co-related with potent downregulation of the proapoptotic proteins of the Bcl2 family Bid (FIG. 6), Bim (FIG. 7), Bax (FIG. 8B).

Figure 8:
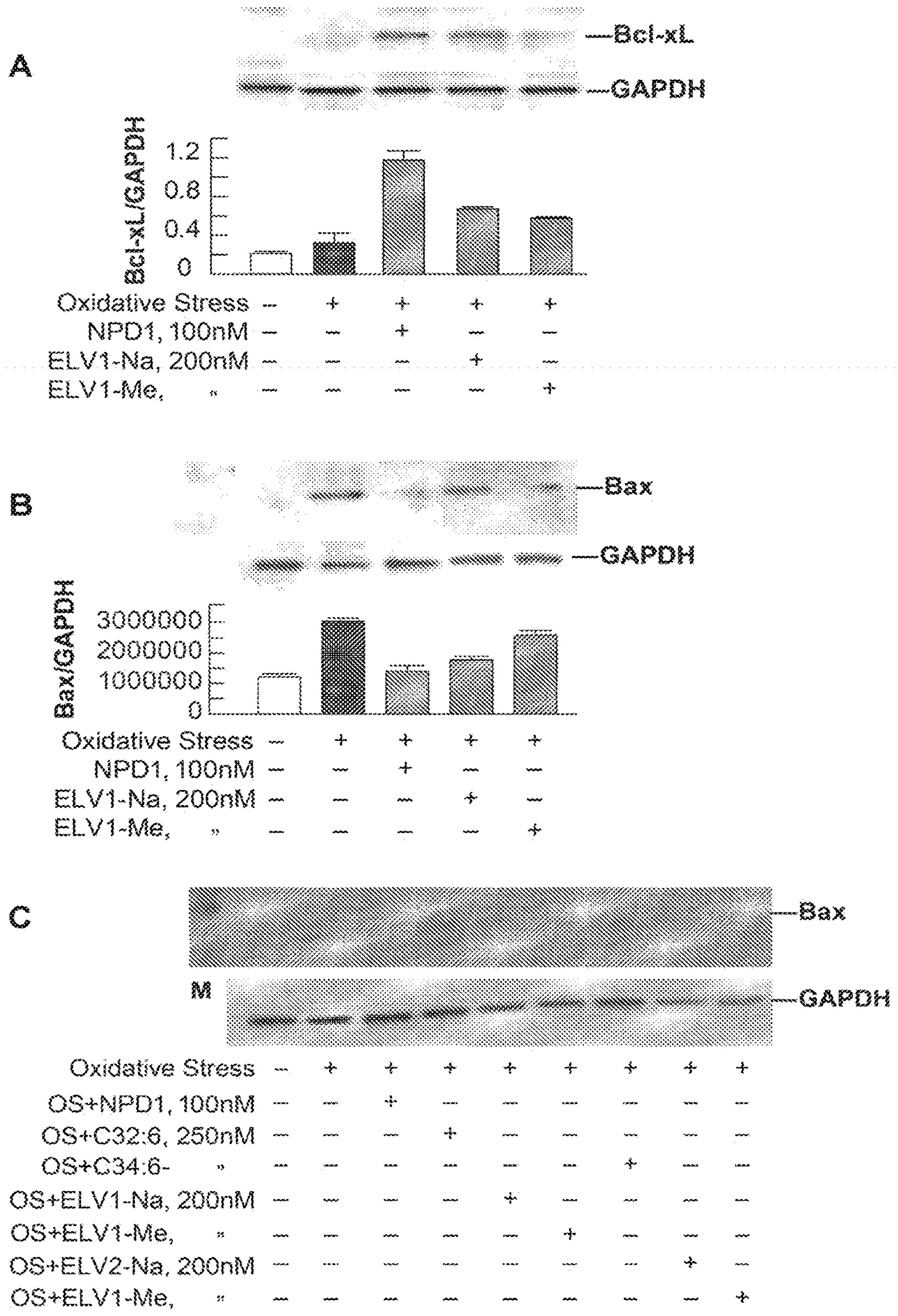
FIG. 8. (A) Bcl-xL-upregulation by elovanoids ELV1 and ELV2 in ARPE-19 cells under stress. Bcl-xL is the antiapoptotic Bcl2 family protein. Like proapoptotic proteins Bid and Bim, the effect of elovaniod precursors on the antiapoptotic protein Bcl-xL was tested in this figure in RPE cells under OS. Results showed that elovaniod precursors were able to upregulate the Bcl-xL protein in RPE cells under stress, which is the opposite effect of Bid and Bim. (B) Effect of NPD1, ELV1 and ELV2 on Bax expression in LOX-D cells under stress. Proapoptotic Bax was tested in this figure. It is evident that elovaniod precursors downregulated the Bax upregulation by OS in RPE cells under OS, which is consistent with our inhibition of apoptosis experiments, as shown before. C) VLC-PUFA and elovanoids ELV1 and ELV2 mediated effect on Bax upregulation in ARPE-19 cells under stress. In this experiment, elovanoid precursors along with VLC-PUFA were tested on the downregulation of the Bax protein in RPE cells under stress.
Figure 9:
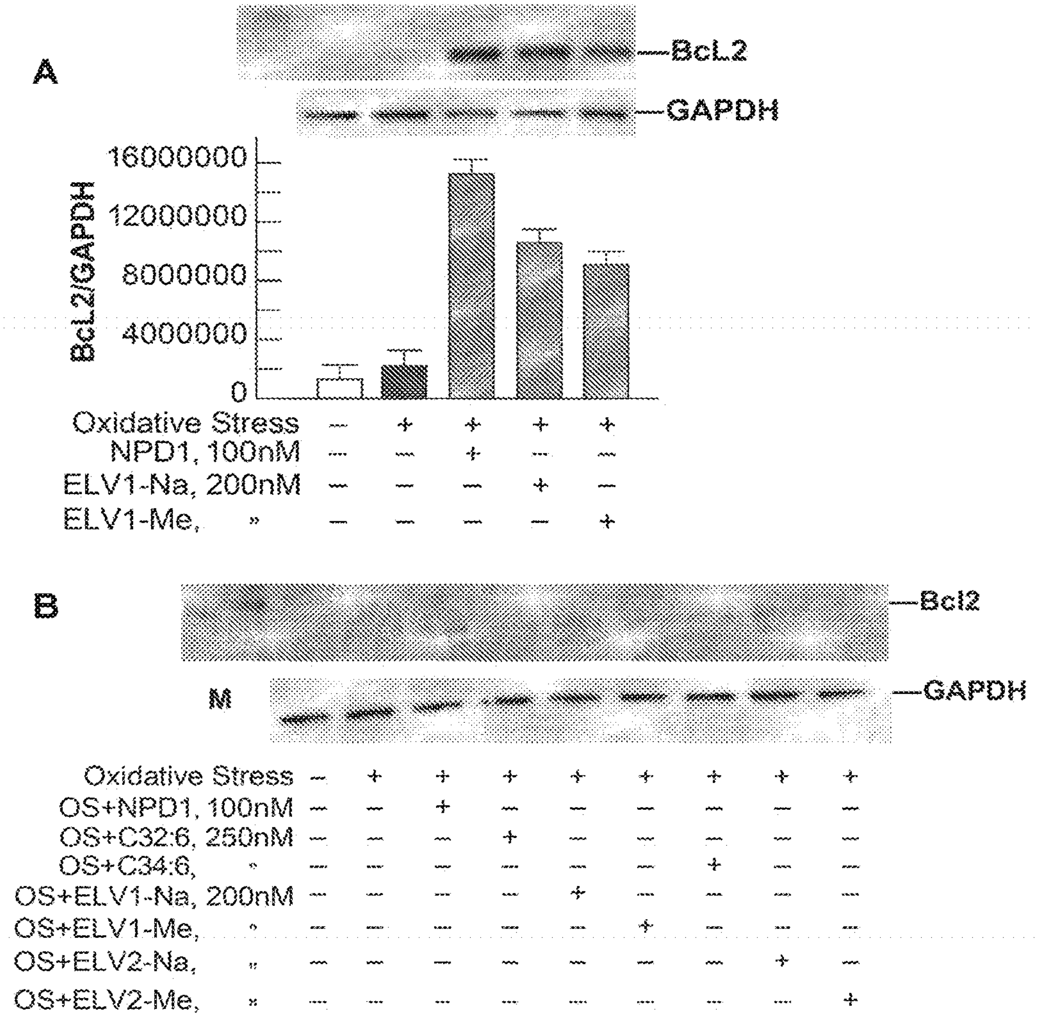
FIG. 9. (A) VLC-PUFA and elovanoids ELV1 and ELV2 mediated effect on Bcl2 upregulation in ARPE-19 cells under stress. In this experiment we tested the effect of elovanoid precursors on Bcl2 upregulation along with VLC-PUFA in stressed RPE. (B) Quantification of Bcl2 upregulation by NPD1, ELV1 and ELV2 in LOX-D cells. Bcl2 is an important antiapoptotic protein of the Bcl2 family protein. It is evident that elovaniod precursors upregulated the Bcl2 protein in RPE cells under stress.

(g) The potent activities of elovanoids ELV1 and ELV2 co-related with potent upregulation of the antiapoptotic proteins of the Bcl2 family Bcl-xL (FIG. 8A) and Bcl2 (FIG. 9).

Figure 10:
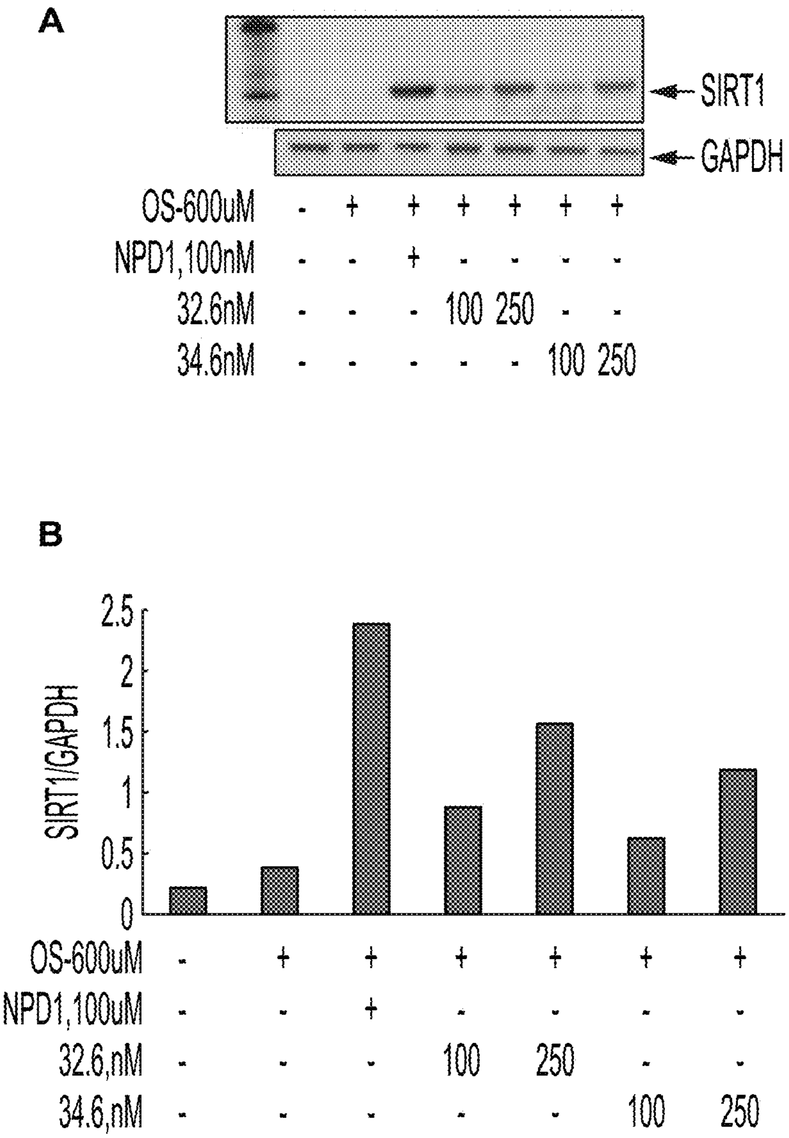
FIG. 10. (A) Effect of NPD1 and VLC-PUFA C32:6 and C34:6 in mediating upregulation of SIRT1 in ARPE-19 cells. (B) Quantification of SIRT1 upregulation by NPD1, C32:6 and C34:6. SIRT1 (Sirtuin1) belongs to a family of highly conserved proteins linked to caloric restriction beneficial outcomes and aging by regulating energy metabolism, genomic stability and stress resistance. SIRT1 is a potential therapeutic target in several diseases including cancer, diabetes, inflammatory disorders, and neurodegenerative diseases or disorders. Elovanoids induce cell survival involving the upregulation of the Bcl2 class of survival proteins and the downregulation of pro-apoptotic Bad and Bax under oxidative stress (OS) in RPE cells. The data in this Figure suggest that elovanoids upregulate SIRT1 abundance in human RPE cells when confronted with OS. As a consequence, remarkable cell survival takes place. This target of elovanoids might be relevant to counteract consequences of several diseases associated with SIRT1.

(h) VLC-PUFA C32:6 and C34:6 mediate the upregulation of SIRT1 in ARPE-19 cells (FIG. 10).

Figure 11:
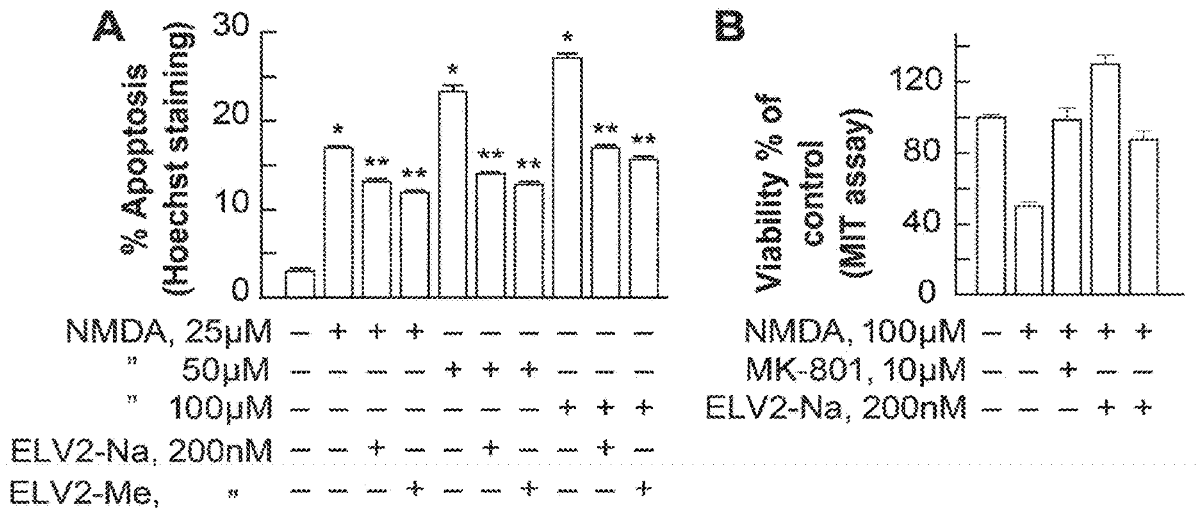
FIG. 11. The elovanoid ELV2 in 200 nM concentrations protects neuronal cells in primary cultures from NMDA-induced toxicity (A), and MK-801 potentiates protection as assessed by MTT assay for cell viability (B). In several neurological and neurodegenerative diseases, such as stroke, epilepsy, status epilepticus, traumatic head injury, etc., as well as ophthalmological diseases, such as glaucoma, an excessive presynaptic release of the excitatory neurotransmitter glutamate takes place. As a consequence, glutamate transporters that function to remove extracellular glutamate from astrocytes and neurons are overwhelmed and the NMDA-type glutamate receptor is over-activated. This receptor is a calcium channel that therefore leads to a flooding of calcium into the postsynaptic cell. The overall phenomena is refer to as excitotoxicity that in turn leads to neuronal damage and cell death. MK801 is a known blocker of this receptor used here as a control. The results in this Figure demonstrate that when NMDA in increasing concentrations is added to neuronal cultures it leads to cell death, while the use of ELV2 reduces cell death and increases cell viability. These data support the use of the elovanoids for the treatment of neurodegenerative diseases and conditions involving NMDA-related excitotoxicity, such as: ischemic stroke, Alzheimer's disease, Parkinson's disease, etc.

(i) The elovanoid ELV2 (as the sodium salt or methyl ester) potently protects neuronal cells in primary cultures from NMDA-induced toxicity (FIG. 11).

Figure 12:
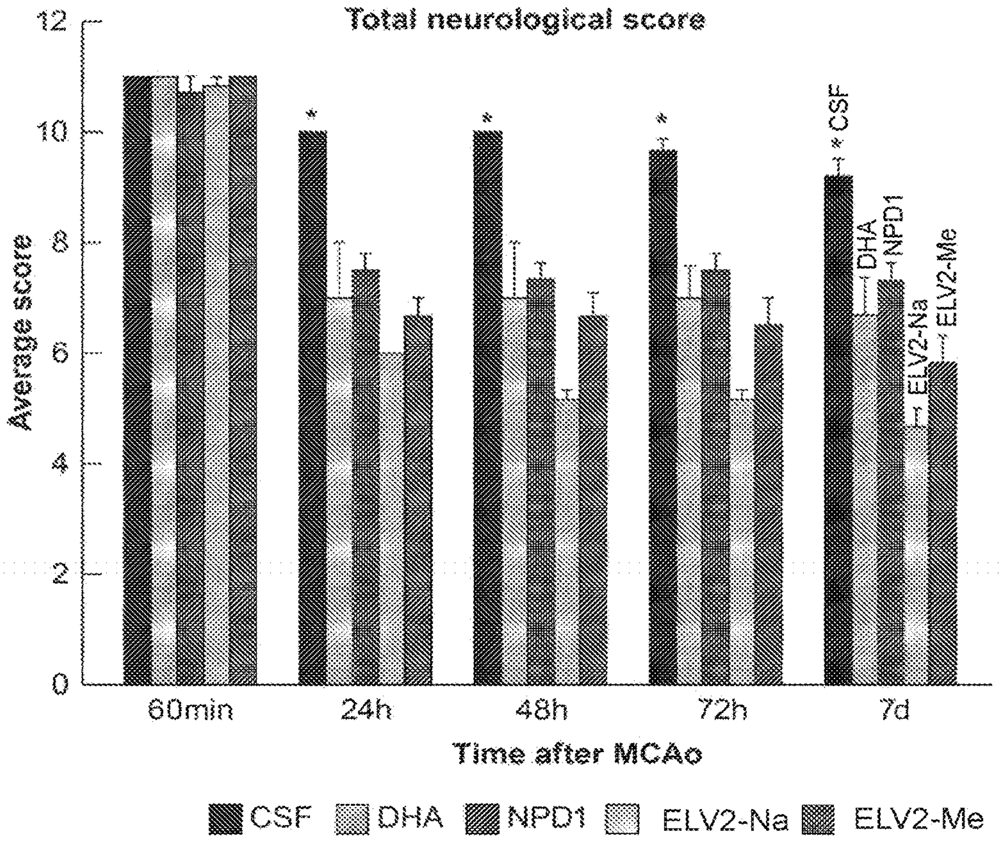
FIG. 12. Elovanoids ELV2-Na and ELV2-Me are more active than DHA and NPD1 in a model of ischemic stroke after 2 hrs of MCAo (middle cerebral occlusion). To test the novel elovanoids the experimental design consisted injecting the compounds into the right cerebral ventricle (5 μg/per rat, ICV), one hour after two hours of an ischemic stroke in rats and following thereafter the neurological behavior (neurological score) during 7 days. The protocol in brief was as follows. The injection was made through a surgically implanted metal canula (Alzet) into the right lateral ventricle. Two days later the right middle cerebral artery (MCA) was occluded for 2 h by means of an intraluminal nylon filament (Belayev et al, Traslational Stroke Research, 2010). Then one hour after the compounds were injected dissolved in sterile cerebrospinal fluid. The occlusion was transient performed as follows. The right common carotid artery was exposed through an incision in the neck and was isolated from surrounding tissues. The distal external carotid artery and pterygopalatine arteries were tied. A 4-cm of 3-0 monofilament nylon suture coated with poly-Lysine was introduced into the internal carotid artery and MCA. The suture position was confirmed by advancing the suture 20-22 mm from the common carotid artery bifurcation. Then, the rats were allowed to awaken from anesthesia and returned to their cages. The degree of stroke injury was assessed by neurological assessment of each rat at 60 min after onset of MCAo. Rats that do not demonstrate high-grade contralateral deficit (score, 10-11) were excluded from the study.

(j) The synthetic elovanoids ELV2-Na and ELV2-Me were shown to have potent in vivo neuroprotective effects in a rat model of ischemic stroke after 2 hours of middle cerebral occlusion (MCAo) (FIG. 12). Both elovanoid derivatives exhibited greater in vivo potency than DHA or NPD1, suggesting a remarkable neuroprotection and a potential therapeutic benefit for the treatment of ischemic stroke and other neurodegenerative diseases or disorders.

(k) The greater potency of elovanoid ELV2 (as sodium salt or methyl ester) vs the docosanoids (DHA, NPD1) (FIG. 12) may be due to either a different mechanism of action, a different metabolic profile that increases their bioavailability, or a different localization (e.g. intracellular receptors in the nuclear membrane) due to their longer fatty acid length and potentially greater hydrophobicity and structural rigidity.

(i) Taken together, the above previously unknown data, including the structure and activity of the elovanoids, and the potent neuroprotective activities of elovanoid derivatives such as ELV1 and ELV2, provide the basis for the present disclosure.

The compounds and compositions provided by this disclosure are able to restore homeostasis and induce survival signaling in certain cells undergoing oxidative stress or other homeostatic disruptions. The disclosure also provides methods of use of the provided compounds and compositions containing a hydroxylated derivative of very long chain polyunsaturated fatty acids, as the free carboxylic acids or their pharmaceutically acceptable salts, or as their corresponding esters or other prodrug derivatives. The provided compounds can be readily prepared by adapting methods known in the art, starting with commercially available materials.

The bioactivity of the provided compounds, as exemplified by the elovanoid derivatives ELV1 and ELV2, is attributed to their ability to reach the targeted human cells and exert their biological actions either by entering into the cell or/and by acting at a membrane bound receptor. Alternatively, the provided compounds can act via intracellular receptors (e.g. nuclear membrane), and thus they would work specifically by affecting key signaling events.

Administration of a pharmaceutical composition, containing a provided compound and a pharmaceutically acceptable carrier, restores the homeostatic balance and promotes the survival of certain cells that are essential for maintaining normal function. The provided compounds, compositions, and methods can be used for the preventive and therapeutic treatment of inflammatory, degenerative, and neurodegenerative diseases. This disclosure targets critical steps of the initiation and early progression of these conditions by mimicking the specific biology of intrinsic cellular/organs responses to attain potency, selectivity, devoid of side effects and sustained bioactivity.

Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Compounds

Described herein are compounds and compositions based on very long chain polyunsaturated fatty acids and their hydroxylated derivatives.

In some embodiments the provided compounds and compositions are based on compounds with the general structures of A or B, wherein n is a number selected from a group consisting of 0 to 19 and the compounds are carboxylic acids or their pharmaceutically acceptable salts. Compounds of structure A are based on very long chain polyunsaturated fatty acids with a total of 23 to 42 carbon atoms in the carbon chain and 6 alternating cis-carbon-carbon double bonds starting at positions ω-3 (omega-3), ω-6, ω-9, ω-12, ω-15 and ω-18. Compounds of structure B are based on very long chain polyunsaturated fatty acids with a total of 23 to 42 carbon atoms in the carbon chain and preferably 5 alternating cis-carbon-carbon double bonds starting at positions ω-3 (omega-3), ω-6, ω-9, ω-12 and ω-15.

A

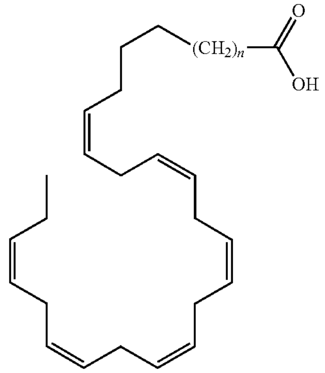

B

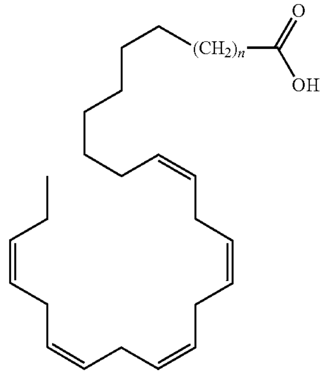

In preferred embodiments, n is a number selected from a group consisting of 0 to 13.

In further preferred embodiments, n is a number selected from 1, 3, 5, 7, 9, 11 or 13, and the fatty acid contains a total of 24, 26, 28, 30, 32, 34 or 36 carbon atoms.

In other preferred embodiments, n is a number selected from a group consisting of 0, 2, 4, 6, 8, 10 or 12, and the fatty acid contains a total of 23, 25, 27, 19, 31, 33 or 35 carbon atoms.

In other embodiments the disclosure provides compounds that are carboxyl derivatives of very long chain polyunsaturated fatty acids of the general structures C or D, wherein n is a number selected from a group consisting of 0 to 19 and the carboxyl derivative is an ester or a pharmaceutically acceptable salt, wherein the R group is selected from a group consisting of methyl, ethyl, alkyl, or a cation selected from a group consisting of: ammonium cation, iminium cation, or a metal cation. Compounds of structure C are ester derivatives of very long chain polyunsaturated fatty acids with a total of 23 to 42 carbon atoms in the carbon chain and preferably 6 alternating cis-carbon-carbon double bonds starting at positions ω-3 (omega-3), ω-6, ω-9, ω-12, ω-15 and ω-18. Compounds of structure D are carboxyl derivatives of very long chain polyunsaturated fatty acids with a total of 24 to 42 carbon atoms in the carbon chain and preferably 5 alternating cis-carbon-carbon double bonds starting at positions ω-3 (omega-3), ω-6, ω-9, ω-12 and ω-15.

C

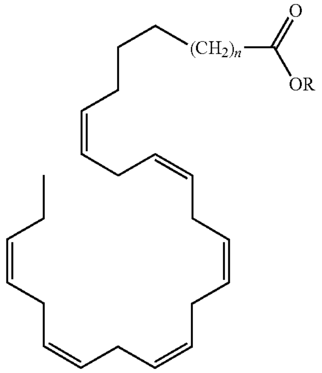

D

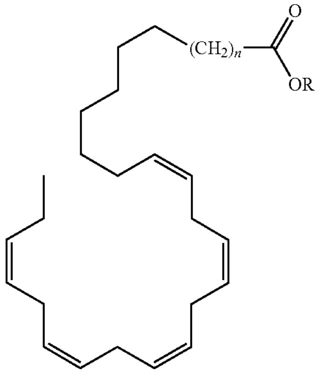

In preferred embodiments, n is a number selected from a group consisting of 0 to 13.

In further preferred embodiments, n is a number selected from 1, 3, 5, 7, 9, 11 or 13, and the fatty acid contains a total of 24, 26, 28, 30, 32, 34 or 36 carbon atoms.

In other preferred embodiments, n is a number selected from a group consisting of 0, 2, 4, 6, 8, 10 or 12, and the fatty acid contains a total of 23, 25, 27, 19, 31, 33 or 35 carbon atoms.

In some preferred embodiments, the R group is methyl or ethyl, or a metal cation selected from a group consisting of sodium, potassium, magnesium, zinc, or calcium cation.

In an exemplary preferred embodiment, the present disclosure provides compounds of the general formula C, wherein:

n is a number selected from a group consisting of zero 1, 3, 5, 7, 9, 11 or 13, wherein the fatty acid chain contains a total of 24, 26, 28, 30, 32, 34 or 36 carbon atoms; and As used herein and in other structures of the present disclosure, the compounds of the disclosure are shown having a terminal carboxyl group "—COOR" the "R" is intended to designate a group covalently bonded to the carboxyl such as an alkyl group. In the alternative, the carboxyl group is further intended to have a negative charge as "—$COO^-$" and R is a cation including a metal cation, an ammonium cation and the like.

R is selected from a group consisting of methyl, ethyl, alkyl, or a cation selected from a group consisting of: ammonium cation, iminium cation, or a metal cation. In some preferred embodiments the metal cation is selected from a group consisting of sodium, potassium, magnesium, zinc or calcium cation.

In some preferred embodiments, the R group is methyl or ethyl, or a metal cation selected from a group consisting of sodium, potassium, magnesium, zinc or calcium cation.

In a further preferred embodiment, the present disclosure provides compounds of the general formula C, wherein:

n is 9 or 11, wherein the fatty acid chain contains a total of 32 or 34 carbon atoms; and R is selected from a group consisting of methyl, ethyl, alkyl, or a cation selected from a group consisting of: ammonium cation, iminium cation, or a metal cation. In some preferred embodiments the metal cation is selected from a group consisting of sodium, potassium, magnesium, zinc, or calcium cation.

In other preferred embodiments, the carboxyl derivative is part of a glycerol-derived phospholipid, wherein R is a glycerol phospholipid that may contain an additional polyunsaturated fatty acid, as exemplified in structures E and F.

E

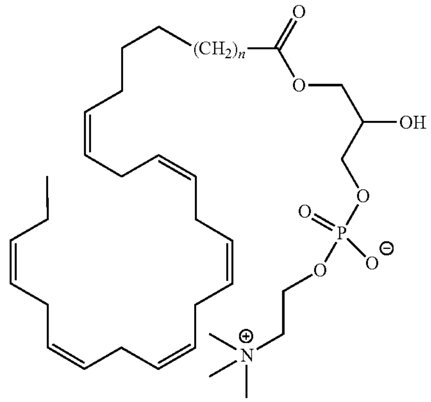

F

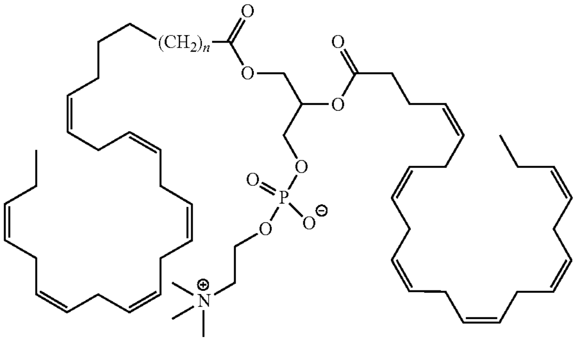

In other embodiments the provided compounds have the general structures of G or H, wherein n is a number selected from a group consisting of 0 to 19, and the carboxylate R group is selected from a group consisting of an ester or a pharmaceutically acceptable salt, wherein the R group is selected from a group consisting of hydrogen, methyl, ethyl, alkyl, or a cation selected from a group consisting of: ammonium cation, iminium cation, or a metal cation. Compounds of structure G are mono-hydroxylated derivatives of very long chain polyunsaturated fatty acids with a total from 23 to 42 carbon atoms in the carbon chain, a hydroxyl group at position ω-6, and with 6 carbon-carbon double bonds starting at positions ω-3, ω-7, ω-9, ω-12, ω-15 and ω-18. Compounds of structure H are mono-hydroxylated derivatives of very long chain polyunsaturated fatty acids with a total from 23 to 42 carbon atoms in the carbon chain, a hydroxyl group at position ω-6, and with 5 carbon-carbon double bonds starting at positions ω-3, ω-7, ω-9, ω-12, and ω-15.

G

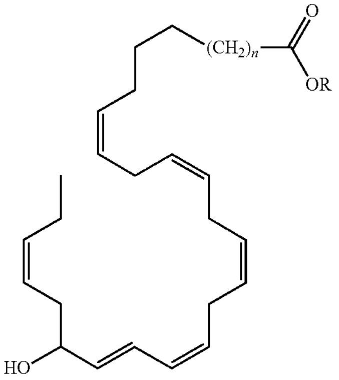

H

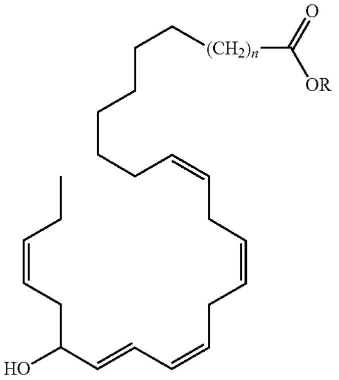

In preferred embodiments, n is a number selected from a group consisting of 1 to 13.

In further preferred embodiments, n is a number selected from 1, 3, 5, 7, 9, 11 or 13, and the fatty acid contains a total of 24, 26, 28, 30, 32, 34 or 36 carbon atoms.

In other preferred embodiments, n is a number selected from a group consisting of 0, 2, 4, 6, 8, 10 or 12, and the fatty acid contains a total of 23, 25, 27, 19, 31, 33 or 35 carbon atoms.

As used herein and in other structures of the present disclosure, the compounds of the disclosure are shown having a terminal carboxyl group "—COOR" the "R" is intended to designate a group covalently bonded to the carboxyl such as an alkyl group. In the alternative, the carboxyl group is further intended to have a negative charge as "—$COO^-$" and R is a cation including a metal cation, an ammonium cation and the like.

R is selected from a group consisting of methyl, ethyl, alkyl, or a cation selected from a group consisting of: ammonium cation, iminium cation, or a metal cation. In some preferred embodiments the metal cation is selected from a group consisting of sodium, potassium, magnesium, zinc or calcium cation.

In some preferred embodiments, the R group is methyl or ethyl, or a metal cation selected from a group consisting of sodium, potassium, magnesium, zinc or calcium cation.

In an exemplary preferred embodiment, the disclosure provides compounds of the general formula G or H, wherein: n is 9 or 11, and the fatty acid chain contains a total of 32 or 34 carbon atoms.

In some preferred embodiments, the provided compounds G and H are predominately one enantiomer with a defined (S) or (R) chirality at the carbon bearing the hydroxyl group.

In an exemplary preferred embodiment, the present disclosure provides a compound selected from a group consisting of I, J, K, or L, having the following structures herein n is 9 or 11, and the fatty acid chain contains a total of 32 or 34 carbon atoms, and the R group is methyl or ethyl, or a metal cation selected from a group consisting of sodium, potassium, magnesium, or calcium cation.

I

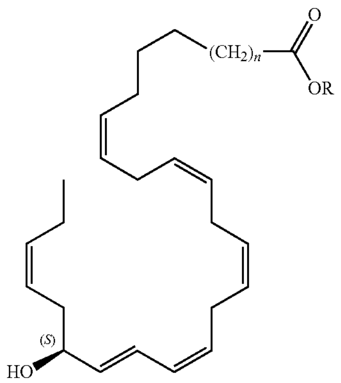

J

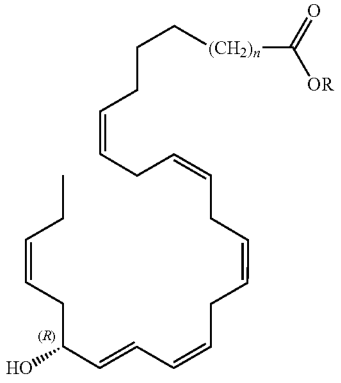

K

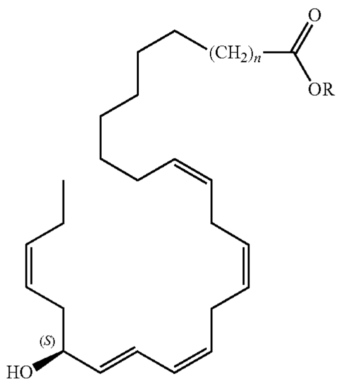

-continued

L

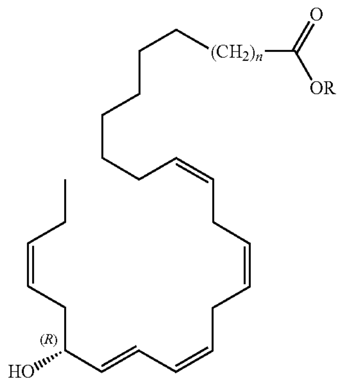

In an exemplary preferred embodiment, the present disclosure provides compound (S, 16Z, 19Z,22Z,25Z,27E, 31Z)-29-hydroxytetratriaconta-16, 19,22,25,27,31-hexaenoic acid (OR═OH), its sodium salt (OR═ONa), or its methyl ester (OR═OMe)

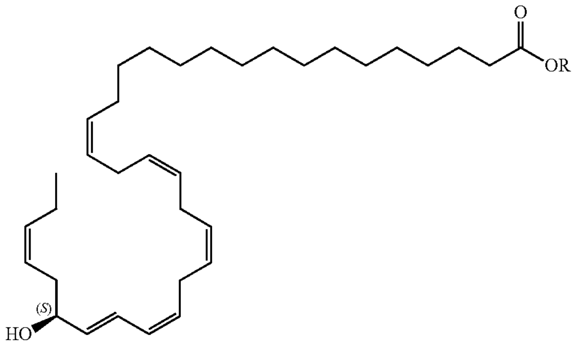

In other embodiments the provided compounds have the general structures of M or N, wherein n is a number selected from a group consisting of 0 to 19, and the carboxylate R group is selected from a group consisting of an ester or a pharmaceutically acceptable salt, wherein the R group is selected from a group consisting of hydrogen, methyl, ethyl, alkyl, or a cation selected from a group consisting of: ammonium cation, iminium cation, or a metal cation. Compounds of structure M are di-hydroxylated derivatives of very long chain polyunsaturated fatty acids with a total from 23 to 42 carbon atoms in the carbon chain, two hydroxyl groups at positions ω-6 and ω-13, and 6 carbon-carbon double bonds at positions ω-3, ω-7, ω-9, ω-11, ω-15 and ω-18. Compounds of structure N are di-hydroxylated derivatives of very long chain polyunsaturated fatty acids with a total from 23 to 42 carbon atoms in the carbon chain, two hydroxyl groups at positions ω-6 and ω-13, and 5 carbon-carbon double bonds at positions ω-3, ω-7, ω-9, ω-11 and ω-15.

M

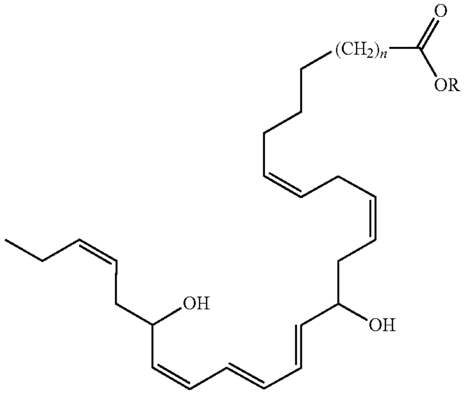

N

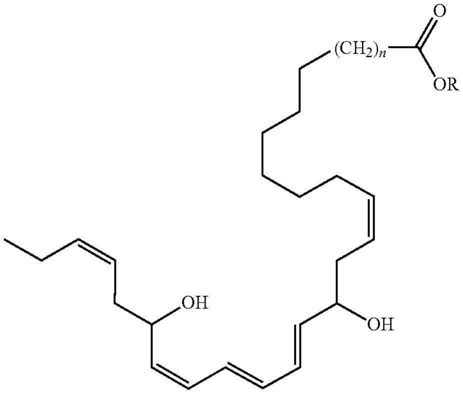

In preferred embodiments, n is a number selected from a group consisting of 1 to 13.

In further preferred embodiments, n is a number selected from 1, 3, 5, 7, 9, 11 or 13, and the fatty acid contains a total of 24, 26, 28, 30, 32, 34 or 36 carbon atoms.

In other preferred embodiments, n is a number selected from a group consisting of 0, 2, 4, 6, 8, 10 or 12, and the fatty acid contains a total of 23, 25, 27, 19, 31, 33 or 35 carbon atoms.

As used herein and in other structures of the present disclosure, the compounds of the disclosure are shown having a terminal carboxyl group "—COOR" the "R" is intended to designate a group covalently bonded to the carboxyl such as an alkyl group. In the alternative, the carboxyl group is further intended to have a negative charge as "—COO$^-$" and R is a cation including a metal cation, an ammonium cation and the like.

R is selected from a group consisting of methyl, ethyl, alkyl, or a cation selected from a group consisting of: ammonium cation, iminium cation, or a metal cation. In some preferred embodiments the metal cation is selected from a group consisting of sodium, potassium, magnesium, zinc or calcium cation.

In some preferred embodiments, the R group is methyl or ethyl, or a metal cation selected from a group consisting of sodium, potassium, magnesium, zinc or calcium cation.

In an exemplary preferred embodiment, the disclosure provides compounds of the general formula M or N, wherein: n is 9 or 11, and the fatty acid chain contains a total of 32 or 34 carbon atoms.

In a preferred embodiment, the present disclosure provides a compound selected from a group consisting of O, P, Q, R, S, T, U or V, having the following structures, wherein n is 9 or 11, and the fatty acid chain contains a total of 32 or 34 carbon atoms, and the R group is methyl or ethyl, or a metal cation selected from a group consisting of sodium, potassium, magnesium, zinc or calcium cation.

O

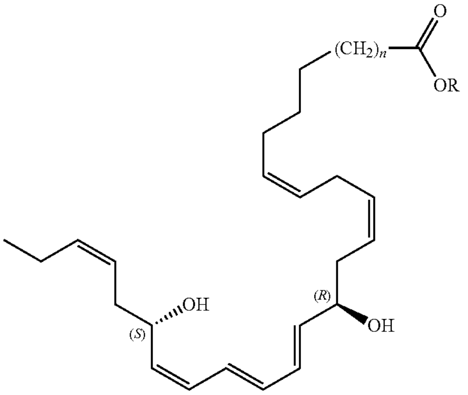

P

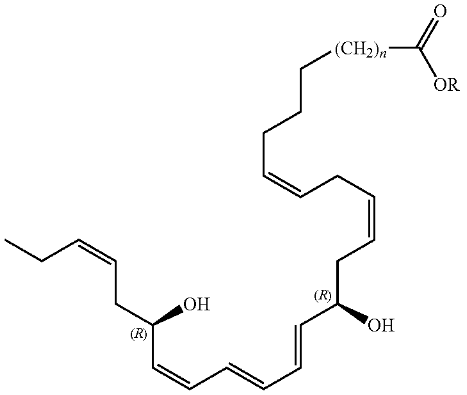

Q

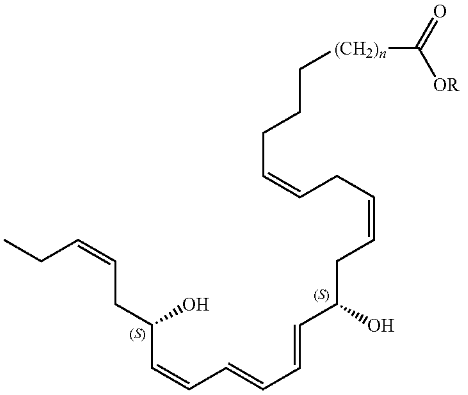

-continued

R

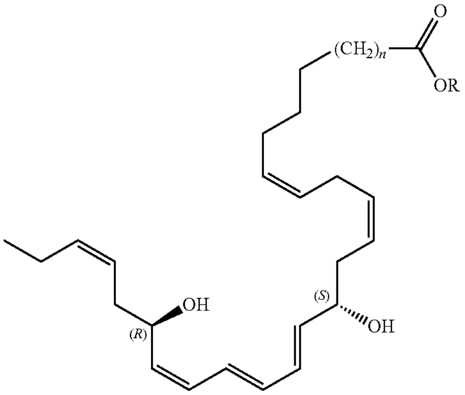

S

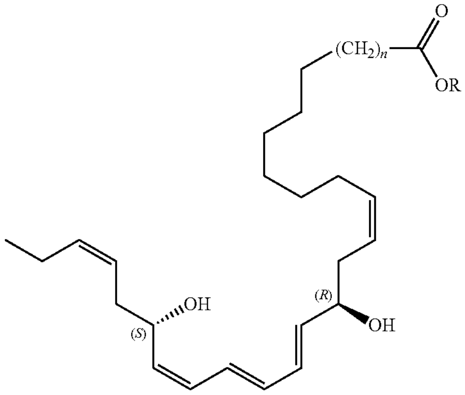

T

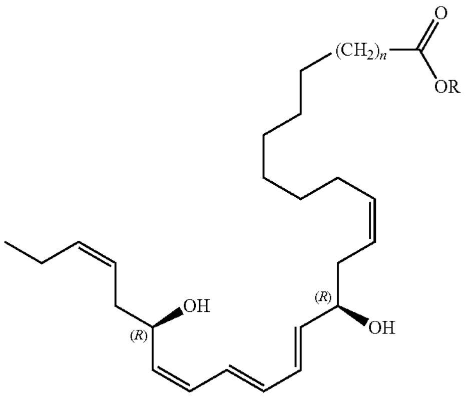

U

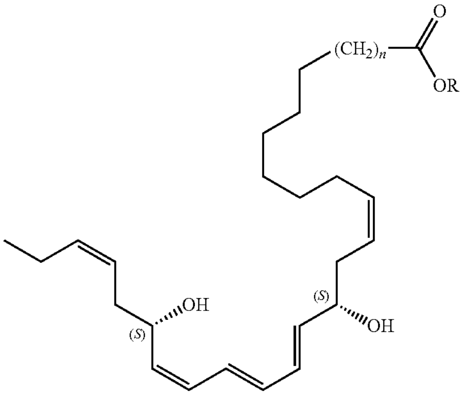

-continued

V

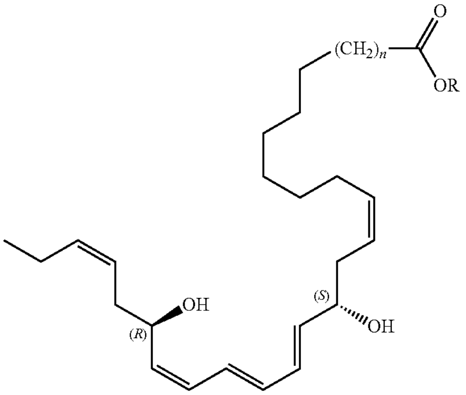

In an exemplary preferred embodiment, the present disclosure provides a compound selected from the group consisting of: (14Z,17Z,20R,21E,23E,25Z,27S,29Z)-20,27-dihydroxydotriaconta-14,17,21,23,25,29-hexaenoic acid; sodium (14Z,17Z,20R,21E,23E, 25Z,27S,29Z)-20,27-dihydroxydotriaconta-14,17,21,23,25,29-hexaenoate; methyl (14Z,17Z, 20R,21E,23E,25Z,27S,29Z)-20,27-dihydroxydotriaconta-14,17,21,23,25,29-hexaenoate; (16Z,19Z,22R, 23E,25E,27Z,29S,31Z)-22,29-dihydroxytetratriaconta-16, 19,23,25,27,31-hexaenoic acid; sodium (16Z,19Z,22R,23E, 25E,27Z,29S,31Z)-22,29-dihydroxytetratriaconta-16,19,23, 25,27,31-hexaenoate; or methyl (16Z,19Z,22R,23E,25E, 27Z,29S,31Z)-22,29-dihydroxy-tetratriaconta-16,19,23,25, 27,31-hexaenoate, which have the following structures:

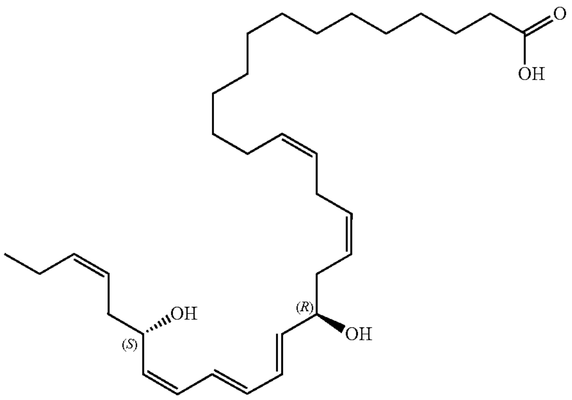

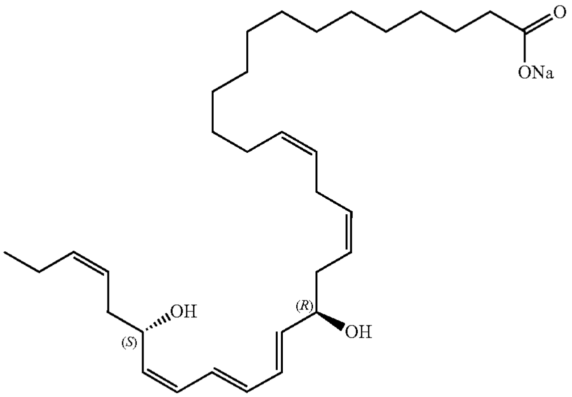

-continued

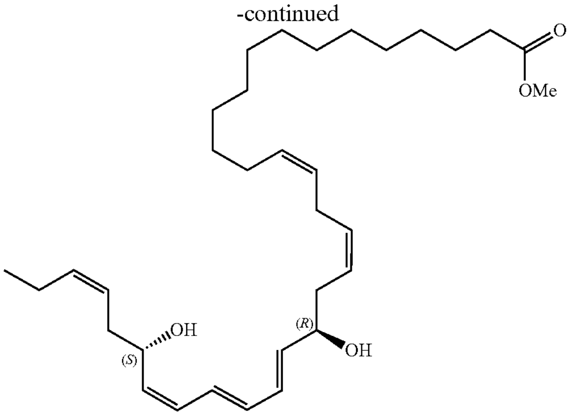

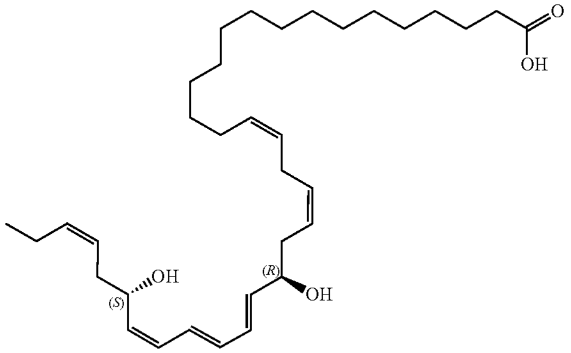

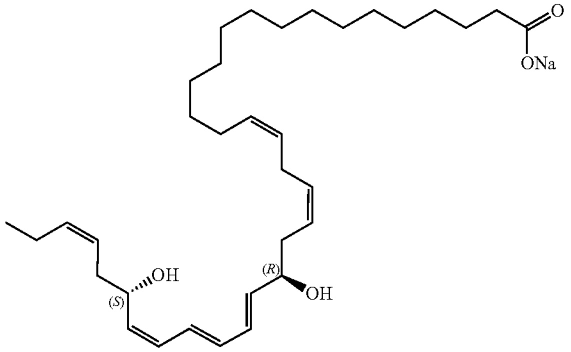

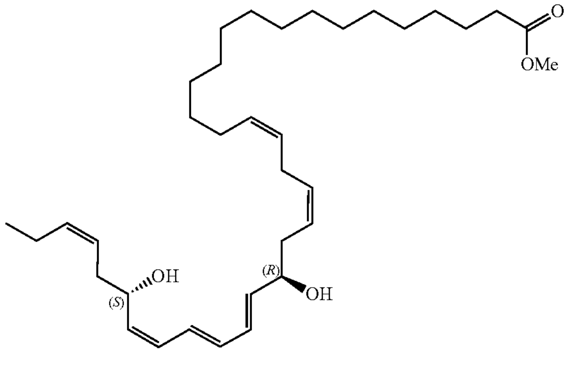

In other embodiments the provided compounds have the general structures of W or Y, wherein n is a number selected from a group consisting of 0 to 19, and the carboxylate R group is selected from a group consisting of an ester or a pharmaceutically acceptable salt, wherein the R group is selected from a group consisting of hydrogen, methyl, ethyl, alkyl, or a cation selected from a group consisting of: ammonium cation, iminium cation, or a metal cation. Compounds of structure M are di-hydroxylated derivatives of very long chain polyunsaturated fatty acids with a total from 23 to 42 carbon atoms in the carbon chain, two hydroxyl groups at positions ω-6 and ω-13, and 6 carbon-carbon double bonds at positions ω-3, ω-7, ω-9, ω-11, ω-15 and ω-18. Compounds of structure N are di-hydroxylated derivatives of very long chain polyunsaturated fatty acids with a total from 23 to 42 carbon atoms in the carbon chain, two hydroxyl groups at positions ω-6 and ω-13, and 5 carbon-carbon double bonds at positions ω-3, ω-7, ω-9, ω-11 and ω-15.

W

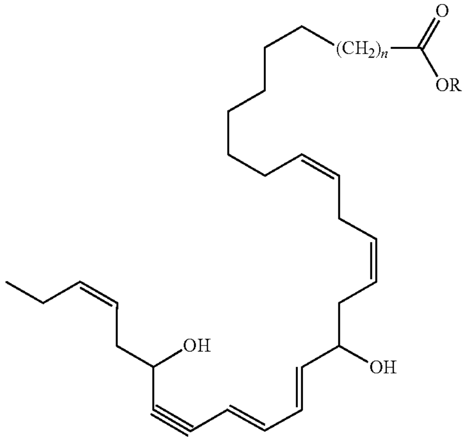

Y

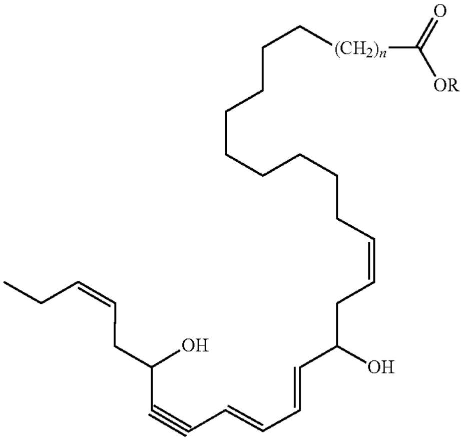

In preferred embodiments, n is a number selected from selected from a group consisting of 1 to 13.

In further preferred embodiments, n is a number selected from 1, 3, 5, 7, 9, 11 or 13, and the fatty acid contains a total of 24, 26, 28, 30, 32, 34 or 36 carbon atoms.

In other preferred embodiments, n is a number selected from a group consisting of 0, 2, 4, 6, 8, 10 or 12, and the fatty acid contains a total of 23, 25, 27, 19, 31, 33 or 35 carbon atoms.

R is selected from a group consisting of methyl, ethyl, alkyl, or a cation selected from a group consisting of: ammonium cation, iminium cation, or a metal cation. In some preferred embodiments the metal cation is selected from a group consisting of sodium, potassium, magnesium, zinc or calcium cation.

In some preferred embodiments, the R group is methyl or ethyl, or a metal cation selected from a group consisting of sodium, potassium, magnesium, zinc or calcium cation.

In an exemplary preferred embodiment, the disclosure provides compounds of the general formula W or Y, wherein: n is 9 or 11, and the fatty acid chain contains a total of 32 or 34 carbon atoms.

In an exemplary preferred embodiment, the present disclosure provides a compound selected from the group consisting of compounds X or Z, wherein R is methyl or sodium:

X

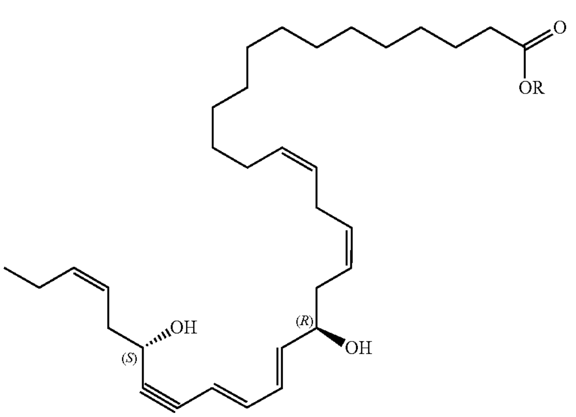

-continued

Z

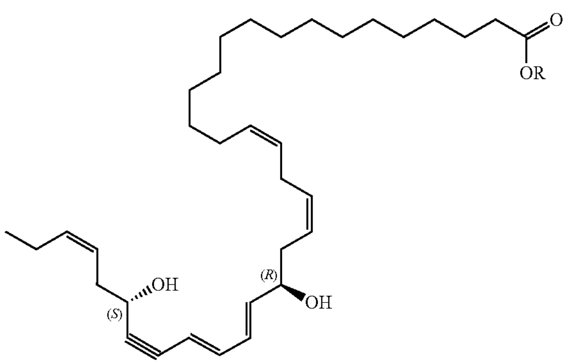

Methods of Preparation and Manufacturing of Provided Compounds

The compounds provided by the present disclosure can be prepared from readily available starting materials. For example, the synthesis of compounds of general structure M can be prepared according to the following general Scheme 1, which exemplifies the method of preparation and manufacturing of the provided compounds of this type.

Scheme 1 shows the detailed approach for the stereocontrolled total synthesis of compounds of type O, wherein n is 9, and the fatty acid chain contains a total of 32 carbon atoms, and the R group is methyl or sodium cation. In particular, Scheme 1 shows the synthesis of compounds ELV1-Me and ELV1-Na, starting with methyl pentadec-14-ynoate (compound 4). By starting with heptadec-16-ynoate, this process affords compounds ELV2-Me and ELV2-Na. The alkynyl precursors of ELV1 and ELV2, namely 13a, 13b, 15a, and 15b are also among the provided compounds X and Z in this disclosure. Scheme 1 provides the key reagents and conditions for the preparations of the provided compounds, by employing reaction conditions that are typical for this type of reactions.

Scheme 1
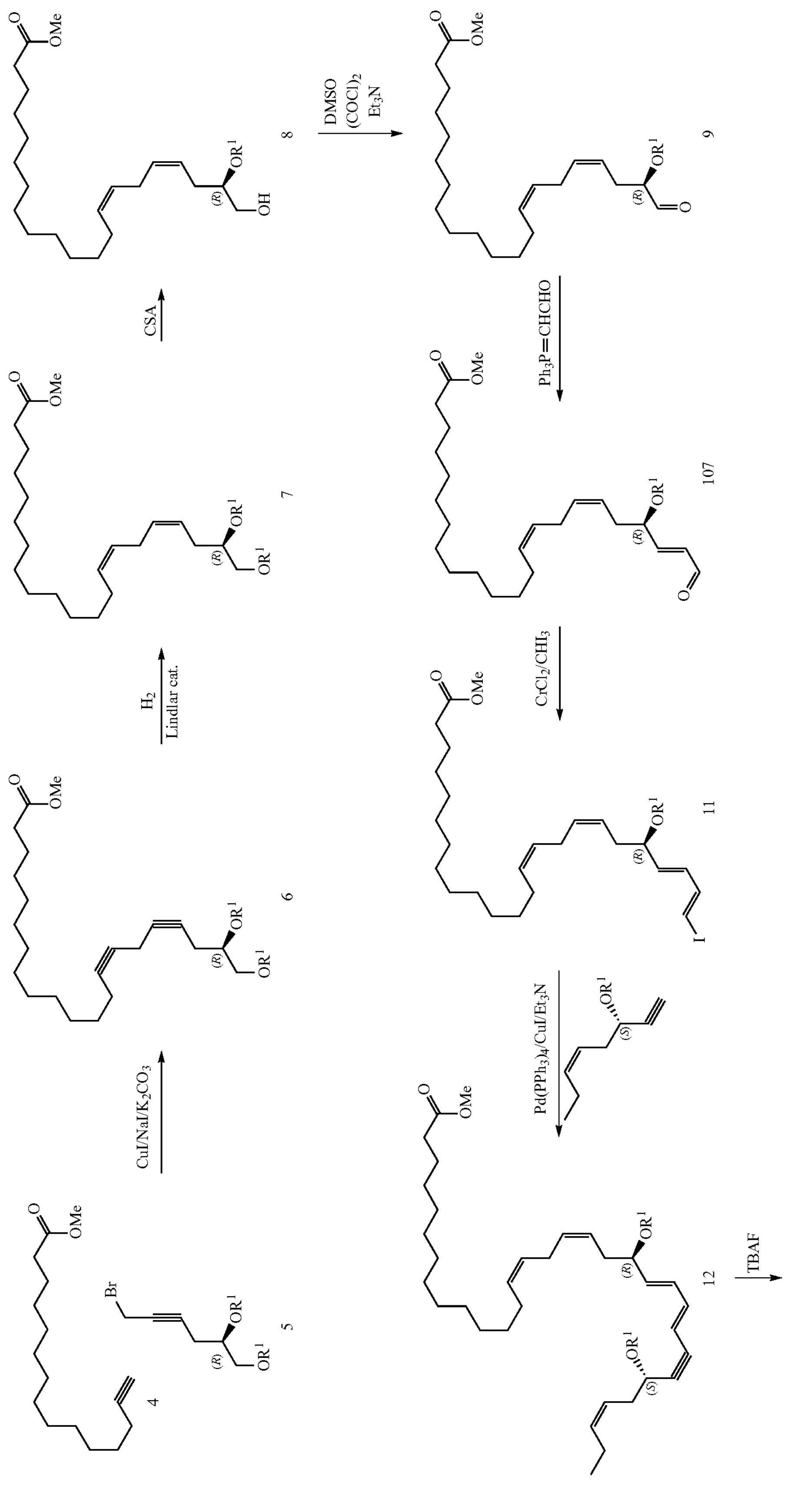
4 5 6 7 8 9 107 11 12

-continued
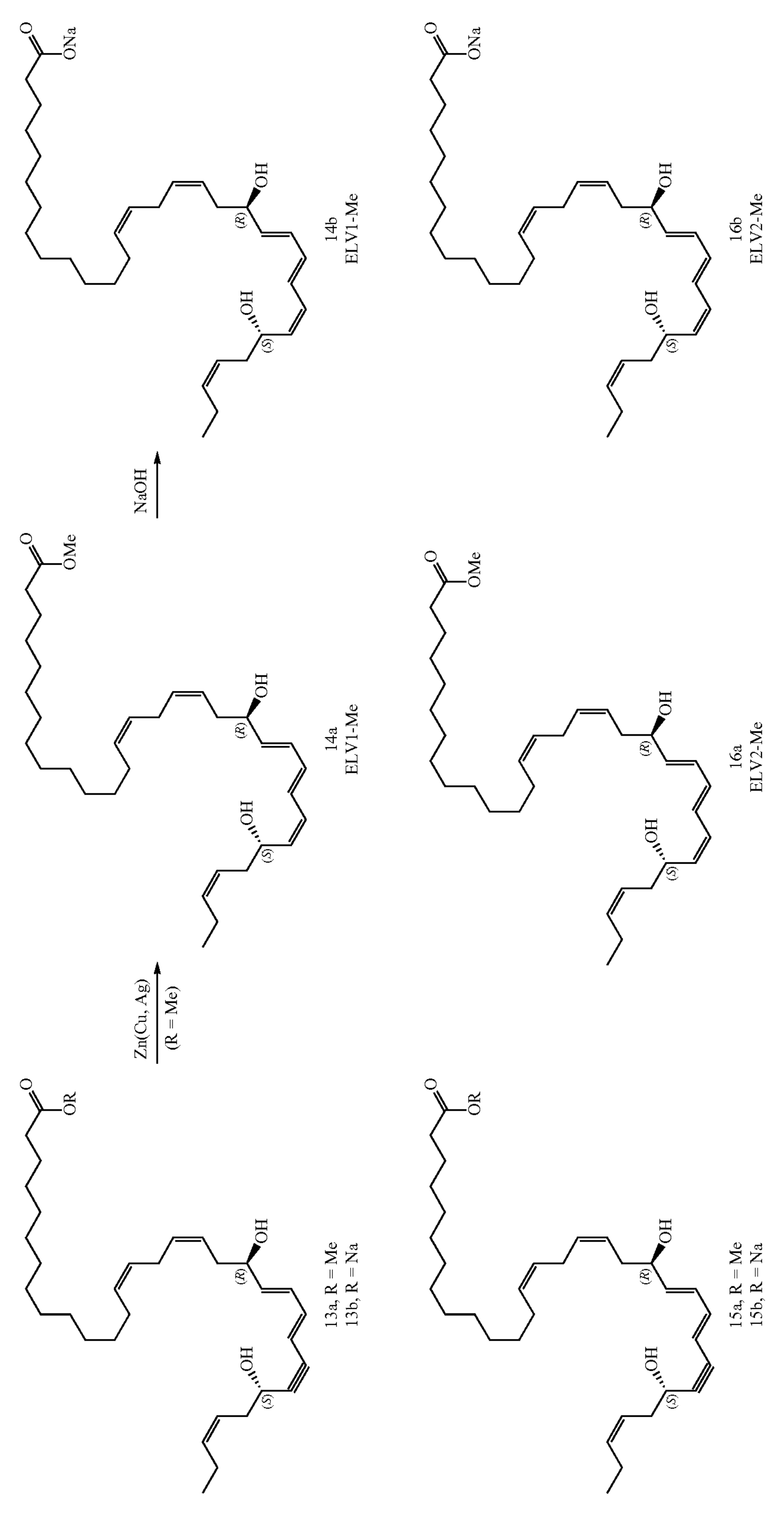
13a, R = Me
13b, R = Na
14a
ELV1-Me
14b
ELV1-Me
15a, R = Me
15b, R = Na
16a
ELV2-Me
16b
ELV2-Me Pharmaceutical Compositions for the Treatment of Diseases In other embodiments the present disclosure provides formulations of pharmaceutical compositions containing therapeutically effective amounts of one or more of compounds provided herein or their salts thereof in a pharmaceutically acceptable carrier.

The provided compositions contain one or more compounds provided herein or their salts thereof, and a pharmaceutically acceptable excipient, diluent, carrier and/or adjuvant. The compounds are preferably formulated into suitable pharmaceutical preparations such as solutions, suspensions, tablets, dispersible tablets, pills, capsules, powders, sustained release formulations or elixirs, for oral, buccal, intranasal, vaginal, rectal, ocular administration or in sterile solutions or suspensions for parenteral administration, as well as transdermal patch preparation and dry powder inhalers. The provided formulations may be in the form of a drop, such as an eye drop, and the pharmaceutical formulation may further contain known agents for the treatment of eye diseases. Typically the compounds described above are formulated into pharmaceutical compositions using techniques and procedures well known in the art (see, e.g., Ansel Introduction to Pharmaceutical Dosage Forms, Fourth Edition 1985, 126).

Preferred embodiments of the disclosure provides pharmaceutical compositions containing various forms of the provided compounds, as the free carboxylic acids or their pharmaceutically acceptable salts, or as their corresponding esters or their phospholipid derivatives. In other preferred embodiments the disclosure provides pharmaceutical compositions containing provided compounds that contain one or two hydroxyl groups at positions located between ω-3 to ω-18 of the very long chain polyunsaturated fatty acids, as the free carboxylic acids or their pharmaceutically acceptable salts, or as their corresponding esters.

In the provided compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of a disease, disorder or condition.

As described herein, the compositions can be readily prepared by adapting methods known in the art. The compositions can be a component of a pharmaceutical formulation. The pharmaceutical formulation may further contain known agents for the treatment of inflammatory or degenerative diseases, including neurodegenerative diseases. The provided compositions can serve as pro-drug precursors of the fatty acids and can be converted to the free fatty acids upon localization to the site of the disease.

The present disclosure also provides packaged composition(s) or pharmaceutical composition(s) for use in treating the disease or condition. Other packaged compositions or pharmaceutical compositions provided by the present disclosure further include indicia including at least one of: instructions for using the composition to treat the disease or condition. The kit can further include appropriate buffers and reagents known in the art for administering various combinations of the components listed above to the host.

Pharmaceutical Formulations

Embodiments of the present disclosure include a composition or pharmaceutical composition as identified herein and can be formulated with one or more pharmaceutically acceptable excipients, diluents, carriers and/or adjuvants. In addition, embodiments of the present disclosure include a composition or pharmaceutical composition formulated with one or more pharmaceutically acceptable auxiliary substances. In particular the composition or pharmaceutical composition can be formulated with one or more pharmaceutically acceptable excipients, diluents, carriers, and/or adjuvants to provide an embodiment of a composition of the present disclosure.

A wide variety of pharmaceutically acceptable excipients are known in the art. Pharmaceutically acceptable excipients have been amply described in a variety of publications, including, for example, A. Gennaro (2000) "Remington: The Science and Practice of Pharmacy," 20th edition, Lippincott, Williams, & Wilkins; Pharmaceutical Dosage Forms and Drug Delivery Systems (1999) H. C. Ansel et al., eds., 7th ed., Lippincott, Williams, & Wilkins; and Handbook of Pharmaceutical Excipients (2000) A. H. Kibbe et al., eds., 3rd ed. Amer. Pharmaceutical Assoc. The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In an embodiment of the present disclosure, the composition or pharmaceutical composition can be administered to the subject using any means capable of resulting in the desired effect. Thus, the composition or pharmaceutical composition can be incorporated into a variety of formulations for therapeutic administration. For example, the composition or pharmaceutical composition can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

Suitable excipient vehicles for the composition or pharmaceutical composition are, for example, water, saline, dextrose, glycerol, ethanol, or the like, and combinations thereof. In addition, if desired, the vehicle may contain minor amounts of auxiliary substances such as wetting or emulsifying agents or pH buffering agents. Methods of preparing such dosage forms are known, or will be apparent upon consideration of this disclosure, to those skilled in the art. See, e.g., Remington's Pharmaceutical Sciences, Mack Publishing Company, Easton, Pennsylvania, 17th edition, 1985. The composition or formulation to be administered will, in any event, contain a quantity of the composition or pharmaceutical composition adequate to achieve the desired state in the subject being treated.

Compositions of the present disclosure can include those that comprise a sustained release or controlled release matrix. In addition, embodiments of the present disclosure can be used in conjunction with other treatments that use sustained-release formulations. As used herein, a sustained-release matrix is a matrix made of materials, usually polymers, which are degradable by enzymatic or acid-based hydrolysis or by dissolution. Once inserted into the body, the matrix is acted upon by enzymes and body fluids. A sustained-release matrix desirably is chosen from biocompatible materials such as liposomes, polylactides (polylactic acid), polyglycolide (polymer of glycolic acid), polylactide co-glycolide (copolymers of lactic acid and glycolic acid), polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix. In another embodiment, the pharmaceutical composition of the present disclosure (as well as combination compositions) can be delivered in a controlled release system. For example, the composition or pharmaceutical composition may be administered using intravenous infusion, an implantable osmotic pump, a transdermal patch, liposomes, or other modes of administration. In one embodiment, a pump may be used (Sefton (1987). CRC Crit. Ref. Biomed. Eng. 14:201; Buchwald et al. (1980). Surgery 88:507; Saudek et al. (1989). N. Engl. J. Med. 321:574). In another embodiment, polymeric materials are used. In yet another embodiment a controlled release system is placed in proximity of the therapeutic target thus requiring only a fraction of the systemic dose. In yet another embodiment, a controlled release system is placed in proximity of the therapeutic target, thus requiring only a fraction of the systemic. Other controlled release systems are discussed in the review by Langer (1990). Science 249:1527-1533.

In another embodiment, the compositions of the present disclosure (as well as combination compositions separately or together) include those formed by impregnation of the composition or pharmaceutical composition described herein into absorptive materials, such as sutures, bandages, and gauze, or coated onto the surface of solid phase materials, such as surgical staples, zippers and catheters to deliver the compositions. Other delivery systems of this type will be readily apparent to those skilled in the art in view of the instant disclosure.

In another embodiment, the compositions or pharmaceutical compositions of the present disclosure (as well as combination compositions separately or together) can be part of a delayed-release formulation. Delayed-release dosage formulations can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

Embodiments of the composition or pharmaceutical composition can be administered to a subject in one or more doses. Those of skill will readily appreciate that dose levels can vary as a function of the specific the composition or pharmaceutical composition administered, the severity of the symptoms and the susceptibility of the subject to side effects. Preferred dosages for a given compound are readily determinable by those of skill in the art by a variety of means.

In an embodiment, multiple doses of the composition or pharmaceutical composition are administered. The frequency of administration of the composition or pharmaceutical composition can vary depending on any of a variety of factors, e.g., severity of the symptoms, and the like. For example, in an embodiment, the composition or pharmaceutical composition can be administered once per month, twice per month, three times per month, every other week (qow), once per week (qw), twice per week (biw), three times per week (tiw), four times per week, five times per week, six times per week, every other day (qod), daily (qd), twice a day (qid), three times a day (tid), or four times a day. As discussed above, in an embodiment, the composition or pharmaceutical composition is administered 1 to 4 times a day over a 1 to 10 day time period.

The duration of administration of the composition or pharmaceutical composition analogue, e.g., the period of time over which the composition or pharmaceutical composition is administered, can vary, depending on any of a variety of factors, e.g., patient response, etc. For example, the composition or pharmaceutical composition in combination or separately, can be administered over a period of time of about one day to one week, about one day to two weeks.

The amount of the compositions and pharmaceutical compositions of the present disclosure that can be effective in treating the condition or disease can be determined by standard clinical techniques. In addition, in vitro or in vivo assays can optionally be employed to help identify optimal dosage ranges. The precise dose to be employed can also depend on the route of administration, and can be decided according to the judgment of the practitioner and each patient's circumstances.

Routes of Administration

Embodiments of the present disclosure provide methods and compositions for the administration of the active agent(s) to a subject (e.g., a human) using any available method and route suitable for drug delivery, including in vivo and ex vivo methods, as well as systemic and localized routes of administration. Routes of administration include intranasal, intramuscular, intratracheal, subcutaneous, intradermal, topical application, intravenous, rectal, nasal, oral, and other enteral and parenteral routes of administration. Routes of administration may be combined, if desired, or adjusted depending upon the agent and/or the desired effect. An active agent can be administered in a single dose or in multiple doses.

The VLC-PUFA and their biogenic derivatives are formed in cells and are not a component of human diet. Possible routes of administration of the novel compounds provided herein will include oral and parenteral administration, including intravitreal and subretinal injection into the eye to by-pass intestinal absorption, the gut-liver, and the blood-ocular barrier. The provided formulations may be delivered in the form of a drop, such as an eye drop, or any other customary method for the treatment of eye diseases.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the composition. Where systemic delivery is desired, administration typically involves invasive or systemically absorbed topical or mucosal administration of pharmaceutical preparations. In an embodiment, the composition or pharmaceutical composition can also be delivered to the subject by enteral administration. Enteral routes of administration include, but are not limited to, oral and rectal (e.g., using a suppository) delivery.

Methods of administration of the composition or pharmaceutical composition through the skin or mucosa include, but are not limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" that deliver their product continuously via electric pulses through unbroken skin for periods of several days or more.

Methods for the Treatment of Diseases, Disorders or Conditions

Described herein are methods and compositions for treating and protecting an organ or tissue from the effects of oxidative stress or other homeostatic disruptions associated with a persistent inflammatory condition or a progressive degenerative disease, including a neurodegenerative disease.

The provided compounds, compositions, and methods can be used for the preventive and therapeutic treatment of a disease, disorder or condition. The list of diseases that can be treated with the provided compositions and methods include but are not limited to inflammatory diseases, degenerative diseases, including neurodegenerative diseases including, but not limited to the following:

(a) Inflammatory diseases, including acute and chronic disorders were homeostasis is disrupted by abnormal or dysregulated inflammatory response. These diseases are initiated and mediated by a number of inflammatory factors, including oxidative stress, chemokines, cytokines, breakage of blood/tissue barriers, autoimmune diseases or other conditions that engage leukocytes, monocytes/macrophages or parenchymal cells that induce excessive amounts of pro-cell injury, pro-inflammatory/disruptors of homeostasis mediators. These diseases occur in a wide range of tissues and organs and are currently treated, by anti-inflammatory agents such as corticosteroids, non-steroidal anti-inflammatory drugs, TNF modulators, COX-2 inhibitors, etc. Representative examples include but are not limited to: rheumatoid arthritis, osteoarthritis, atherosclerosis, cancer, diabetes, intestinal bowel disease, prostatitis, ischemic stroke, traumatic brain damage, spinal cord injury, multiple sclerosis, autism, schizophrenia, depression, traumatic brain injury, status epilepticus, Huntington's disease, Alzheimer's disease, Parkinson's disease, amyotrophic lateral sclerosis, retina degenerative diseases, age-related macular degeneration, inherited retinal degenerative diseases, Stargardt-like macular dystrophy, X-linked juvenile retinoschisis, perioperative hypoxia, retinitis pigmentosa, glaucoma, etc.

(b) Degenerative diseases, which include conditions that involve progressive loss of vital cells and tissues that result in progressive impairment of function, such as loss of cartilage in knees, hip joints or other joints such as in osteoarthritis. Other degenerative diseases engages cellular and intercellular homeostasis perturbations and includes heart disease, atherosclerosis, cancer, diabetes, intestinal bowel disease, osteoporosis, prostatitis, rheumatoid arthritis, etc.

(c) Neurodegenerative diseases, which include some of the major diseases of the brain, retina, spinal cord and peripheral nerves, whereby a progressive demise of cellular organization leads to impaired function. These are due to immune or inflammatory disorders and/or to inherited conditions or aging. They include ischemic stroke, traumatic brain damage, spinal cord injury, epilepsy, multiple sclerosis, Alzheimer's disease, Parkinson's disease, amyotrophic lateral sclerosis, retina degenerative diseases such as age-related macular degeneration, inherited eye diseases such as retinitis pigmentosa, glaucoma, etc.

(d) Retinal degenerative diseases, which are the leading causes of blindness that affects very large numbers of people and involve the deterioration of the retina caused by the progressive and eventual death of the photoreceptor cells of the retina. Examples of common retinal degenerative diseases include but are not limited to: retinitis pigmentosa, age-related macular degeneration, inherited retinal degenerative diseases, Stargardt-like macular dystrophy, X-linked juvenile retinoschisis, perioperative hypoxia, glaucoma, etc.

The provided compounds, compositions, and methods can also be used to induce the increased expression of Sirtuin1 (SIRT1) and to treat diseases and conditions that can benefit from an increased expression of SIRT1. Sirtuin1 (SIRT1) belongs to a family of highly conserved proteins associated with aging, modulation of energy metabolism, genomic stability, stress resistance, Alzheimer's and other neurodegenerative diseases. Sirtuin1 is a major therapeutic target in many diseases including cancer, diabetes, inflammatory disorders and neurodegenerative disease, all of which can be treated with the provided compounds, compositions and methods.

Also described herein are methods and compositions for treating and protecting the retina of the eye. Specifically, described herein are methods for treating and protecting retinal pigment epithelial cells and photoreceptors of the eye. Generally, compositions as described herein are administered to a subject in any preferred mode of administration. Such modes include in an eye drop.

Methods and compositions described herein can be used to treat a diseased eye in a subject. For example, the disease can be a retinal disease, such as retinal degeneration. In this instance, the retinal degeneration can be prevented or delayed. Eye diseases that are particularly suited for methods and compositions as described herein include age-related macular degeneration, retinitis pigmentosa, and Stargardt disease.

Methods and compositions described herein can promote the survival of photoreceptors in the retina.

Methods and compositions described herein can induce signaling pathways that enhance cell survival in cell specific to the eye, such as retinal pigment epithelial cells and photoreceptors.

While embodiments of the present disclosure are described in connection with the Examples and the corresponding text and figures, there is no intent to limit the disclosure to the embodiments in these descriptions. On the contrary, the intent is to cover all alternatives, modifications, and equivalents included within the spirit and scope of embodiments of the present disclosure.

EXAMPLES

Example 1

Figure 1:
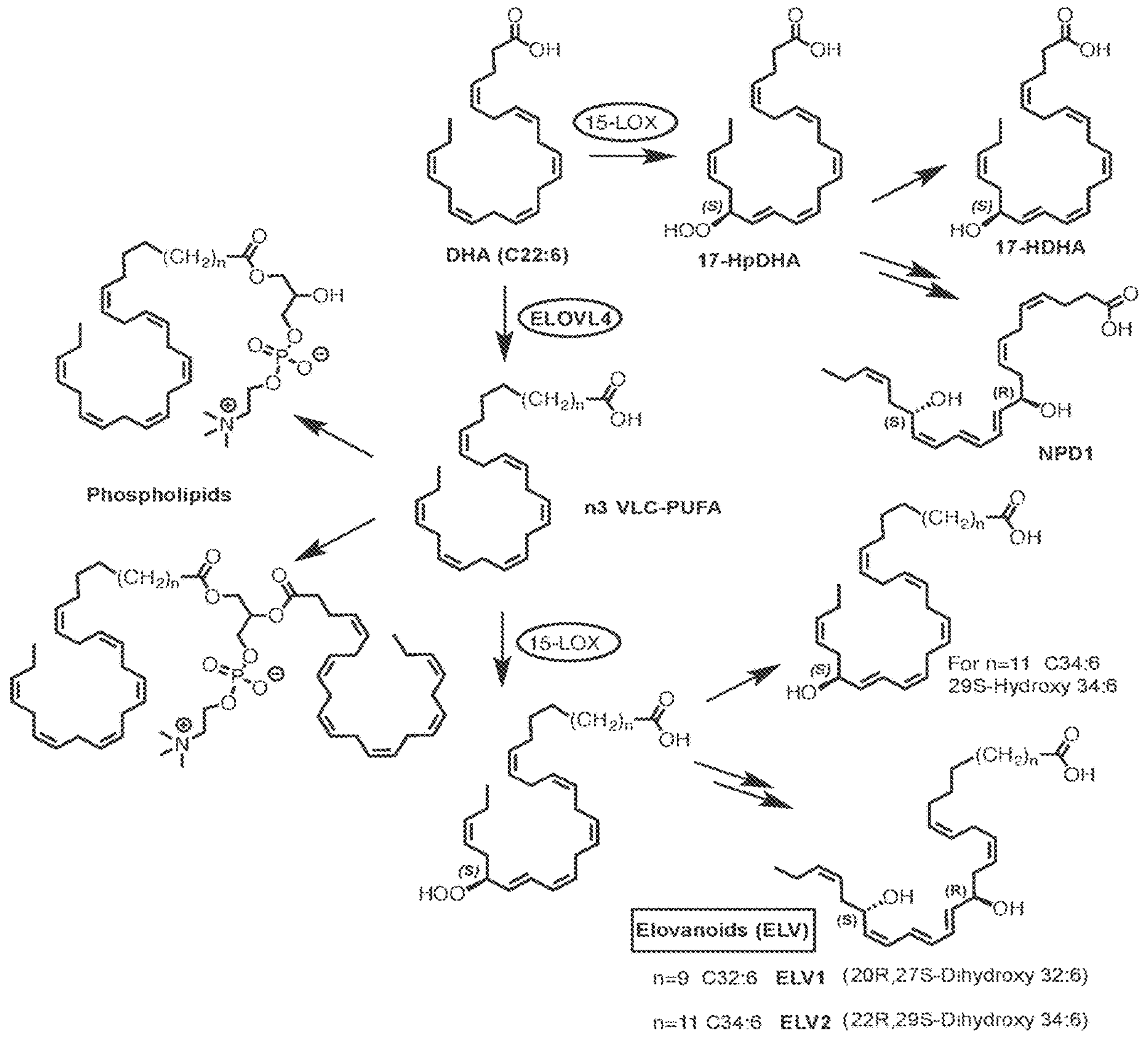
FIG. 1. Postulated biosynthesis of selected hydroxylated derivatives derived from DHA (C22:6n3, or C22:6) and from omega-3 very long chain polyunsaturated fatty acids (n3-VLC-PUFA). Lipoxygenation of DHA with 15-LOX affords 17-HpDHA, which is either reduced to 17-HDHA or is transformed into NPD1. DHA is also a converted by the elongase enzyme ELOVL4 (elongation of very long fatty acids-4) into n3-VLC-PUFA, such as C32:6 and C34:6, which can be incorporated into phospholipids. Lipoxygenation of n3-VLC-PUFA with 15-LOX leads to the formation of monohydroxy derivatives of n3-VLC-PUFA, such as 29-hydroxy 34:6 and 22,29-dihydroxy 34:6. Given the key role of the ELOVL4 enzyme, the name "Elovanoid" is being used herein for a bioactive enzymatically-derived hydroxylated derivative of VLC-PUFA. Thus, the name Elovanoid 1 (ELV1) is being used for the 20R,27S-dihydroxy 32:6 derivative, and the name Elovanoid 2 (ELV2) is being used for the 22R,29S-dihydroxy 32:6 derivative. The stereochemistry of the mono- and di-hydroxy compounds were presumed to be the same as those derived from DHA.

Evidence for the formation of hydroxylated VLC-PUFA in cells as postulated in FIG. 1, and as documented in FIG. 2. The biogenic conversion of the n3 VLC-PUFA (1) to the mono-hydroxylated derivative 2 and the di-hydroxylated derivative 3 demonstrates the ability of VLC-PUFA to generate hydroxylated derivatives with structures analogous to those obtained from other omega-3 PUFA such as DHA. The preferred structures of 2 are 2a and 2b, while the preferred structures of 3 are 3a and 3b. Although these novel findings do not prove that compounds 2 or 3 are naturally occurring in living systems, they provide a design rationale for the provided compounds and their biological activities, as provided in this disclosure. The cell-derived hydroxylated derivatives 2 and 3 were obtained from human retinal pigment epithelial cells in culture. Human retinal pigment epithelial cells (spontaneously transformed ARPE-19 cells) or primary human retinal pigment epithelial cells (HRPE) were incubated with 34:6n3 (100 nM) during 12-16 hours and then the culture media collected lipid extracted and run in LC-MS/MS. The results suggest that C34:6 with an m/z of 495.5 (FIG. 2A) yielded a hydroxylated product analogous to the mono-hydroxylated DHA derivative 17-HDHA having a parent-H m/z of 511.8 and a fragment m/z of 413, which is consistent with the mono-hydroxylated compound 29-hydroxy-34:6 (FIG. 2B). The data show that compound C34:6 was also converted to an elongation product analogous to the di-hydroxylated DHA derivative NPD1,(10R, 17S-dihydroxy-docosa-4Z,7Z,11E,13E,15Z,19Z-hexaenoic acid) having a parent-H m/z of 527.8, and a fragment m/z of 206 consistent with the NPD1-like di-hydroxylated compound 22,29-dihydroxy-34:6 (FIG. 2C). The stereochemistry of the mono- and di-hydroxy compounds were not possible to determine, but they were presumed to be the same as those derived from DHA.

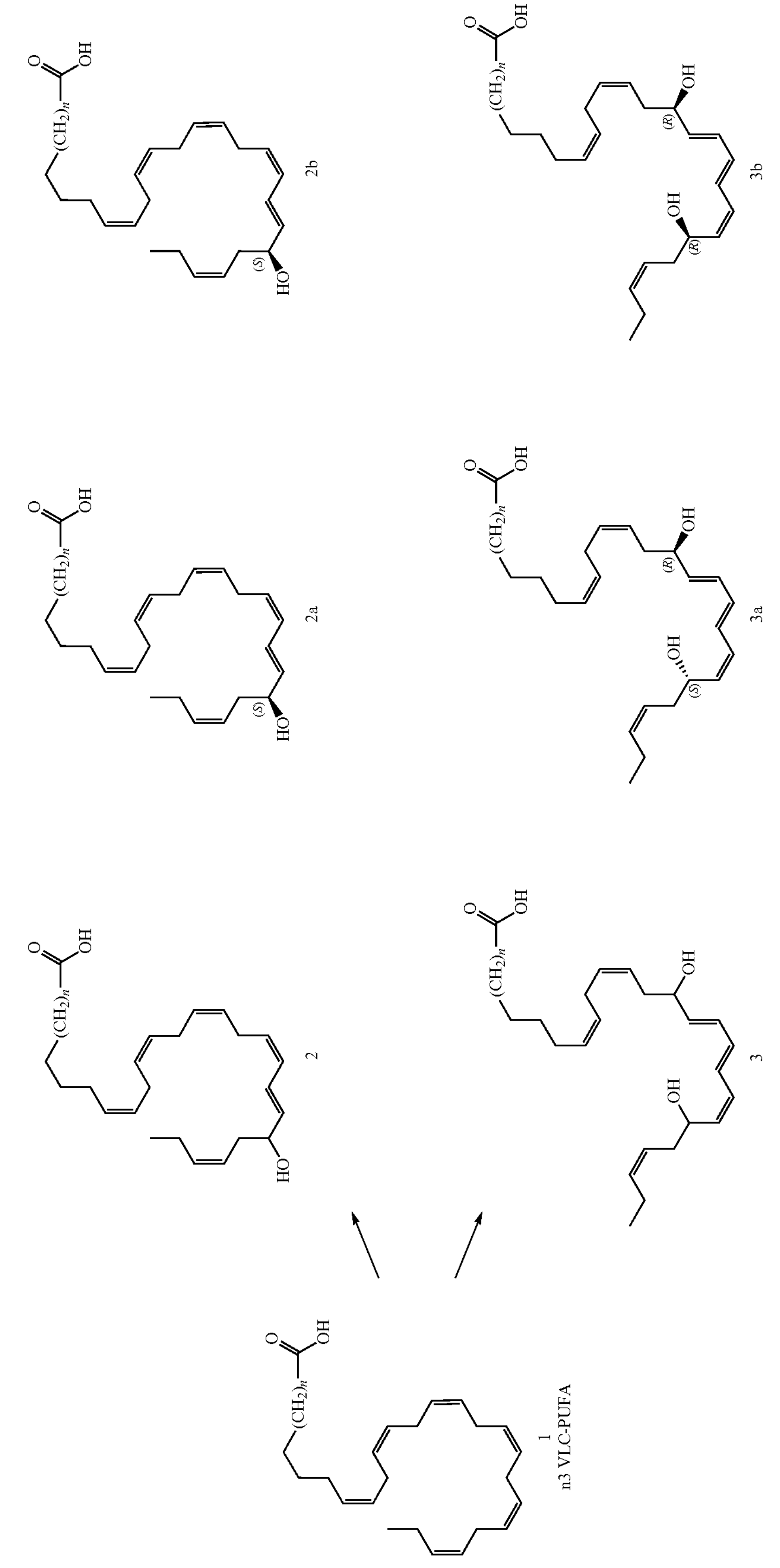
1
n3 VLC-PUFA
2
2a
2b
3
3a
3b

Example 2

Representative of experiments used human retinal pigment epithelial (RPE) cells, which are neuroectoderm-derived post-mitotic cells of the retina, an integral part of the central nervous system. These cells are richly endowed with a multitude of mechanisms to protect themselves from injury and to protect other cells, particularly the survival of photoreceptors. They are the most active phagocyte of the human body, critical for the health of photoreceptors and vision, and have the ability to secrete neurotrophins and other beneficial substances. In pathological conditions they recapitulate aspects of Alzheimer's disease by processing amyloid precursor protein and contributing to the formation of Drusen, analogously to the senile amyloid plaques. Thus, these are among the reasons that experimental data included in this disclosure were obtained with RPE cells. Therefore, the data provided herein are representative of the expected activities of the provided compounds in other cells and tissues where VLC-PUFA are known to be generated or be present.

Evidence of cytoprotection by 32.6 and 34.6 VLC-PUFA in oxidative-stress induced ARPE-19 cells as detailed in (FIG. 4): (A) Cytoprotective effects of NPD1 like compounds on OS induced apoptosis. The results shown in this figure compare the cytoprotective capacities of very long chain polyunsaturated fatty acids (VLC-PUFA), elovanoids ELV1 and ELV2, and neuroprotectin D1 (NPD1) in human retinal pigment epithelial (RPE) cells deficient in 15-LOX-D1 by measuring the protection of cell deaths induced by oxidative stress (OS) by these compounds. The results indicate that NPD1 provided the maximum protection (60%), followed by elovanoids at intermediate level (55%), and VLC-PUFA (50%), the least compared to OS (90%). (B) Elovanoid precursors protect human retinal pigment epithelial cells deficient in 15-LOX-1, unlike DHA, from oxidative stress conditions. This experiment clearly shows that VLC-PUFA, elovanoid precursors 32:6 and 34:6, and NPD1 protect against cell death in 15-LOX-D1 cells under oxidative stress conditions. On the other hand, DHA was unable to do so, as the 15-LOX-D1 cells lack the enzyme required for conversion of DHA to the neuroprotective agent.

Example 3

Figure 5:
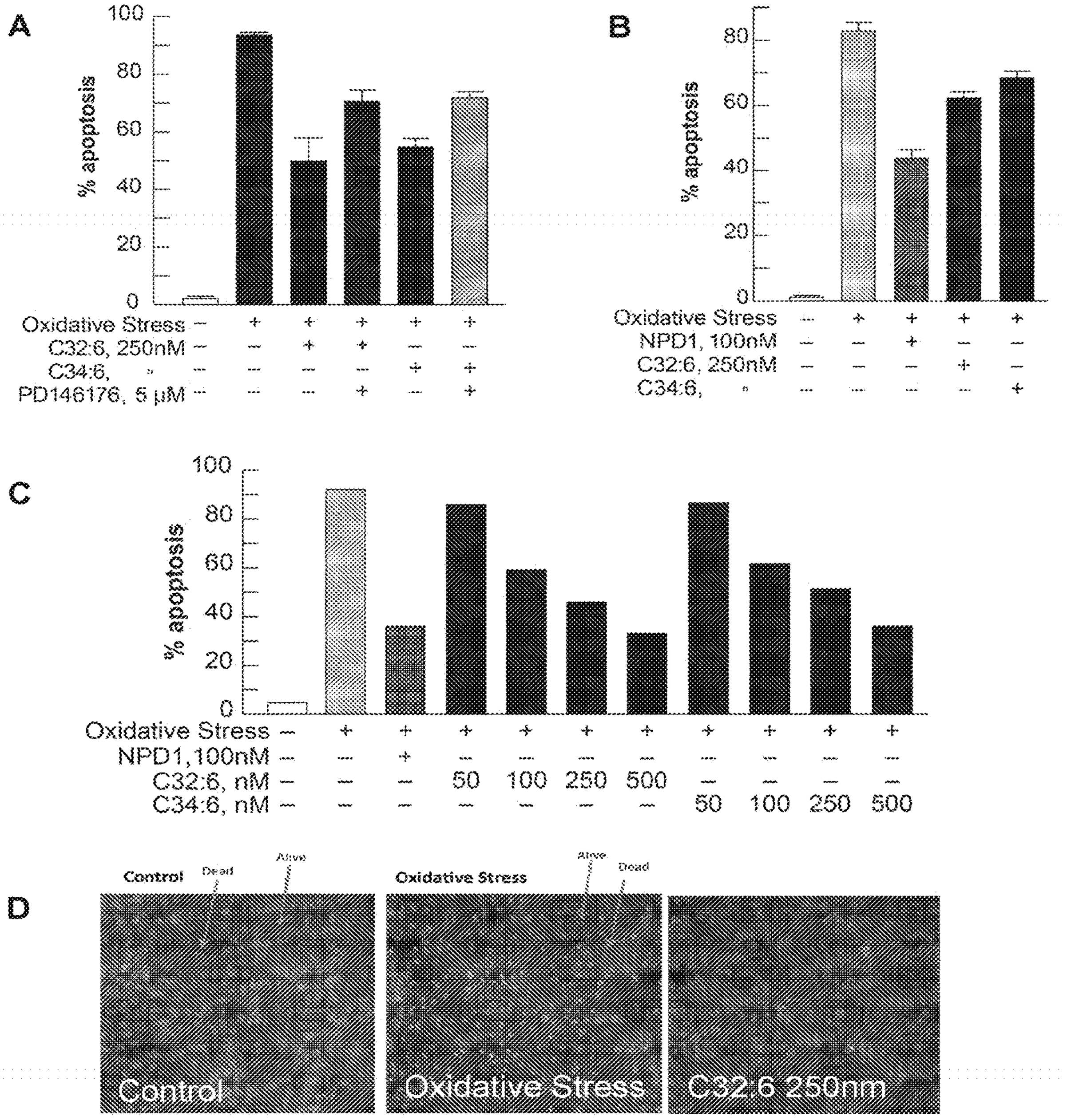
FIG. 5. (A) Effect of PD146176 on VLC-PUFA-inhibited apoptosis induced by OS in ARPE-19 cells. This experiment demonstrated the effect of 15-lipooxygenese inhibitor PD146176 on the VLC-PUFA-mediated inhibition of cell death in ARPE-19 cells under stressed condition. It is evident that 32:6 and 34:6 LCAF were able to induce a substantial amount (55 and 48% respectively) of neuroprotection compared to PD 146176 (22%) when the stressed cells were treated with 5 μm of 15-LOX-D1 inhibitor. It can be concluded that since PD146176 is the inhibitor of 15-lipooxygenase enzyme, it might be protecting the stressed RPE cells by accumulating neuroprotective agents inside the cells. (B) Comparison of cytoprotective capacities of NPD1, C32:6 and C34:6 VLC-PUFA on oxidative stress-induced apoptosis in 15-LOX-1 cells. Shown here is the comparison of neuroprotection in a 15-LOX-1-deficient cell line under oxidative stress with 32:6 and 34:6 VLC-PUFA along with NPD1. 32:6 and 34:6 LCAF were able to induce neuroprotection (45% and 40% respectively), as compared to oxidative stress (90%) under this condition. (C) Concentration dependent cytoprotection by C32:6 and C34:6 VLC-PUFA in oxidative-stress induced ARPE-19 cells. A concentration (50-500 nM) kinetic of cytoprotection induced by LCAF 32:6 and 34:6 in RPE cell culture under OS was shown here. The result indicates that there was a gradual decrease of cell deaths starting from 50 nM concentrations of both 32:6 and 34:6 LCAF, very good intermediate effect at 250 nM, and maximum effect at 500 nM. We decided to use 250 nM concentrations of 32:6 and 34:6 LCAF in subsequent experiments. (D) Selected images of alive and dead cells from this study (control, OS, treatment with C32:6).

FIG. 5—(A) Effect of PD146176 on VLC-PUFA inhibited apoptosis induced by OS in ARPE-19 cells. This experiment demonstrated the effect of 15-lipooxygenese inhibitor PD146176 on the VLC-PUFA-mediated inhibition of cell death in ARPE-19 cells under stressed condition. It is evident that 32:6 and 34:6 LCAF were able to induce a substantial amount (55 and 48% respectively) of neuroprotection compared to PD 146176 (22%) when the stressed cells were treated with 5 μm of 15-LOX-D1 inhibitor. It can be concluded that since PD146176 is the inhibitor of 15-lipooxygenase enzyme, it might be protecting the stressed RPE cells by accumulating neuroprotective agents inside the cells. (B) Comparison of cytoprotective capacities of NPD1, C32:6 and C34:6 VLC-PUFA on oxidative stress-induced apoptosis in 15-LOX-1 cells. Shown here is the comparison of neuroprotection in a 15-LOX-1-deficient cell line under oxidative stress with 32:6 and 34:6 VLC-PUFA along with NPD1. 32:6 and 34:6 VLC-PUFA were able to induce neuroprotection (45% and 40% respectively), as compared to oxidative stress (90%) under this condition. (C) Concentration dependent cytoprotection by C32:6 and C34:6 VLC-PUFA in oxidative-stress induced ARPE-19 cells. A concentration (50-500 nM) kinetic of cytoprotection induced by VLC-PUFA 32:6 and 34:6 in RPE cell culture under OS was shown here. The result indicates that there was a gradual decrease of cell deaths starting from 50 nM concentrations of both 32:6 and 34:6 VLC-PUFA, very good intermediate effect at 250 nM, and maximum effect at 500 nM. We decided to use 250 nM concentrations of 32:6 and 34:6 VLC-PUFA in subsequent experiments. (D) Selected images of alive and dead cells from this study (control, OS, treatment with C32:6).

Example 4

Figure 6:
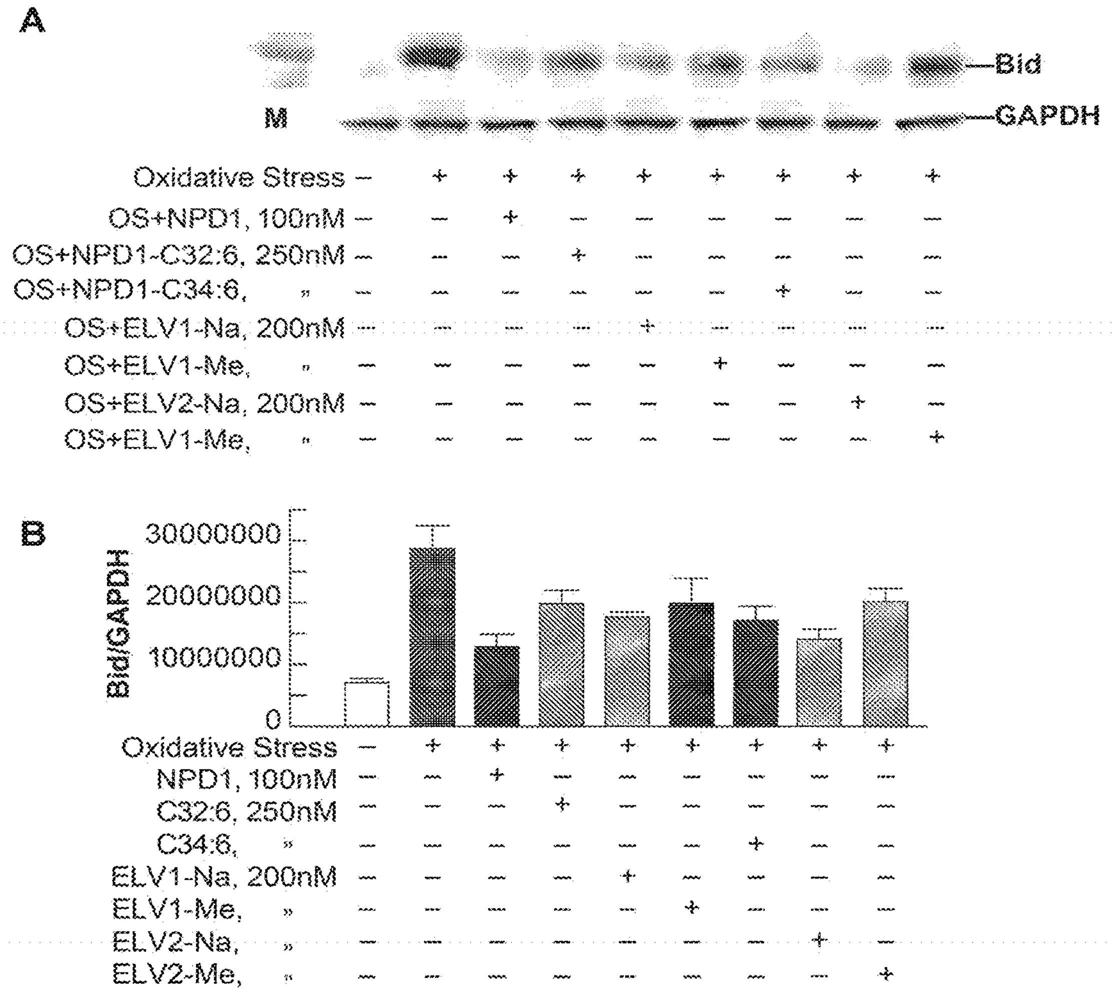
FIG. 6. (A) VLC-PUFA and elovanoids ELV1 and ELV2 mediated effect on Bid upregulation in ARPE-19 cells under stress. This figure displays the downregulation of the proapoptotic protein of the Bcl2 family Bid by western blot analysis by VLC-PUFA and elovanoids in RPE cells in culture under oxidative-stress. Results indicate that upregulated Bid protein by OS, as evident from the figure, was inhibited by both elovanoids and VLC-PUFA. It is interesting to see that the sodium salts of the elovaniod precursors are more effective than the methyl ester forms. (B) VLC-PUFA and ELV1 and ELV2 compounds mediated upregulation of Bid in ARPE-19 cells under stress. This Figure shows the quantification of Bid downregulation.

FIG. 6—(A) VLC-PUFA and elovanoids ELV1 and ELV2 mediated effect on Bid upregulation in ARPE-19 cells under stress. This figure displays the downregulation of the proapoptotic protein of the Bcl2 family Bid by western blot analysis by VLC-PUFA and elovanoids in RPE cells in culture under oxidative-stress. Results indicate that upregulated Bid protein by OS, as evident from the figure, was inhibited by both elovanoids and VLC-PUFA. It is interesting to see that the sodium salts of the elovaniod precursors are more effective than the methyl ester forms. (B) VLC-PUFA and ELV1 and ELV2 compounds mediated upregulation of Bid in ARPE-19 cells under stress. This Figure shows the quantification of Bid downregulation.

Example 5

Figure 7:
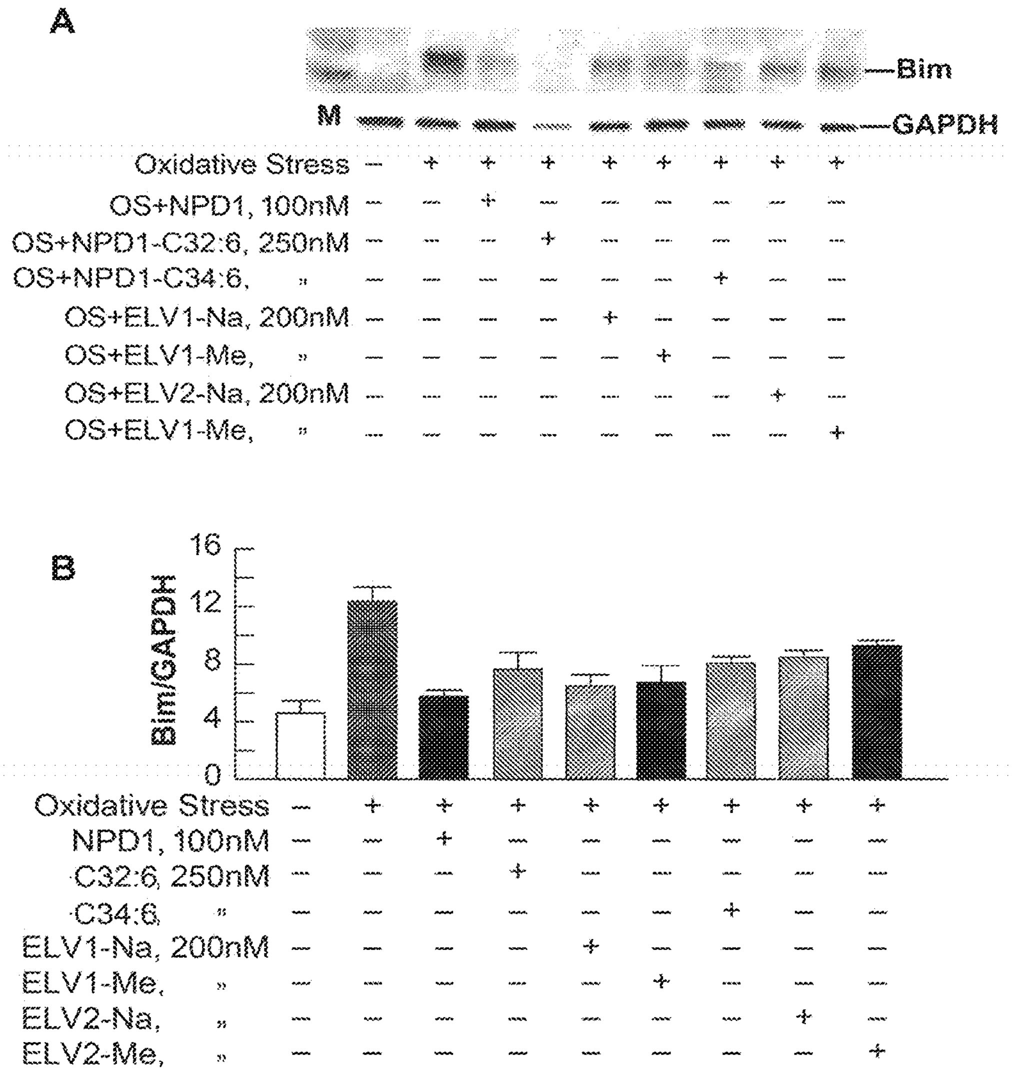
FIG. 7. (A) VLC-PUFA and ELV1 and ELV2 compounds mediated downregulation of Bim in ARPE-19 cells under stress. Bim, another class of Bcl2 family, has been tested like Bid in this figure to confirm our previous results. VLC-PUFA and elovanoids protected against the upregulation of Bim by OS, similar to Bid, in RPE cells under stress. (B) VLC-PUFA and elovanoids mediated effect on Bim downregulation in ARPE-19 cells under stress. This Figure shows the quantification of Bim downregulation.

FIG. 7—A) VLC-PUFA and ELV1 and ELV2 compounds mediated upregulation of Bim in ARPE-19 cells under stress. Bim, another class of Bcl2 family, has been tested like Bid in this figure to confirm our previous results. VLC-PUFA and elovanoids protected the upregulation of Bim by OS, similar to Bid, in RPE cells under stress. (B) VLC-PUFA and elovanoids mediated effect on Bim upregulation in ARPE-19 cells under stress. This Figure shows the quantification of Bim downregulation.

Example 6

FIG. 8—(A) Bcl-xL-upregulation by elovanoids ELV1 and ELV2 in ARPE-19 cells under stress. Bcl-xL is the antiapoptotic Bcl2 family protein. Like proapoptotic proteins Bid and Bim, the effect of elovaniod precursors on the antiapoptotic protein Bcl-xL was tested in this figure in RPE cells under OS. Results showed that elovaniod precursors were able to upregulate the Bcl-xL protein in RPE cells under stress, which is the opposite effect of Bid and Bim. (B) Effect of NPD1, ELV1 and ELV2 on Bax expression in LOX-D cells under stress. Proapoptotic Bax was tested in this figure. It is evident that elovaniod precursors downregulated the Bax upregulation by OS in RPE cells under OS, which is consistent with our inhibition of apoptosis experiments, as shown before. C) VLC-PUFA and elovanoids ELV1 and ELV2 mediated effect on Bax upregulation in ARPE-19 cells under stress. In this experiment, elovanoid precursors along with VLC-PUFA were tested on the downregulation of the Bax protein in RPE cells under stress.

Example 7

FIG. 9—(A) VLC-PUFA and elovanoids ELV1 and ELV2 mediated effect on Bcl2 upregulation in ARPE-19 cells under stress. In this experiment we tested the effect of elovaniod precursors on Blc2 upregulation along with VLC-PUFA in stressed RPE. (B) Quantification of Bcl2 upregulation by NPD1, ELV1 and ELV2 in LOX-D cells. Bcl2 is an important antiapoptotic protein of the Bcl2 family protein. It is evident that elovaniod precursors upregulated the Bcl2 protein in RPE cells under stress.

Example 8

FIG. 10—(A) Effect of NPD1 and VLC-PUFA C32:6 and C34:6 in mediating upregulation of SIRT1 in ARPE-19 cells. (B) Quantification of SIRT1 upregulation by NPD1, C32:6 and C34:6. SIRT1 (Sirtuin1) belongs to a family of highly conserved proteins linked to caloric restriction beneficial outcomes and aging by regulating energy metabolism, genomic stability and stress resistance. SIRT1 is a potential therapeutic target in several diseases including cancer, diabetes, inflammatory disorders, and neurodegenerative diseases or disorders. Elovanoids induce cell survival involving the upregulation of the Bcl2 class of survival proteins and the downregulation of pro-apoptotic Bad and Bax under oxidative stress (OS) in RPE cells. The data in this Figure suggest that elovanoids upregulate SIRT1 abundance in human RPE cells when confronted with OS. As a consequence, remarkable cell survival takes place. This target of elovanoids might be relevant to counteract consequences of several diseases associated with SIRT1.

Example 9

FIG. 11—The elovanoid ELV2 in 200 nM concentrations protects neuronal cells in primary cultures from NMDA-induced toxicity (A), and MK-801 potentiates protection as assessed by MTT assay for cell viability (B). In several neurological and neurodegenerative diseases, such as stroke, epilepsy, status epilepticus, traumatic head injury, etc., as well as ophthalmological diseases, such as glaucoma, an excessive presynaptic release of the excitatory neurotransmitter glutamate takes place. As a consequence, glutamate transporters that function to remove extracellular glutamate from astrocytes and neurons are overwhelmed and the NMDA-type glutamate receptor is over-activated. This receptor is a calcium channel that therefore leads to a flooding of calcium into the postsynaptic cell. The overall phenomena is refer to as excitotoxicity that in turn leads to neuronal damage and cell death. MK801 is a known blocker of this receptor used here as a control. The results in this Figure demonstrate that when NMDA in increasing concentrations is added to neuronal cultures it leads to cell death, while the use of ELV2 reduces cell death and increases cell viability. These data support the use of the elovanoids for the treatment of neurodegenerative diseases and conditions involving NMDA-related excitotoxicity, such as: ischemic stroke, Alzheimer's disease, Parkinson's disease, etc.

Example 10

FIG. 12—Elovanoids ELV2-Na and ELV2-Me are more active than DHA and NPD1 in a model of ischemic stroke after 2 hrs of MCAo (middle cerebral occlusion). To test the novel elovanoids the experimental design consisted injecting the compounds into the right cerebral ventricle (5 μg/per rat, ICV), one hour after two hours of an ischemic stroke in rats and following thereafter the neurological behavior (neurological score) during 7 days. The protocol in brief was as follows. The injection was made through a surgically implanted metal canula (Alzet) into the right lateral ventricle. Two days later the right middle cerebral artery (MCA) was occluded for 2 h by means of an intraluminal nylon filament (Belayev et al, Traslational Stroke Research, 2010). Then one hour after the compounds were injected dissolved in sterile cerebrospinal fluid. The occlusion was transient performed as follows. The right common carotid artery was exposed through an incision in the neck and was isolated from surrounding tissues. The distal external carotid artery and pterygopalatine arteries were tied. A 4-cm of 3-0 monofilament nylon suture coated with poly-Lysine was introduced into the internal carotid artery and MCA. The suture position was confirmed by advancing the suture 20-22 mm from the common carotid artery bifurcation. Then, the rats were allowed to awaken from anesthesia and returned to their cages. The degree of stroke injury was assessed by neurological assessment of each rat at 60 min after onset of MCAo. Rats that do not demonstrate high-grade contralateral deficit (score, 10-11) were excluded from the study. After 2 hours of MCA occlusion, the rats were re-anesthetized temperature probes were reinserted and the intraluminal suture was removed. The neck incision was closed with silk sutures, and the animals were allowed free access to food and water. These results show that the use elovanoids after the ischemic event result in remarkable neuroprotection, suggesting a potential therapeutic benefit for the treatment of ischemic stroke and other neurodegenerative diseases or disorders. The sodium salt ELV2-Na showed a greater potency, presumably because it delivers the active form of ELV2 and has a more immediate effect. The methyl ester ELV2-Me is expected to first be hydrolyzed via the actions of esterases, and it may have a more delayed effect, which may be beneficial for a sustainable long-term treatment. Overall, these data demonstrate the neuroprotective effects of the elovanoids, either as pharmaceutically acceptable salts (e.g. ELV2-Na), or in the form of a prodrug, such as an ester derivative (e.g. ELV2-Me), or as a pharmaceutical composition containing a combination of the two forms that can have both an immediate and a sustainable long-term therapeutic effect.

REFERENCES

Bazan N G. Neuroprotectin D1 (NPD1): A DHA-derived mediator that protects brain and retina against cell injury-induced oxidative stress. Brain Pathology. 2005; 15(2): 159-66.

Bazan N G, Eady T N, Khoutorova L, Atkins K D, Hong S, Lu Y, Zhang C, Jun B, Obenaus A, Fredman G, Zhu M, Winkler J W, Petasis N A, Serhan C N, Belayev L. Novel aspirin-triggered neuroprotectin D1 attenuates cerebral ischemic injury after experimental stroke. Exp Neurol. 2012; 236(1):122-30.

Bazan N G, Molina M F, Gordon W C. Docosahexaenoic acid signalolipidomics in nutrition: Significance in aging, neuroinflammation, macular degeneration, Alzheimer's, and other neurodegenerative diseases. Annual Review of Nutrition, 2011; 31(1):321-51.

Bennett L D, Brush R S, Chan M, Lydic T A, Reese K, Reid G E, Busik J V, Elliott M H, Anderson R E. Effect of Reduced Retinal VLC-PUFA on Rod and Cone PhotoreceptorsRetinal VLC-PUFA in Rod and Cone Photoreceptors. Investigative Ophthalmology & Visual Science. 2014; 55(5):3150-7.

Brush R S, Tran J-T A, Henry K R, McClellan M E, Elliott M H, Mandal M N A. Retinal Sphingolipids and Their Very-Long-Chain Fatty Acid-Containing Species. Investigative Ophthalmology & Visual Science. 2010; 51(9): 4422-31.

Harkewicz R, Du H, Tong Z, Alkuraya H, Bedell M, Sun W, Wang X, Hsu Y-H, Esteve-Rudd J, Hughes G, Su Z, Zhang M, Lopes V S, Molday R S, Williams D S, Dennis E A, Zhang K. Essential Role of ELOVL4 Protein in Very Long Chain Fatty Acid Synthesis and Retinal Function. J Biol Chem. 2012; 287(14):11469-80.

Kihara A. Very long-chain fatty acids: elongation, physiology and related disorders. Journal of Biochemistry. 2012; 152(5):387-95.

Liu A, Lin Y, Terry R, Nelson K, Bernstein P S. Role of long-chain and very-long-chain polyunsaturated fatty acids in macular degenerations and dystrophies. Clinical Lipidology. 2011; 6(5):593-613.

Logan S, Agbaga M-P, Chan M D, Kabir N, Mandal N A, Brush R S, Anderson R E. Deciphering mutant ELOVL4 activity in autosomal-dominant Stargardt macular dystrophy. Proc Natl Acad Sci USA. 2013; 110(14):5446-51.

Mattson M P, Bazan N G: Apoptosis and necrosis. In Basic Neurochemistry, 7th edition, G. Siegel, R. W. Albers, S. T. Brady, D. L. Price, eds, 2005.

McMahon A, Jackson S N, Woods A S, Kedzierski W. A Stargardt disease-3 mutation in the mouse Elovl4 gene causes retinal deficiency of C32-C36 acyl phosphatidylcholines. FEBS Letters. 2007; 581(28):5459-63

Okuda A, Naganuma T, Ohno Y, Abe K, Yamagata M, Igarashi Y, Kihara A. Hetero-oligomeric interactions of an ELOVL4 mutant protein: implications in the molecular mechanism of Stargardt-3 macular dystrophy. J Molecular Vision. 2010; 16:2438-45.

Olson D K, Fröhlich F, Christiano R, Hannibal-Bach H K, Ejsing C S, Walther T C. Rom2-dependent Phosphorylation of Elo2 Controls the Abundance of Very Long-chain Fatty Acids. Journal of Biological Chemistry. 2015; 290(7):4238-47.

Petasis N A, Yang R, Winkler J W, Zhu M, Uddin J, Bazan N G, Serhan C N. Stereocontrolled total synthesis of Neuroprotectin D1/Protectin D1 and its aspirin-triggered stereoisomer. Tetrahedron Lett. 2012; 53(14):1695-8.

Poulos A, Johnson D W, Beckman K, White I G, Easton C. Occurrence of unusual molecular species of sphingomyelin containing 28-34-carbon polyenoic fatty acids in ram spermatozoa. Biochemical Journal. 1987; 248(3):961-4.

Rice D S, Calandria J M, Gordon W C, Jun B, Zhou Y, Gelfman C M, Li S, Jin M, Knott E J, Chang B, Abuin A, Issa T, Potter D, Platt K A, Bazan N G. Adiponectin receptor 1 conserves docosahexaenoic acid and promotes photoreceptor cell survival. Nat Commun. 2015; 6:1-14. doi: 10.1038/ncomms7228.

Serhan C N, Gotlinger K, Hong S, Lu Y, Siegelman J, Baer T, Yang R, Colgan S P, Petasis N A. Anti-inflammatory actions of neuroprotectin D1/protectin D1 and its natural stereoisomers: Assignments of dihydroxy-containing docosatrienes. J. Immunol. 2006; 176(3):1848-59.

Serhan C N, Petasis N A. Resolvins and protectins in inflammation resolution. Chem Rev. 2011; 111(10):5922-43.

Stark D T, Bazan N G. Synaptic and Extrasynaptic NMDA Receptors Differentially Modulate Neuronal Cyclooxygenase-2 Function, Lipid Peroxidation, and Neuroprotection. The Journal of Neuroscience. 2011; 31(39):13710-21.

Zhou Q, Sheng M. NMDA receptors in nervous system diseases. Neuropharmacology. 2013; 74:69-75.

What is claimed is:

1. An eye drop formulation comprising a pharmaceutically acceptable carrier and a compound selected from the group consisting of:

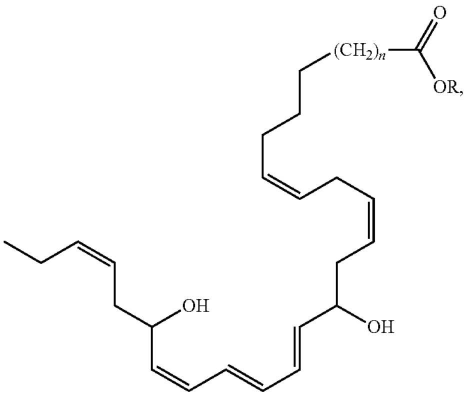

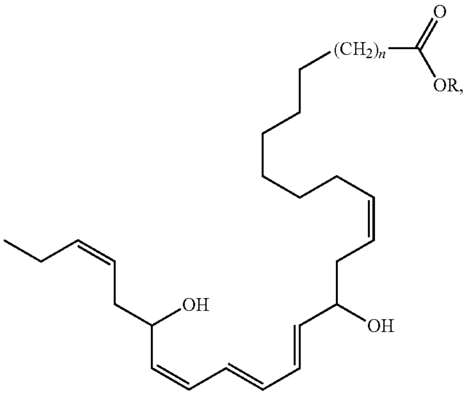

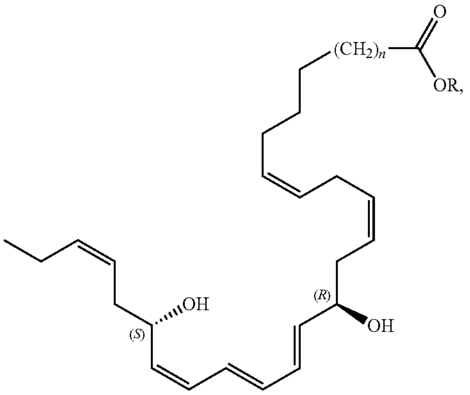

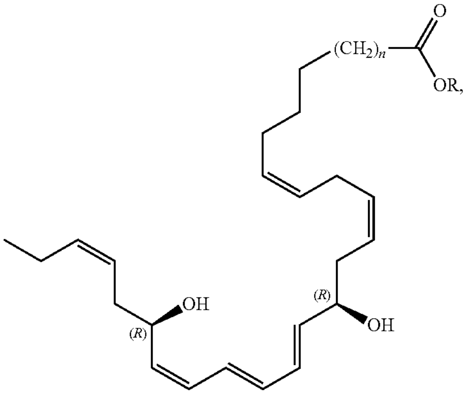

-continued
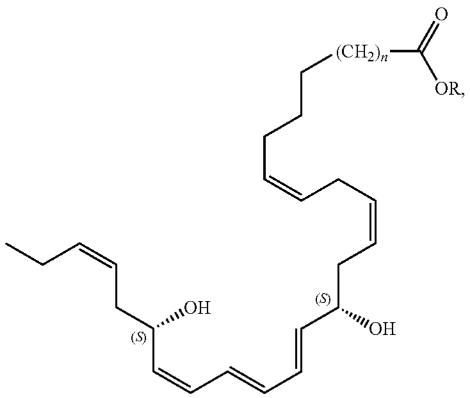
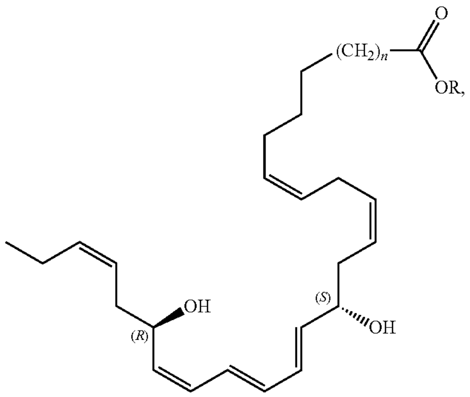
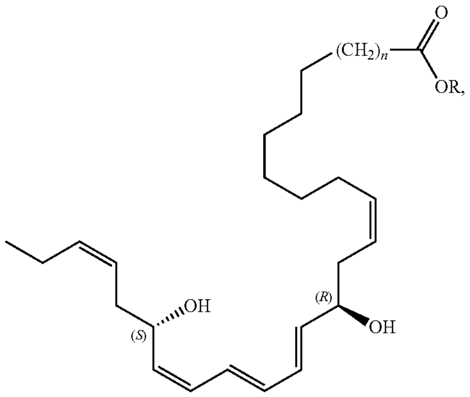
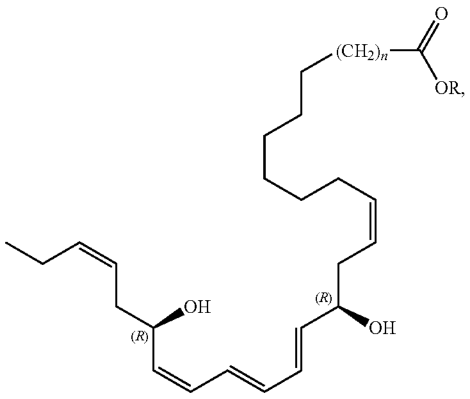
-continued
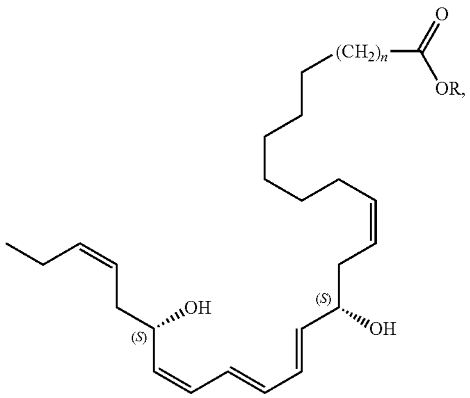
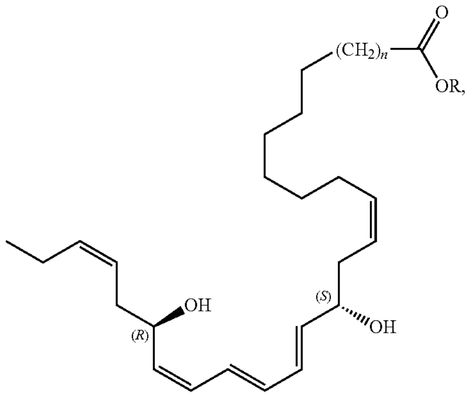
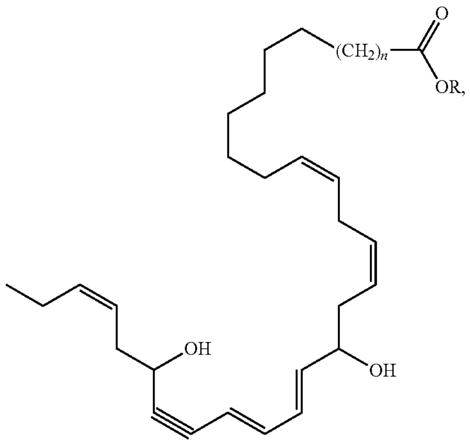
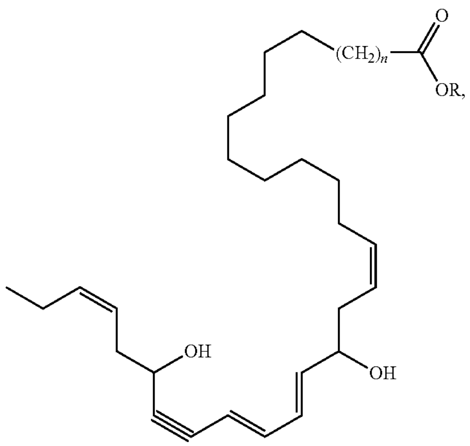

-continued

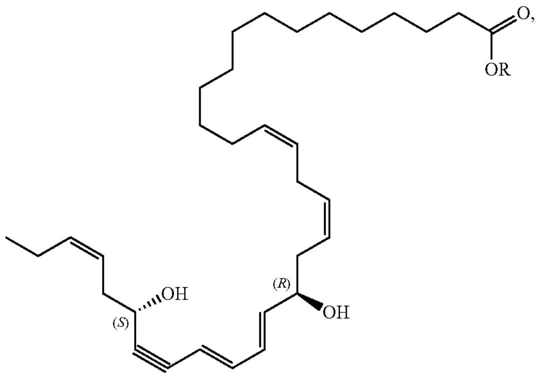

or

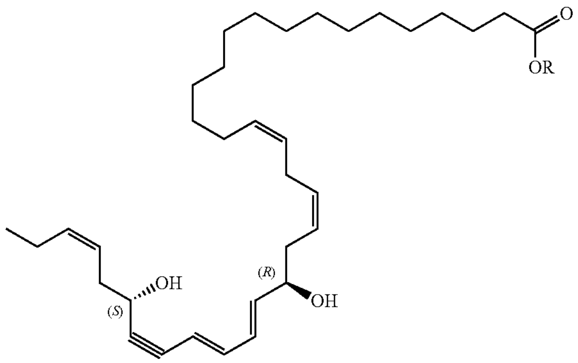

wherein n is 0 to 19; and the R group is selected from a group consisting of hydroxyl, methyl, ethyl, alkyl, or a cation forming a pharmaceutically acceptable salt selected from a group consisting of: ammonium cation, iminium cation, or a metal cation.

2. A controlled release formulation comprising: a controlled release system, a pharmaceutically acceptable carrier and a compound selected from the group consisting of:

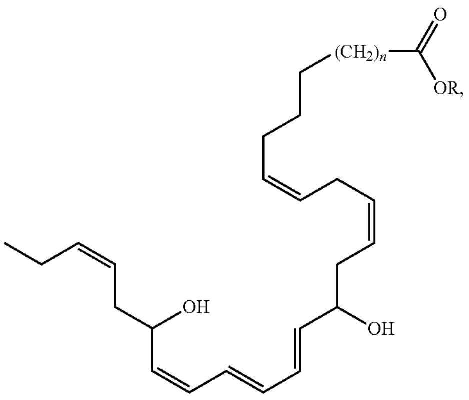

-continued

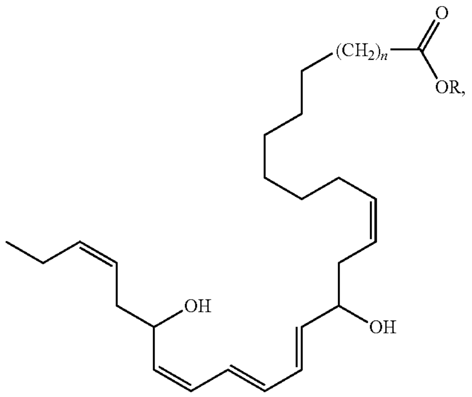

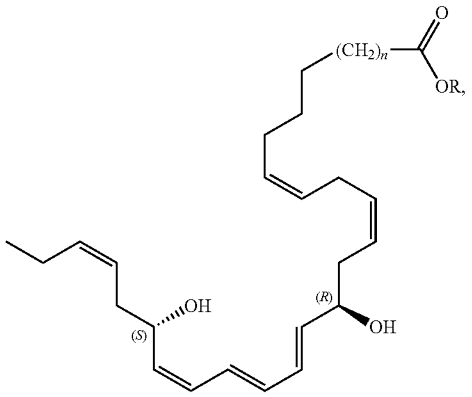

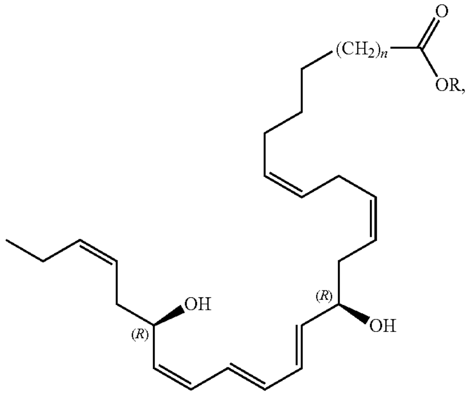

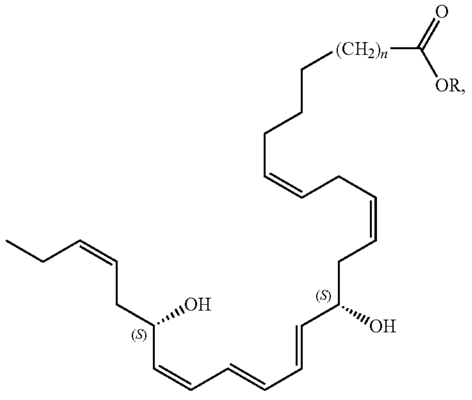

-continued
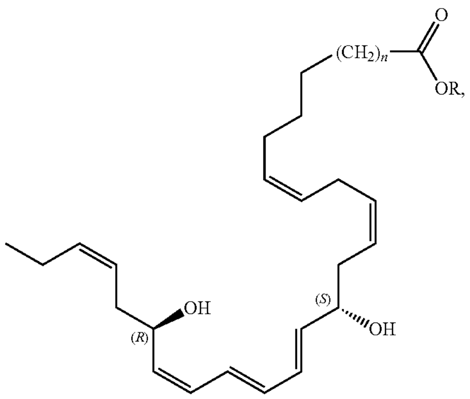
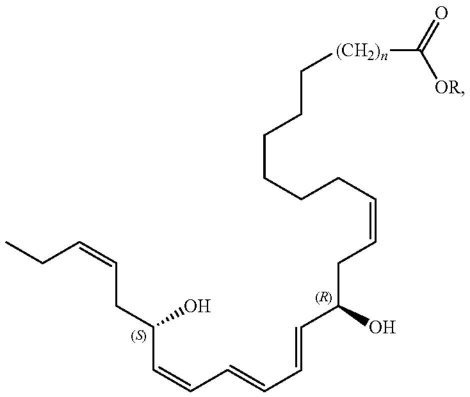
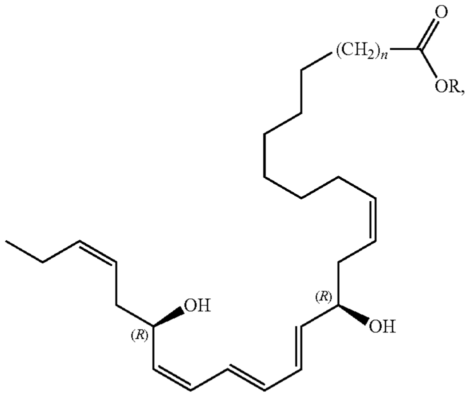
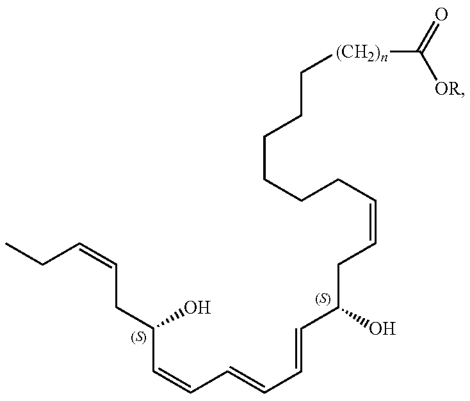
-continued
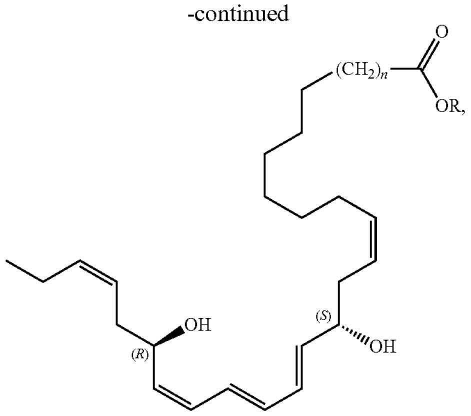
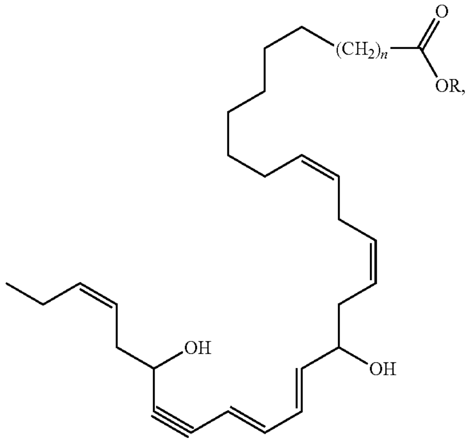
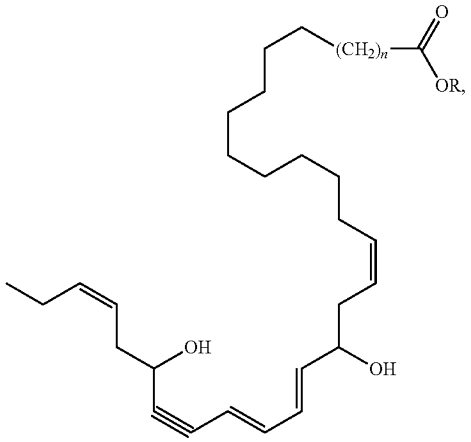
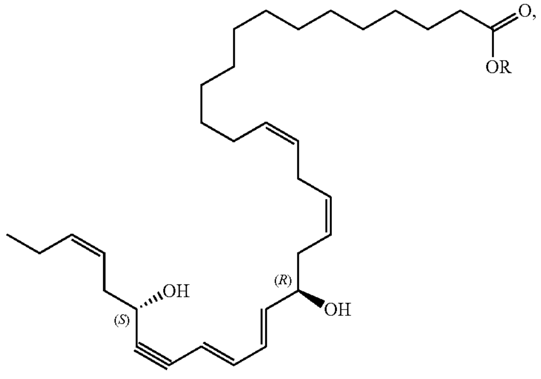
or -continued

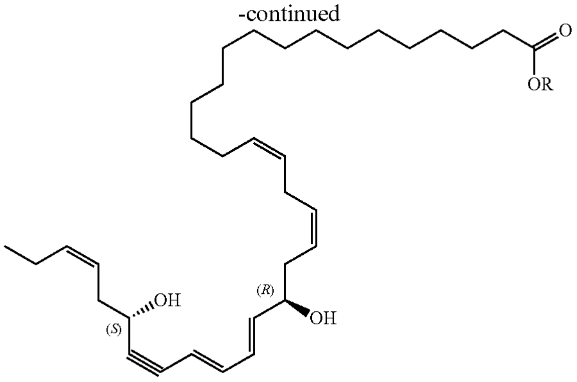

wherein n is 0 to 19; and the R group is selected from a group consisting of hydroxyl, methyl, ethyl, alkyl, or a cation forming a pharmaceutically acceptable salt selected from a group consisting of: ammonium cation, iminium cation, or a metal cation.

3. The controlled release formulation of claim 2, wherein the controlled release system is selected from the group consisting of an intravenous infusion, an implantable osmotic pump, a transdermal patch, or liposomes.

4. A sustained release pharmaceutical formulation comprising a sustained release matrix and a compound selected from the group consisting of:

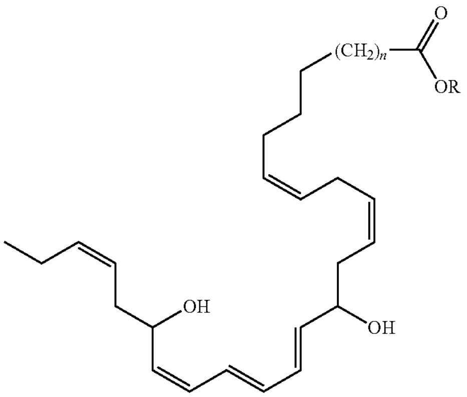

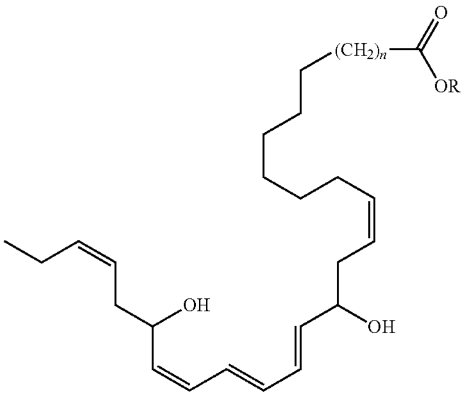

-continued

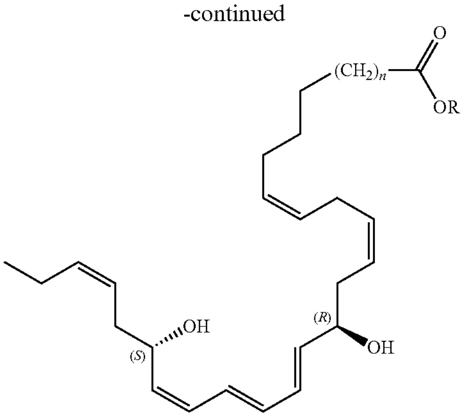

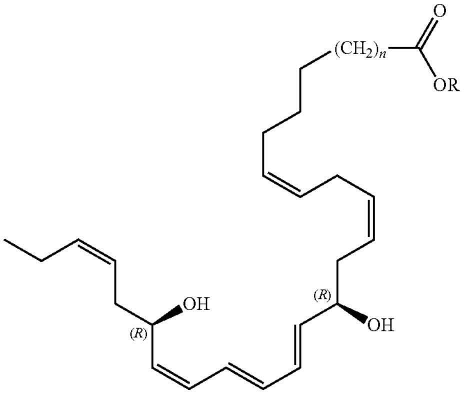

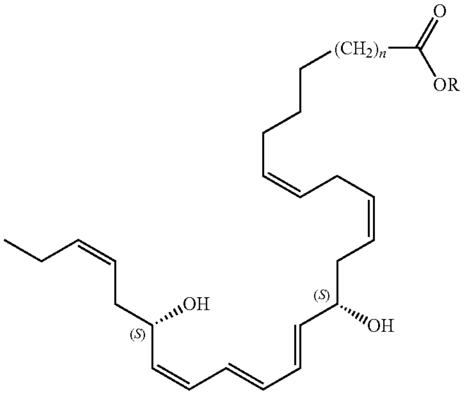

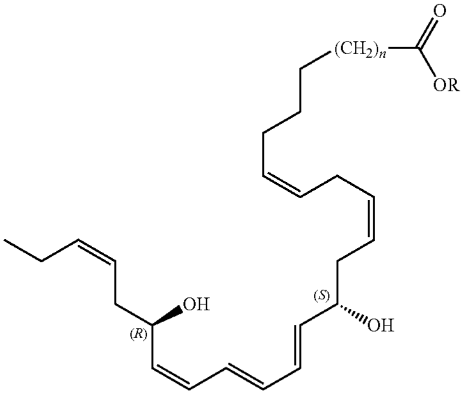

-continued
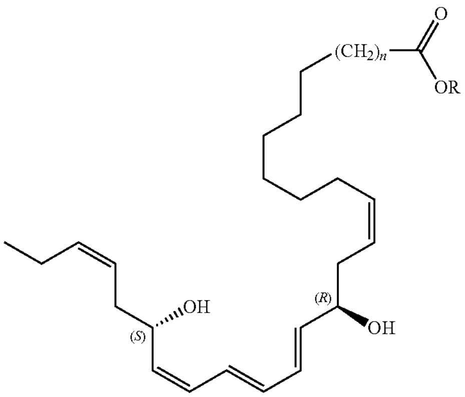
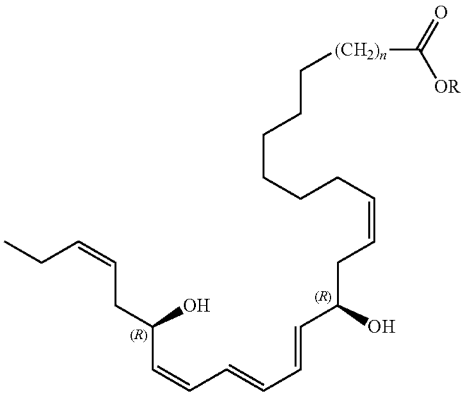
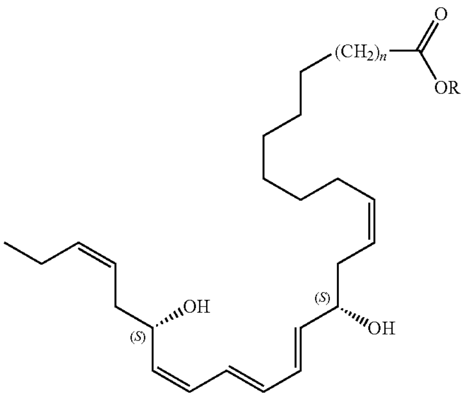
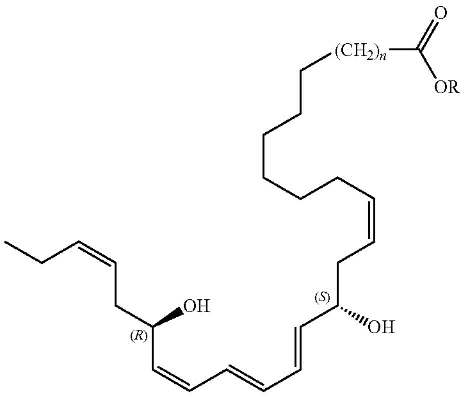
-continued
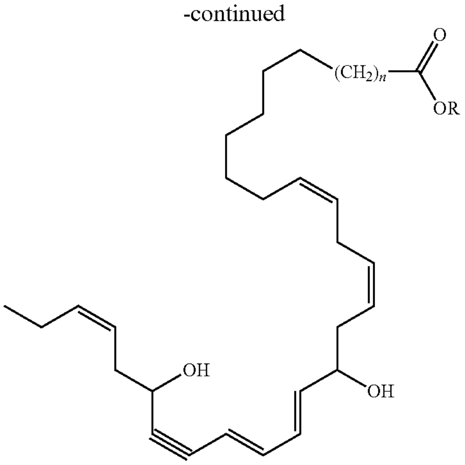
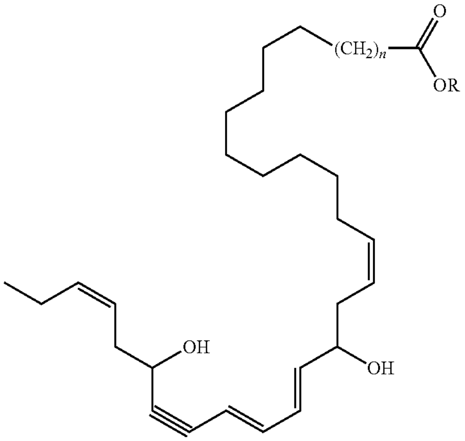
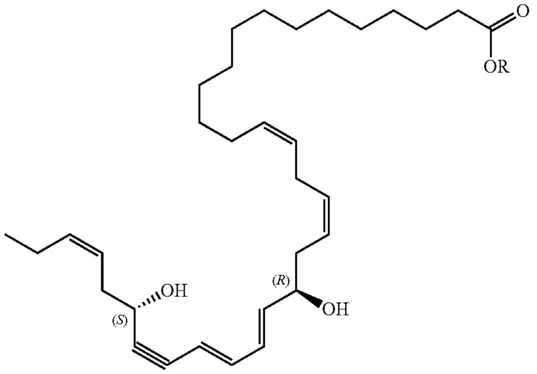
or
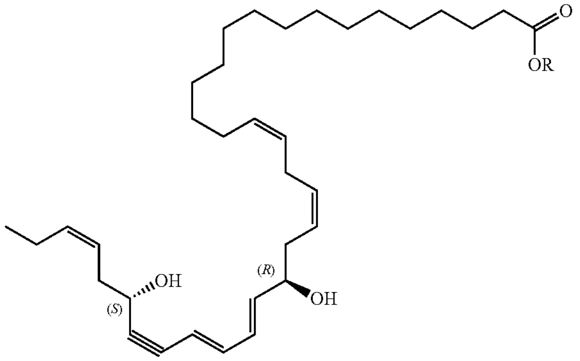
wherein n is 0 to 19; and
the R group is selected from a group consisting of hydroxyl, methyl, ethyl, alkyl, or a cation forming a pharmaceutically acceptable salt selected from a group consisting of: ammonium cation, iminium cation, or a metal cation.

5. The formulation of claim 4, wherein the sustained release matrix comprises liposomes, polylactides (polylactic acid), polyglycolide (polymer of glycolic acid), polylactide co-glycolide (copolymers of lactic acid and glycolic acid), polyanhydrides, poly (ortho) esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone, Illustrative biodegradable matrices include a polylactide matrix, a polyglycolide matrix, and a polylactide co-glycolide (co-polymers of lactic acid and glycolic acid) matrix.

6. A method of treating stroke in a subject in need thereof, wherein the method comprises administering to the subject an effective amount of the compound and a pharmaceutically acceptable carrier, wherein the compound is selected from the group consisting of:

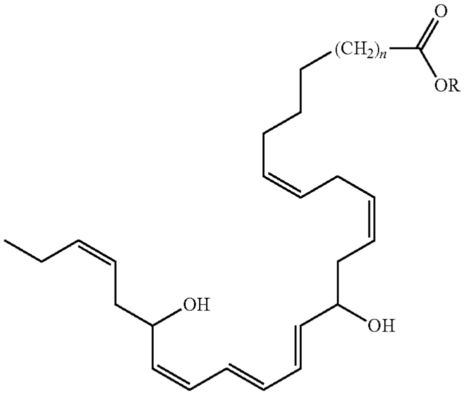

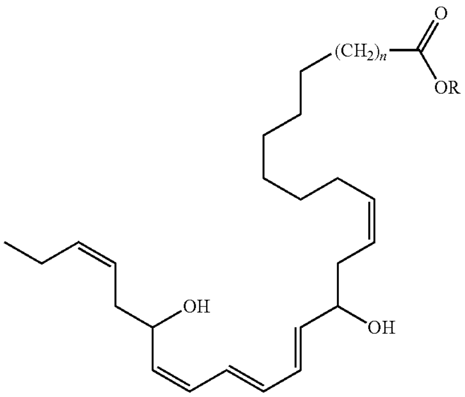

-continued

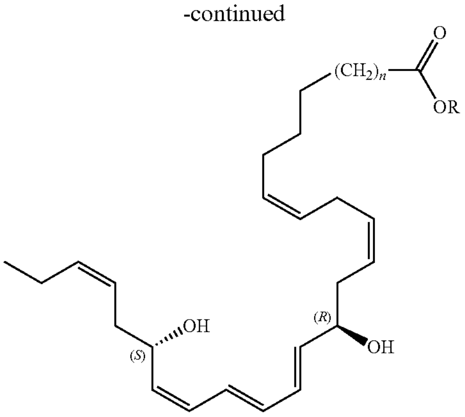

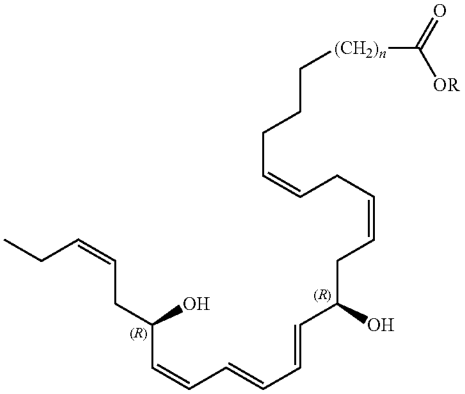

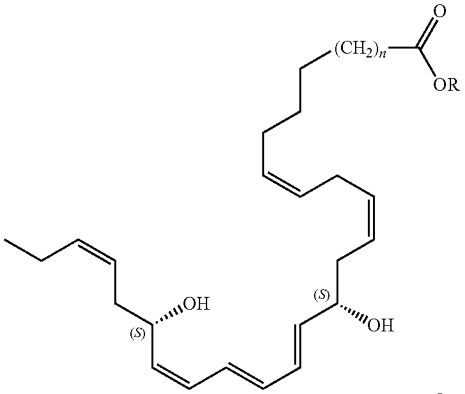

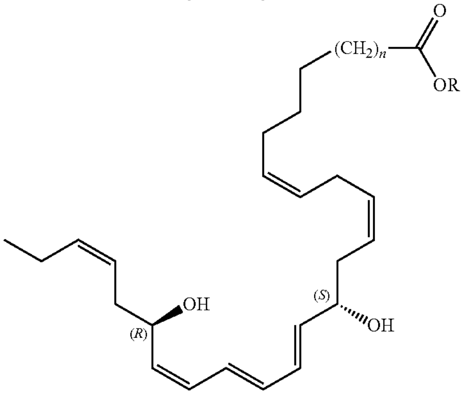

-continued
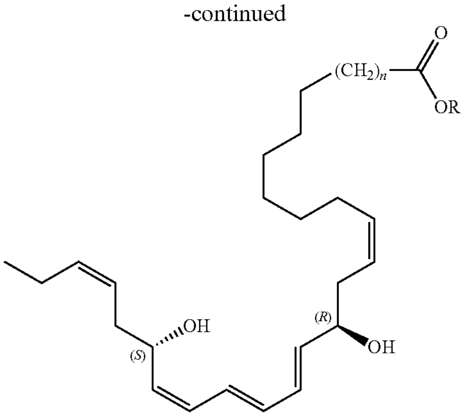
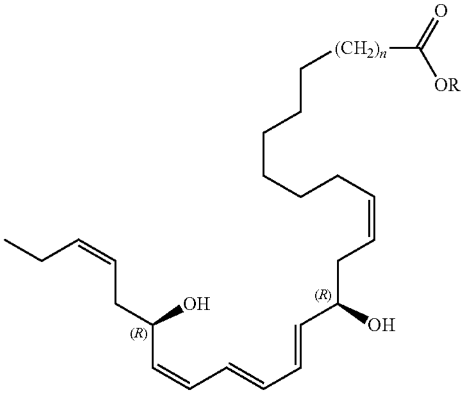
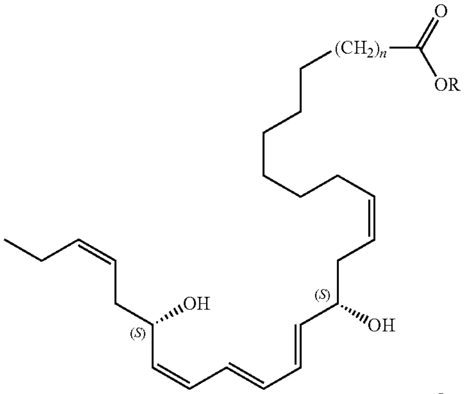
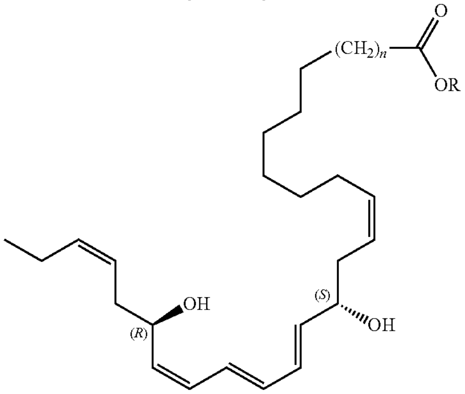
-continued
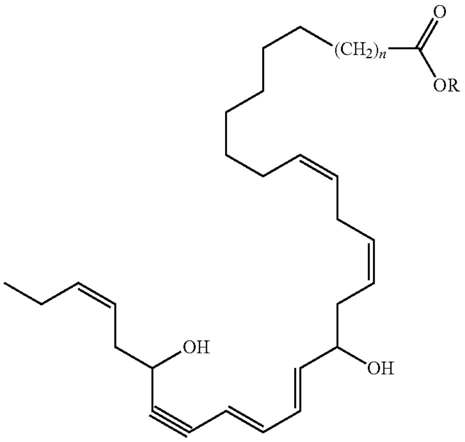
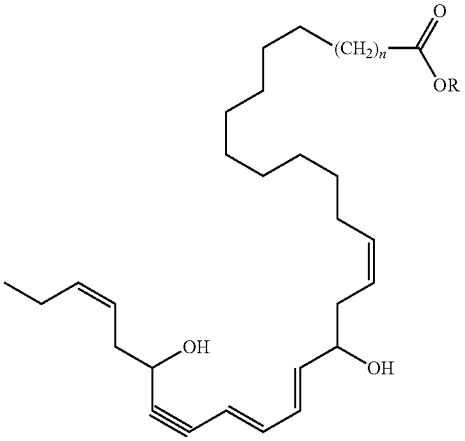
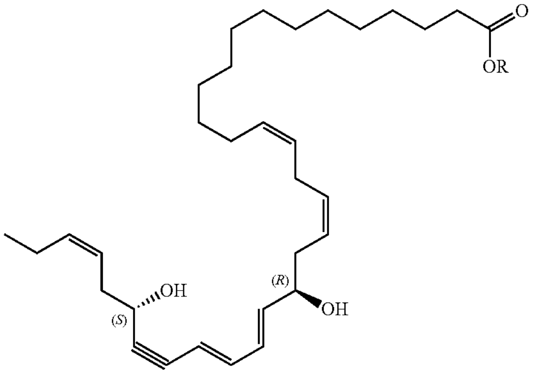
or
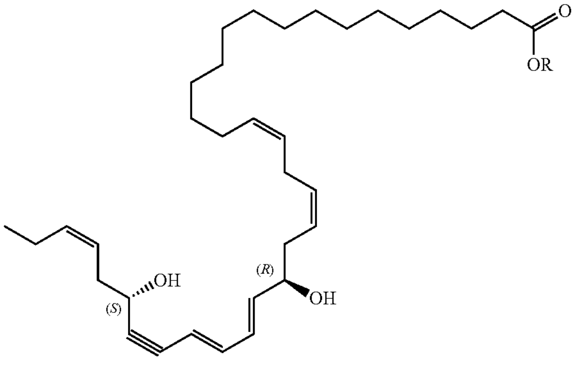
wherein n is 0 to 19; and
the R group is selected from a group consisting of hydroxyl, methyl, ethyl, alkyl, or a cation forming a pharmaceutically acceptable salt selected from a group consisting of: ammonium cation, iminium cation, or a metal cation.

* * * * *